US008618275B2

(12) United States Patent
Jensen et al.

(10) Patent No.: US 8,618,275 B2
(45) Date of Patent: Dec. 31, 2013

(54) EFFICIENT CELL CULTURE SYSTEM FOR HEPATITIS C VIRUS GENOTYPE 5A

(75) Inventors: Tanja Bertelsen Jensen, Frederiksberg C (DK); Judith M. Gottwein, Frederiksberg C (DK); Troels Kasper Høyer Scheel, Copenhagen Nv (DK); Jesper Eugen-Olsen, Hellerup (DK); Jens Bukh, Præstø (DK)

(73) Assignee: Hvidovre Hospital, Hvidovre (DK)

( * ) Notice: Subject to any disclaimer, the term of this patent is extended or adjusted under 35 U.S.C. 154(b) by 677 days.

(21) Appl. No.: 12/600,349

(22) PCT Filed: May 19, 2008

(86) PCT No.: PCT/DK2008/050113
§ 371 (c)(1),
(2), (4) Date: Oct. 4, 2010

(87) PCT Pub. No.: WO2008/141651
PCT Pub. Date: Nov. 27, 2008

(65) Prior Publication Data
US 2011/0021611 A1   Jan. 27, 2011

(30) Foreign Application Priority Data
May 18, 2007   (DK) .................................. 2007 00739

(51) Int. Cl.
C07H 21/00   (2006.01)
A61K 39/12   (2006.01)
A61K 39/29   (2006.01)
A61K 39/295  (2006.01)
C12N 7/00    (2006.01)

(52) U.S. Cl.
USPC .................. 536/23.72; 424/199.1; 424/202.1; 424/228.1; 435/235.1; 435/69.1

(58) Field of Classification Search
None
See application file for complete search history.

(56) References Cited

U.S. PATENT DOCUMENTS

| | | | |
|---|---|---|---|
| 5,428,145 A | 6/1995 | Okamoto et al. | |
| 6,638,714 B1 | 10/2003 | Linnen et al. | |
| 7,674,612 B2 | 3/2010 | Rice et al. | |
| 7,935,676 B2 * | 5/2011 | Wakita et al. | ............. 514/44 R |
| 2007/0073039 A1 | 3/2007 | Chisari | |
| 2010/0093841 A1 | 4/2010 | Gottwein et al. | |
| 2010/0158948 A1 | 6/2010 | Scheel et al. | |
| 2010/0278865 A1 | 11/2010 | Wakita et al. | |
| 2010/0291545 A1 | 11/2010 | Wakita et al. | |
| 2011/0021611 A1 | 1/2011 | Jensen et al. | |
| 2011/0045020 A1 | 2/2011 | Akazawa et al. | |
| 2011/0059512 A1 | 3/2011 | Gottwein et al. | |
| 2011/0059513 A1 | 3/2011 | Scheel et al. | |
| 2011/0092688 A1 | 4/2011 | Wakita et al. | |
| 2011/0294195 A1 | 12/2011 | Gottwein et al. | |
| 2012/0003714 A1 | 1/2012 | Hoelke et al. | |
| 2012/0003719 A1 | 1/2012 | Prento et al. | |

FOREIGN PATENT DOCUMENTS

| | | |
|---|---|---|
| EP | 1 801 209 A1 | 6/2007 |
| EP | 1 930 416 A1 | 6/2008 |
| WO | WO 99/04008 A2 | 1/1999 |
| WO | WO 01/21807 A1 | 3/2001 |
| WO | WO 02/052015 A2 | 7/2002 |
| WO | WO 02/059321 A2 | 8/2002 |
| WO | WO 2004/104198 A1 * | 2/2004 |
| WO | WO 2005/047463 A2 | 5/2005 |
| WO | WO 2005/053516 A2 | 6/2005 |
| WO | WO 2006/096459 A2 | 9/2006 |
| WO | WO 2007/037429 A1 | 4/2007 |
| WO | WO 2007/041487 A2 | 4/2007 |
| WO | WO 2007/073039 A1 | 6/2007 |
| WO | WO 2008/125117 A1 | 10/2008 |
| WO | WO 2008/125119 A1 | 10/2008 |
| WO | WO 2008/141651 A1 | 11/2008 |
| WO | WO 2009/080052 A1 | 7/2009 |
| WO | WO 2009/080053 A1 | 7/2009 |
| WO | 2011/118743 A1 | 9/2011 |

OTHER PUBLICATIONS

"Written Description Training Materials", United States Patent and Trademark Office, Department of Commerce, Mar. 2008, pp. 1-84, Revision 1 (Part 1).
"Written Description Training Materials", United States Patent and Trademark Office, Department of Commerce, Mar. 2008, pp. 1-84, Revision 1 (Part 2).
Gottwein et al., "Cutting the Gordian Knot-Development and Biological Relevance of Hepatitis C Virus Cell Culture Systems", Advances in Virus Research, 2008, pp. 51-133, vol. 71, Chapter 2.
International Preliminary Report on Patentability (Chapter II) for PCT/DK2008/050113 issued May 25, 2009.
Appel, Nicole et al., "Mutational Analysis of Hepatitis C Virus Nonstructural Protein 5A: Potential Role of Differential Phosphorylation in RNA Replication and Identification of a Genetically Flexible Domain" Journal of Virology, Mar. 2005, pp. 3187-3194, vol. 79, No. 5.

(Continued)

Primary Examiner — Stacy B. Chen
(74) Attorney, Agent, or Firm — Thompson Coburn LLP; Charles P. Romano

(57) ABSTRACT

The present inventors developed 5a/2a intergenotypic recombinants in which the JFH1 structural genes (Core, E1 and E2), p7 and all of or part of NS2 were replaced by the corresponding genes of the genotype 5a reference strain SA13. Compared to the J6/JFH control virus, after transfection of in vitro transcripts in Huh7.5 cells, production of infectious viruses was delayed. However, in subsequent viral passages efficient spread of infection and HCV RNA titers as high as for J6/JFH were obtained. Infectivity titers were at all time points analyzed comparable to J6/JFH control virus. Sequence analysis of recovered 5a/2a recombinants from 2 serial passages and subsequent reverse genetic studies revealed adaptive mutations in p7, NS2 and/or NS3. Infectivity of the 5a/2a viruses was CD81 and SR-BI dependant, and the recombinant viruses could be neutralized by chronic phase sera from patients infected with genotype 5a. Conclusion: The developed 5a/2a viruses provide a robust in vitro tool for research in HCV genotype 5, including vaccine studies and functional analyses of an increasingly important genotype in South Africa and Europe.

22 Claims, 14 Drawing Sheets

(56) References Cited

OTHER PUBLICATIONS

Appel, Nicole et al., "Essential Role of Domain III of Nonstructural Protein 5A for Hepatitis C Virus Infectious Particle Assembly" PLOS Pathogens, Mar. 2008, pp. 1-14, vol. 4, Issue 3.

Bukh, Jens et al., "Mutations that permit efficient replication of hepatitis C virus RNA in Huh-7 cells prevent productive replication in chimpanzees" Proc. Natl. Acad. Sci., Oct. 29, 2002, pp. 14416-14421, vol. 99, No. 22.

Chamberlain, Richard W. et al., "Complete nucleotide sequence of a type 4 hepatitis C virus variant, the predominant genotype in the Middle East" Journal of General Virology, 1997, pp. 1341-1347, vol. 78.

Forns, Xavier et al., "Hepatitis C virus lacking the hypervariable region 1 of the second envelope protein is infectious and causes acute resolving or persistent infection in chimpanzees" Proceedings of the National Academy of Sciences of the United States of America, Nov. 21, 2000, pp. 13318-13323, vol. 97, No. 24.

Gottwein, Judith M. et al., "Robust Hepatitis C Genotype 3a Cell Culture Releasing Adapted Intergenotypic 3a/2a (S52/JFH1) Viruses" Gastroenterology, 2007, pp. 1614-1626, vol. 133.

Gottwein, Judith M. et al., "Development and Characterization of Hepatitis C Virus Genotype 1-7 Cell Culture Systems: Role of CD81 and Scavenger Receptor Class B Type I and Effect of Antiviral Drugs" Hepatology, Oct. 9, 2008, pp. 364-377, vol. 49, No. 2.

Gottwein, Judith M. et al., "Monocistronic Hepatitis C Reporter Virus Recombinants of All Major Genotypes Expressing Enhanced Green Fluorescent Protein Tagged NS5A Protein" Journal of Hepatology, Apr. 2009, p. S33, vol. 50, No. sup1.

Gottwein, Judith M. et al., "Novel Chimeric Cell Culture Systems for Hepatitis C Genotypes 1A, 1B, 3A and 4A" J. Hepatology, Apr. 2007, p. S30, vol. 46.

Graham, Donald J. et al., "A genotype 2b NS5B polymerase with novel substitutions supports replication of a chimeric HCV 1b:2b replicon containing a genotype 1b NS3-5A background" Antiviral Research, 2006, pp. 24-30, vol. 69.

Hou, Wei et al., "A recombinant replication-competent hepatitis C virus expressing Azami-Green, a bright green-emitting fluorescent protein, suitable for visualization of infected cells" Biochemical and Biophysical Research Communications, Sep. 9, 2008, pp. 7-11, vol. 377, No. 1.

Jensen, Tanja Bertelsen "Efficient cell culture system for Hepatitis C Virus genotype 5a" Department of Infectious Diseases and Clinical Research Unit, Copenhagen University Hospital, Master Thesis, Mar. 2007, pp. 1-60.

Jensen, Tanja B. et al., "Highly Efficient JFH1-Based Cell-Culture System for Hepatitis C Virus Genotype 5a: Failure of Homologous Neutralizing-Antibody Treatment to Control Infection" Journal of Infectious Diseases, Dec. 15, 2008, pp. 1756-1765, vol. 198.

Kato, Takanobu et al., "Sequence Analysis of Hepatitis C Virus Isolated From a Fulminant Hepatitis Patient" Journal of Medical Virology, 2001, pp. 334-339, vol. 64.

Kato, Takanobu et al., "Efficient Replication of the Genotype 2a Hepatitis C Virus Subgenomic Replicon" Gastroenterology, 2003, pp. 1808-1817, vol. 125.

Kaul, Artur et al., "Cell Culture Adaptation of Hepatitis C Virus and in Vivo Viability of an Adapted Variant" Journal of Virology, Dec. 2007, pp. 13168-13179, vol. 81, No. 23.

Kim, Chow Saeng et al., "Monitoring the Antiviral Effect of Alpha Interferon on Individual Cells" Journal of Virology, Aug. 2007, pp. 8814-8820, vol. 81, No. 16.

Krieger, Nicole et al., "Enhancement of Hepatitis C Virus RNA Replication by Cell Culture-Adaptive Mutations" Journal of Virology, May 2001, pp. 4614-4624, vol. 75, No. 10.

Lindenbach, Brett D. et al., "Complete Replication of Hepatitis C Virus in Cell Culture" Science, Jul. 22, 2005, pp. 623-626, vol. 309.

Lohmann, Volker et al., "Mutations in Hepatitis C Virus RNAs Conferring Cell Culture Adaptation" Journal of Virology, Feb. 2001, pp. 1437-1449, vol. 75, No. 3.

Moradpour, Darius et al., "Insertion of Green Fluorescent Protein into Nonstructural Protein 5A Allows Direct Visualization of Functional Hepatitis C Virus Replication Complexes" Journal of Virology, Jul. 2004, pp. 7400-7409, vol. 78, No. 14.

Murphy, D. "Hepatitis C virus isolate QC69 polyprotein gene, complete cds" Database EMBL E.B.I. Hinxton U.K., Nov. 7, 2007.

Murphy, Donald et al., "A New Genotype of Hepatitis C Virus Originating From Central Africa" Hepatology, Oct. 2007, p. 623A, vol. 64, No. 4.

Pietschmann, Thomas et al., "Construction and characterization of infectious intragenotypic and intergenotypic hepatitis C virus chimeras" Proc. Natl. Acad. Sci., May 9, 2006, pp. 7408-7413, vol. 103, No. 19.

Prentoe, Jannick C. et al., "HCV entry related studies" Booklet, 4th Smögen Summer Symposium on Virology, Aug. 2008, p. 23.

Schaller, Torsten et al., "Analysis of Hepatitis C Virus Superinfection Exclusion by Using Novel Fluorochrome Gene-Tagged Viral Genomes" Journal of Virology, May 2007, pp. 4591-4603, vol. 81, No. 9.

Scheel, Troels K. H. et al., "Development of JFH1-based cell culture systems for hepatitis C virus genotype 4a and evidence for cross-genotype neutralization" Proceedings of the National Academy of Sciences, Jan. 22, 2008, pp. 997-1002, vol. 105, No. 3.

Simmonds, Peter et al., "Consensus Proposals for a Unified System of Nomenclature of Hepatitis C Virus Genotypes" Hepatology, Oct. 2005, pp. 962-973, vol. 42, No. 4.

Suzuki, T. et al., "Novel Chimeric hepatitis C virus genome comprising nucleic acid encoding epitope tag peptide at hypervariable region 1 of E2 protein, useful as vaccine for preventing or treating hepatitis-c viral infection" Database WPI Week 200914, Thomson Scientific, AN 2009-E03534, Jan. 22, 2009.

Wakita, Takaji et al., "Production of infectious hepatitis C Virus in tissue culture from a cloned viral genome" Nature Medicine, Jul. 2005, pp. 791-796, vol. 11, No. 7.

Yanagi, Masayuki et al., "Transcripts of a Chimeric cDNA Clone of Hepatitis C Virus Genotype 1b Are Infectious in Vivo" Virology, 1998, pp. 161-172, vol. 244.

Yi, Minkyung et al., "Compensatory Mutations in E1, p7, NS2, and NS3 Enhance Yields of Cell Culture-Infectious Intergenotypic Chimeric Hepatitis C Virus" Journal of Virology, Jan. 2007, pp. 629-638, vol. 81, No. 2.

Sakai et al., "In Vivo Study of the HC-TN Strain of Hepatitis C Virus Recovered from a Patient with Fulminant Hepatitis: TNA Transcripts of a Molecular Clone (pHC-TN) are Infectious in Chimpanzees But Not in Huh7.5 Cells", Journal of Virology, Jul. 2007, pp. 7208-7219, vol. 81, No. 13, American Society for Microbiology.

International Preliminary Report on Patentability for PCT/DK2008/050333 dated Mar. 29, 2010.

International Search Report and Written Opinion of the International Searching Authority dated Nov. 3, 2009 for PCT Application No. PCT/DK2008/050332.

Hui et al, "Interferon and Ribavirin Therapy for Chronic Hepatitis C Virus Genotype 6: A Comparison with Genotype 1", Article, Apr. 1, 2003, pp. 1071-1074, vol. 87.

Gen Bank Accession No: AB047639.1, HCV JFH1 complete genomic RNA, Nov. 12, 2005.

Gen Bank Accession No: Y12083.1, HCV genotype 6a RNA for HCV polyprotein, Nov. 10, 2005.

International Search Report and Written Opinion for PCT/DK2009/050193 dated Oct. 30, 2009.

Zhong et al., "Robust Hepatitis C Virus Infection in vitro", Proceedings of the National Academy of Sciences, 2005, pp. 9294-9299, vol. 102, No. 26.

* cited by examiner

EFFICIENT CELL CULTURE SYSTEM FOR HEPATITIS C VIRUS GENOTYPE 5A

CROSS REFERENCE TO RELATED APPLICATIONS

This application claims the benefit and priority to and is a U.S. National Phase Application of PCT International Application Number PCT/DK2008/050113, filed on May 19, 2008, designating the United States of America and published in the English language, which is an International Application of and claims the benefit of priority to Danish Patent Application No. PA 2007 00739, filed on May 18, 2007. The disclosures of the above-referenced applications are hereby expressly incorporated by reference in their entireties.

FIELD OF THE INVENTION

The present invention provides infectious recombinant hepatitis C genotype 5 viruses (HCV), and vectors, cells and animals comprising the same. The present invention provides methods of producing the infectious recombinant HCV genotype 5, and their use in identifying anti-HCV therapeutics including use in vaccines and diagnostics, as well as sequences of HCV associated with HCV pathogenesis.

BACKGROUND

Hepatitis C is one of the most widespread infectious diseases in the world. About 170 million people are infected with hepatitis C virus (HCV) worldwide with a yearly incidence of 3-4 million. While the acute phase of infection is mostly asymptomatic, the majority of acutely infected individuals develops chronic hepatitis and is at increased risk of developing liver cirrhosis and hepatocellular carcinoma. Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and posttranslationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 6 major HCV genotypes (genotypes 1-6) have been identified, which differ in nucleotide and amino acid sequence composition by 31-35% (Bukh et al. 1993). In addition, there are numerous subtypes (a, b, c, etc.). Genotype 5a is only commonly found in South Africa where it represents 30% of the HCV infections detected. HCV genotype 5a is found in less than 3% of the infected population in countries with sporadic cases. However, recently there have been reports on regional high prevalence of HCV genotype 5a, in the central part of France. Genotyping of patients in this region studied from (1996-2002) showed a prevalence of 14%, making genotype 5a the $3^{rd}$ most frequent subtype, and interestingly the patients were from a settled, older part of the population where the reason was less likely to be transmission from intravenous drug use or travel to endemic countries. In another recent study of patients in Flandern, Belgium, a prospective study from 2001 to 2004 showed that genotype 5a was the second most prevalent genotype in that area with 30% prevalence compared to 50% prevalence of genotype 1.

The only approved therapy for HCV comprises a combination therapy with interferon and ribavirin. Such therapy is expensive and associated with severe side-effects and contraindications. Sustained viral response can be achieved in only about 55% of treated patients in general, in 85-90% of patients infected with genotypes 2 and 3 and only in 40-50% of patients infected with other genotypes. There is no vaccine against HCV.

Since its discovery in 1989, research on HCV has been hampered by the lack of appropriate cell culture systems allowing for research on the complete viral life cycle as well as new therapeutics and vaccines. Full-length consensus cDNA clones of HCV strain H77 (genotype 1a) and J6 (genotype 2a) shown to be infectious in the chimpanzee model were apparently not infectious in vitro. Replicon systems permitted the study of HCV RNA replication in cell culture using the human liver hepatoma cell line Huh7 but were dependent on adaptive mutations that were deleterious for infectivity in vivo.

In 2001, a genotype 2a isolate (JFH1) was described (Kato et al., 2001), which yielded high RNA titers in the replicon system without adaptive mutations (Kato et al., 2003).

A major breakthrough occurred in 2005, when formation of infectious viral particles was reported after transfection of RNA transcripts from the JFH1 full-length consensus cDNA clone into Huh7 cells (Wakita et al., 2005) (Zhong et al., 2005)

At the same time, Lindenbach et al. demonstrated that the intragenotypic 2a/2a recombinant genome (J6/JFH1), in which the structural genes (C, E1, E2), p7 and NS2 of JFH1 were replaced by the respective genes of clone J6CF, produced infectious viral particles in Huh7.5 cells (a cell line derived from bulk Huh7 cells) with an accelerated kinetic (Lindenbach et al., 2005). Cell culture derived J6/JFH viruses were apparently fully viable in vivo.

Despite the importance of the described cell culture systems they represent only a single subtype (genotype 2a) of HCV. It is important to develop cell culture systems for representative strains of other HCV genotypes, since neutralizing antibodies are not expected to cross-neutralize all genotypes and new specific antiviral compounds might have differential efficiencies against different genotypes. For the genotype specific study of the function of the structural proteins, p7 and NS2 as well as related therapeutics such as neutralizing antibodies, fusion inhibitors, ion-channel blockers and protease inhibitors, it would be sufficient to construct intergenotypic recombinant viruses in analogy to J6/JFH.

Pietschmann et al. 2006 disclose construction and characterization of infectious intragenotypic and intergenotypic hepatitis C virus recombinants. The authors created a series of recombinant genomes allowing production of infectious genotype 1a, 1b, 2a and 3a particles by constructing hybrid genomes between the JFH1 isolate and the HCV isolates: H77 (genotype 1a), Con1 (genotype 1b), J6 (genotype 2a) and 452 (genotype 3a) respectively. Thus, disclosing both genotypes completely different from the genotype disclosed in the present application and relating to completely different strains of origin.

The infectious titers of the 1a, 1b and 3a genotypes disclosed in Pietschmann et al. 2006 are not at a level sufficiently high for practical utilization in functional analysis, drug and vaccine development or other applications. For such applications, including screening of potential drugs and development of potential vaccine candidates, the skilled person will know that infectivity titers below $10^3$ TCID50/mL contain insufficient amounts of infectious virus.

Accordingly, the study does not attempt cell culture adaptation of the genotype recombinants, e.g. by serial passage of cell culture derived viruses to naïve cells and it is not investigated whether adaptive mutations develop after transfection in cell culture. In fact, Pietschmann et al does not even provide any sequence data of the virus produced in the cell culture.

SUMMARY OF THE INVENTION

In this study, the present inventors used the SA13 reference isolate (genotype 5a) to construct a viable, JFH1-based genome. The present inventors serially passaged SA13/JFH1 virus in cell culture and obtained both high infectivity titers, high HCV RNA titers and identified adaptive mutations required for efficient growth.

The present inventors have developed a robust cell culture system for HCV genotype 5a. This is an important advance for the study of HCV, since it permits detailed molecular studies of HCV and enhances the potential for developing broadly reactive reagents against HCV, including but not limited to small molecule drugs, antibodies and vaccines. Accordingly, the present invention may be used for individualised treatment of patients infected with one of the six major genotypes.

One aspect of the present invention pertains to an a replicating RNA comprising the structural genes (Core, E1, E2), p7 and the non-structural gene NS2 of genotype 5a and the non-structural genes NS3, NS4A, NS4B, NS5A and NS5B from the JFH1 strain.

In another aspect the present invention pertains to an isolated nucleic acid molecule which encodes human hepatitis C virus of genotype 5a/JFH1, wherein said molecule is capable of expressing said virus when transfected into cells.

In yet another aspect the present invention pertains to a composition comprising a nucleic acid molecule according to the present invention, a cassette vector for cloning viral genomes, methods for producing a cell which replicates HCV 5a/JFH1 RNA and cells obtainable there from.

In another aspect the present invention pertains to methods for producing a hepatitis C virus particle, methods for in vitro producing a hepatitis C virus-infected cell.

In a further aspect the present invention pertains to methods for screening an anti-hepatitis C virus substance, hepatitis C vaccines comprising a hepatitis C virus particle, methods for producing a hepatitis C virus vaccine and antibodies against hepatitis C virus.

Figure 5:
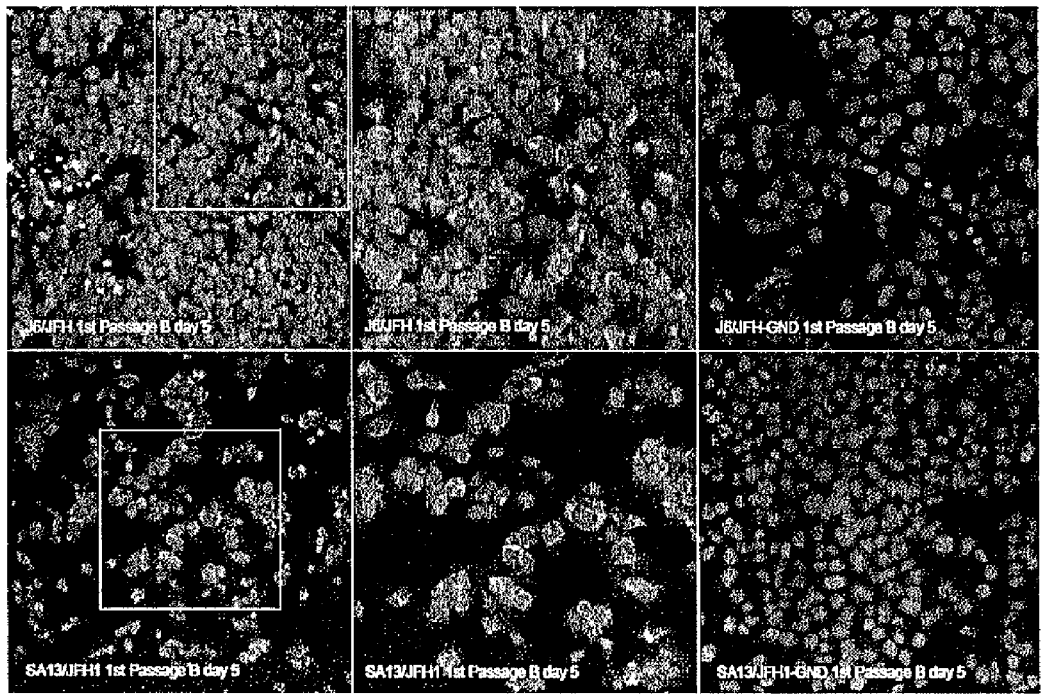

FIG. 5. Immunofluorescence staining of Huh7.5 cells during 1st passage of SA13/JFH1 and J6/JFH viruses. Naïve Huh7.5 cells were inoculated with supernatant from the transfection experiment as described in FIG. 10 legend. The figure shows cell slides of the 1st passage B day 5 for SA13/JFH1, J6/JFH and the replication deficient J6/JFH(GND) and SA13/JFH1-GND. The white boxes in the 1st column show the enlarged detail in the 2nd column. Core staining was performed as described in FIG. 8 and in Materials and Methods.

Figure 6:
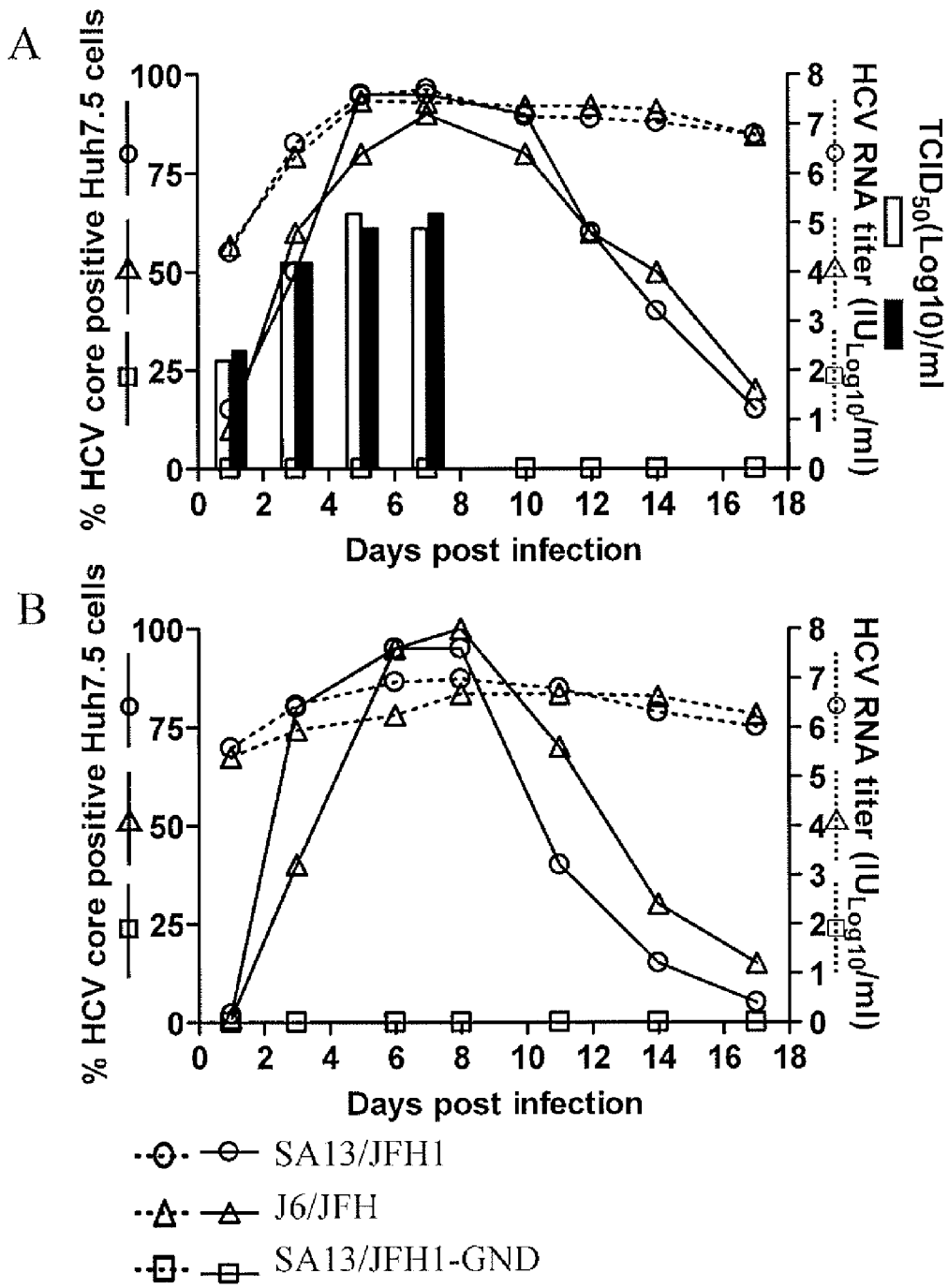

FIG. 6. 2nd passage virus kinetic experiments of SA13/JFH1 and J6/JFH. Naïve Huh 7.5 cells were plated $4 \times 10^5$ cells/well in a 6-well plate 24 hrs before cells were inoculated with sterile filtered supernatants from the 1st passages. The cells were split every 2-3 days and stained for Core. The percentage of infected cells was determined as described above (Left y-axis). HCV RNA titers (Right y-axis) were determined as described in FIG. 10 and Materials and Methods. Infectivity titers TCID50 (extreme right y-axis) were determined as described in FIG. 9 and Materials and Methods. A: Supernatant of SA13/JFH1 and J6/JFH from day 3 of the 1st passage A cell culture was used for infection; the dose of the inoculum was $10^{3.3}$ TCID50 for both. The negative control SA13/JFH1-GND was also from day 3. B: Supernatant of SA13/JFH1 and J6/JFH from day 7 of 1st passage B was used for infection; the doses of the inoculum were $10^{4.2}$ and $10^{4.3}$ TCID50, respectively. The negative control SA13/JFH1-GND was from the same day.

Figure 7:
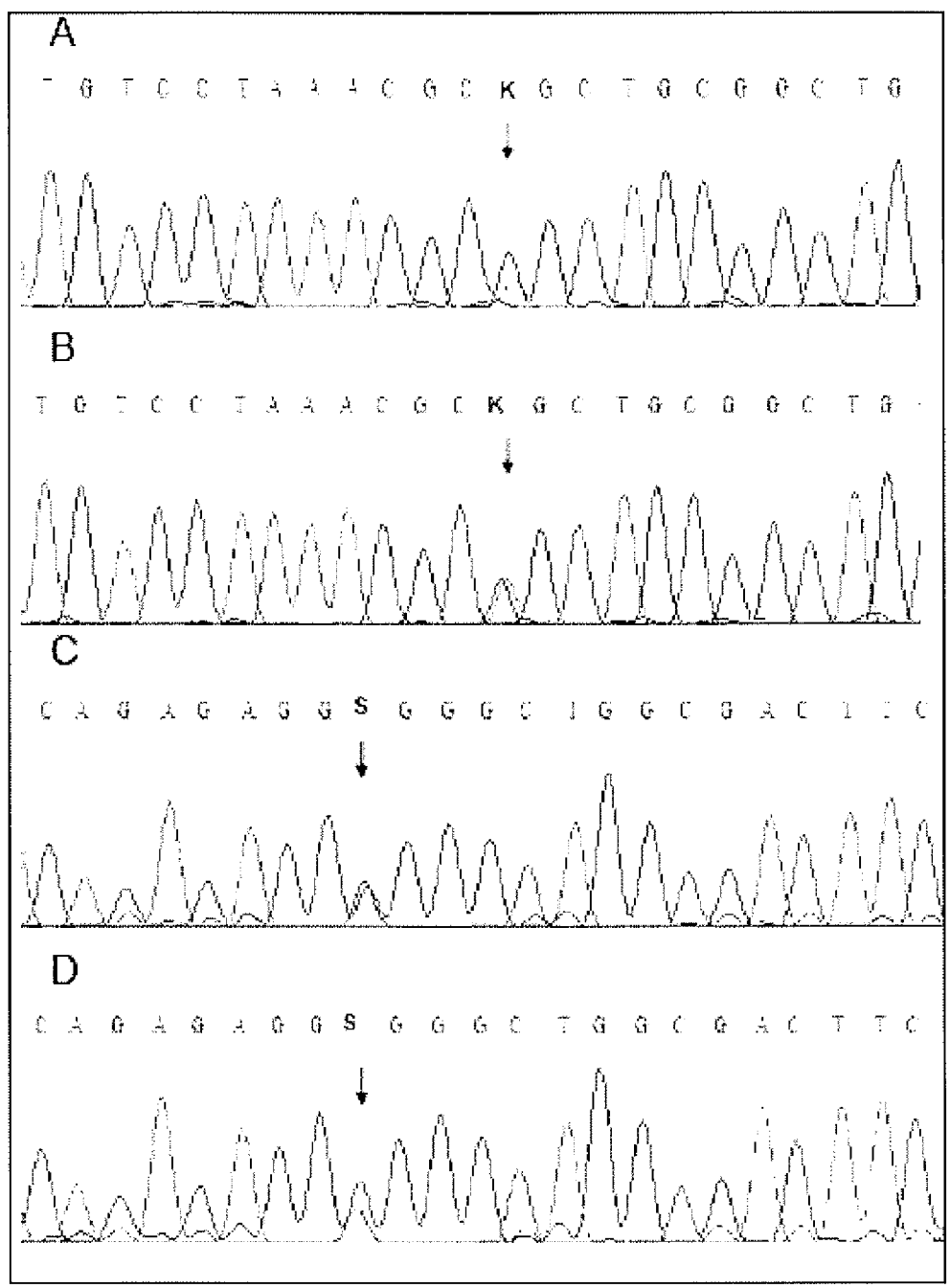

FIG. 7. Sequence data indicating quasispecies of cell culture derived SA13/JFH1 (SEQ ID NO: 1) A: 1st Passage B (day 7) of SA13/JFH1 culture, nt. 2611 is showed by an arrow, the distribution of the sequences is G/t, t being the minor sequence. t is the mutated sequence. B: 2nd Passage A (day 7) of SA13/JFH1 culture, nt. 2611 is showed by an arrow, in the 2nd passage there is a 50:50 distribution of G/T. T is the mutated sequence. C: 1st Passage B (day 7) of SA13/JFH1 culture, nt. 3405 is showed by an arrow, there is a 50:50 distribution of C/G. G is the mutated sequence. D: 2nd Passage A (day 7) of SA13/JFH1, nt. 3405 is showed by an arrow, C/G distribution with G being the major sequence. G is the mutated sequence.

Figure 8:
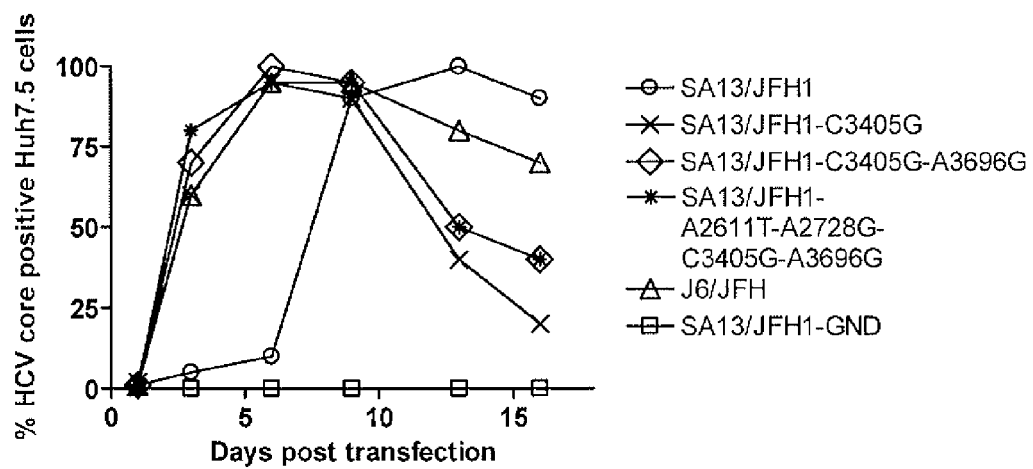

FIG. 8. Transfection of Huh7.5 cells with RNA transcripts of mutated genomes of pSA13/JFH1 to determine the effect of putative adaptive mutations. Huh7.5 cells transfected with RNA transcripts of pSA13/JFH1 (SEQ ID NO: 1), pFL-J6/JFH and the replication deficient pSA13/JFH1-GND served as controls. The mutations tested in this experiment are at nucleotide positions G2611T (p7), A2728G (p7), C3405G (NS2) and A3696G (NS3) in pSA13/JFH1. Mutation C3405G was tested alone and in combination with A3696G or all 3 mutations found in passed SA13/JFH1 viruses. Only C3405G and A3696G caused amino acid changes (A1022G and K1119R respectively). Huh7.5 cells were transfected with 2.5 µg of RNA transcripts of pSA13/JFH1 (SEQ ID NO: 1), C3405G-SA13/JFH1 (SEQ ID NO: 54), C3405G-A3696G-SA13/JFH1 (SEQ ID NO: 55), G2611T-A2728G-C3405G-A3696G-SA13/JFH1 (SEQ ID NO: 56), pFL-J6/JFH and pSA13/JFH1-GND.

Figure 9:
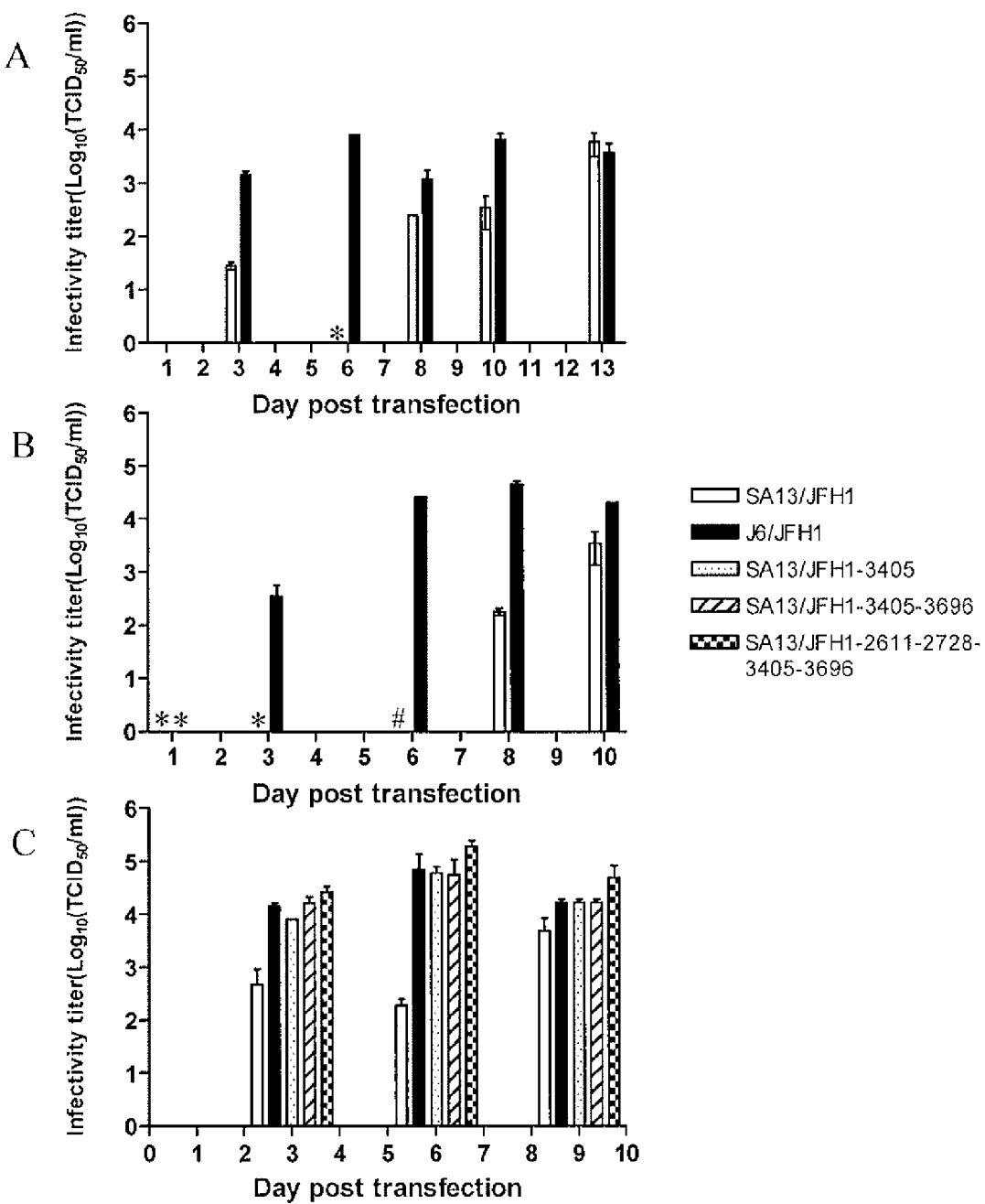

FIG. 9. Transfection of Huh7.5 cells with SA13/JFH1 . A, B. Transfection of Huh7.5 cells with RNA transcripts of pSA13/JFH1 (SEQ ID NO: 1) and pJ6/JFH. In two independent experiments, infectivity titers were determined in duplicates by a $TCID_{50}$ assay (left y-axis). Error bars indicate standard deviations of the mean. * Infectivity titer $<10^1$ $TCID_{50}$/mL (<3 of 6 replicate wells infected by undiluted supernatant) in two independent determinations; # Infectivity titer $10^{1.3}$ and $<10^1$ $TCID_{50}$/mL, respectively, in two independent determinations. C. Transfection of Huh7.5 cells with RNA transcripts of pSA13/JFH1 (SEQ ID NO: 1), C3405G-SA13/JFH1 (SEQ ID NO: 54), C3405G-A3696G-SA13/JFH1 (SEQ ID NO: 55), G2611T-A2728G-C3405G-A3696G-SA13/JFH1 (SEQ ID NO: 56) and pJ6/JFH. Infectivity titers were determined in duplicates by a $TCID_{50}$ assay (left y-axis). Error bars: Standard deviations of the mean.

Figure 10:
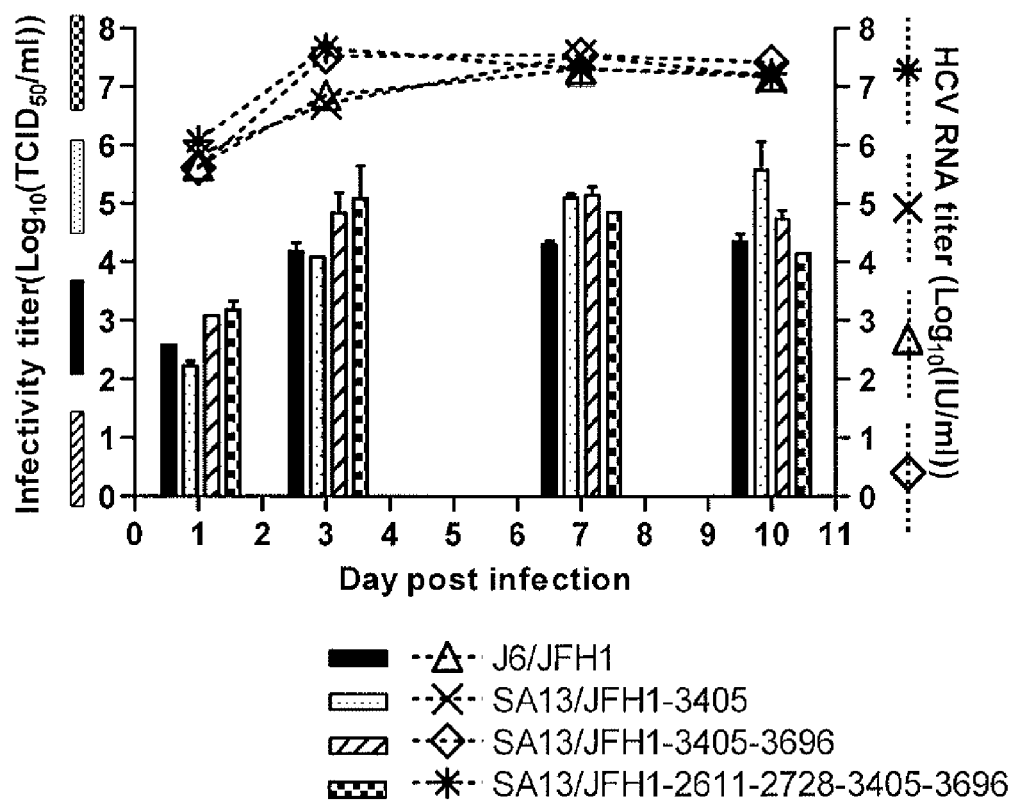

FIG. 10. Importance of SA13/JFH1 adaptive mutations. $1^{st}$ passage of SA13/JFH1 viruses with putative adaptive mutations. Huh7.5 cells were inoculated with ~$10^5$ $TCID_{50}$ of C3405G-SA13/JFH1 (SEQ ID NO: 54), C3405G-A3696G-SA13/JFH1 (SEQ ID NO: 55), G2611T-A2728G-C3405G-A3696G-SA13/JFH1 (SEQ ID NO: 56) or J6/JFH (from day 6 of the transfection experiment, FIG. 9C). Infectivity titers (left y-axis) and supernatant HCV RNA (right y-axis) were determined in duplicates; see also FIG. 9 legend. Error bars: Standard deviations of the mean.

Figure 11:
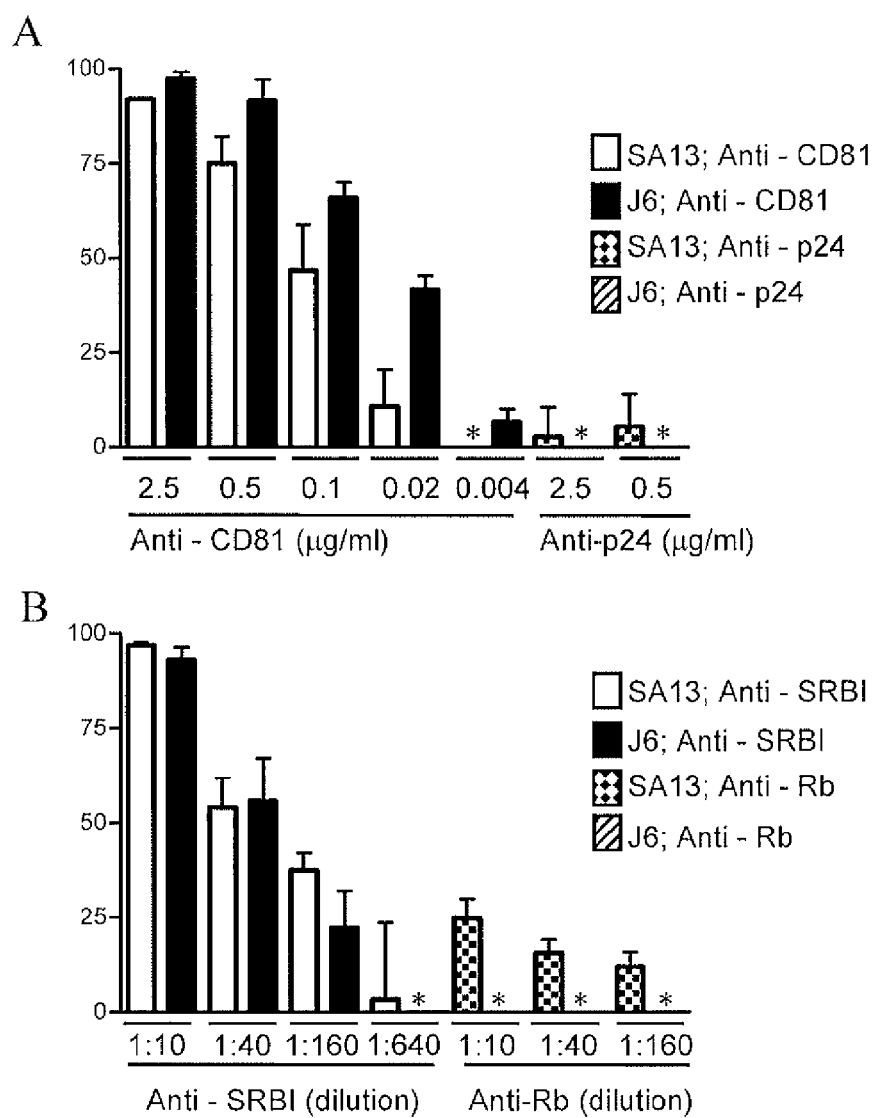

FIG. 11. SA13/JFH1 infection inhibited by blocking of CD81 (A) and SR-BI (B). Huh7.5 cells were incubated with anti-CD81 or anti-SR-BI antibodies at the indicated concentrations before infection with ~50 FFUs of SA13/JFH1-C3405G-A3696G (SEQ ID NO: 55) and J6/JFH, respectively. An isotype-matched antibody against HIV p24 was used as a control for anti-CD81 blocking and a polyclonal antibody against human retinoblastoma (Rb) protein was used as control for anti-SR-BI blocking. Each antibody concentration was tested in triplicates, except anti-SR-BI 1:160 dilution, which was tested in six replicates. The percentage of inhibition was calculated by comparison of the number of FFUs in wells inoculated with antibody treated virus to the mean number of FFUs in 3 wells inoculated with virus only. Error bars: Standard error of the mean. * Values below 0.

Figure 12:
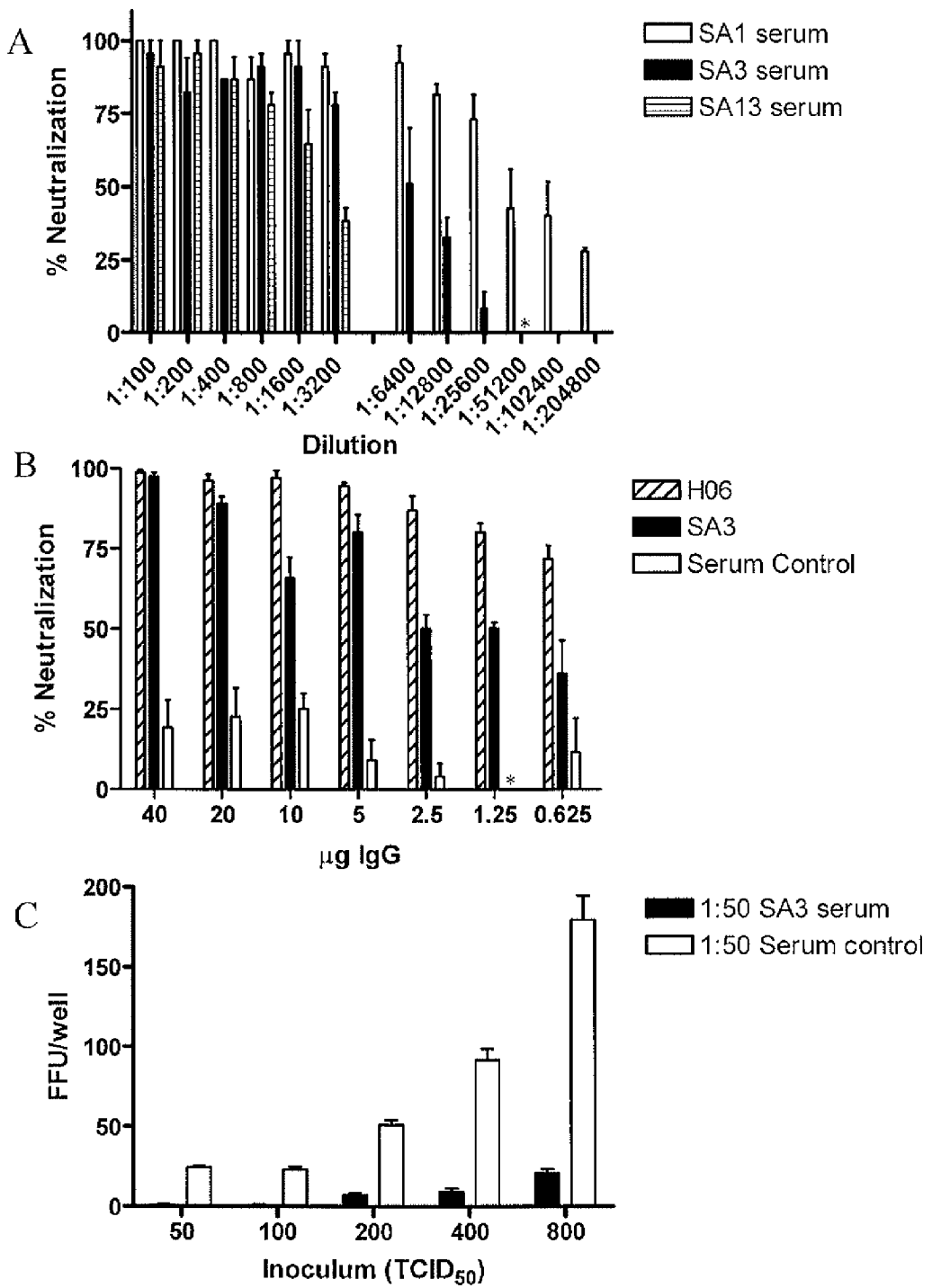

FIG. 12. Neutralization of SA13/JFH1 with sera and purified IgG from genotype 5a infected patients. A. ~100 $TCID_{50}$ of SA13/JFH1 (SEQ ID NO: 1) were incubated with serial 2 fold dilutions (1:100 to 1:3200) of SA1 (white), SA3 (black) or SA13 (striped) serum for 1 hour. To determine the 50% endpoint titers for SA1 and SA3 an additional experiment was performed with further dilutions of the respective sera from 1:6,400 to 1:51,200 for SA3 and 1:6,400 to 1:204,800 for SA1. For comparison, similar experiments were done using serum control. Huh7.5 cells were incubated with virus/serum mixtures for 3 hours, before washing and incubation for 48 hours. Experiments were done in triplicates. The percentage of neutralization was calculated by comparing the number of FFUs after 5a serum incubation at each dilution with the grand average of FFUs for the serum control in the experiment (~10 and ~30 FFUs in the first and second experiment, respectively). B. 100 FFUs SA13/JFH1$_{C3405G-A3696G}$ (SEQ ID NO: 55) were incubated with 2 fold dilutions of SA3 (black) or H06 (crossed) purified IgG for 1 hour before incubation with Huh7.5 cells for 3 hours and development as described in FIG. 12A. Percent neutralization was calculated by comparison to the mean of FFU counts from 6 replicates of virus only (~80 FFUs). C. ~50, 100, 200, 400 or 800 TCID$_{50}$SA13/JFH1$_{C3405G\text{-}A3696G}$ (SEQ ID NO: 55) were incubated with a 1:50 dilution of SA3 serum (black) or serum control (white) before addition to 6×10$^3$ Huh7.5 cells. Neutralization assay done as in FIG. 12A. FIG. 12 A, B, C; error bars: Standard errors of the mean; * value below 0%.

Figure 13:
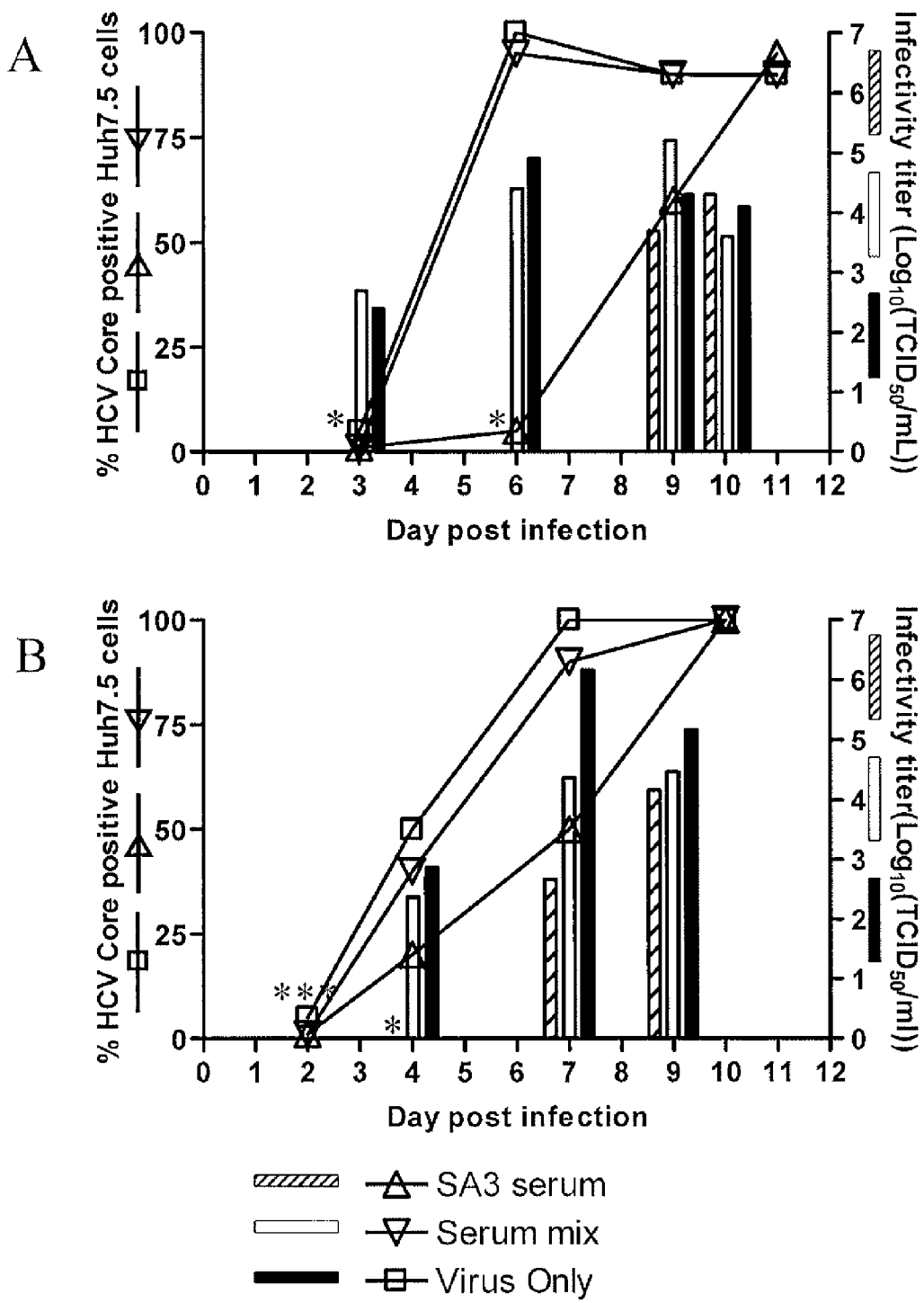

FIG. 13. Treatment of SA13/JFH1 infected Huh7.5 cells with 5a sera with high titers of neutralizing antibodies. SA13/JFH1 was pre-incubated with SA3 serum for 1 hour, before addition to Huh7.5 cells. Subsequently, the medium was replaced and supplemented with new SA3 serum every 24 hours and cells were split and stained for HCV Core antigen every 3 days. The serum control experiment was treated similarly, and an untreated virus control was also included. A. ~100 TCID$_{50}$ SA13/JFH1$_{C3405G\text{-}A3696G}$ (SEQ ID NO: 55) were pre-incubated with 1:200 dilution of SA3 serum or serum control before addition to 1.5×10$^5$ Huh7.5 cells/well. Percentage of infected cells was determined by Core antigen staining (left y-axis). Infectivity titers were determined singly, due to limited availability of supernatant, by a TCID$_{50}$ assay (right y-axis). B. ~50 TCID$_{50}$SA13/JFH1$_{C3405G\text{-}A3696G}$ (SEQ ID NO: 55) were pre-incubated with 1:50 dilution of SA3 serum or serum control before addition to 1×10$^5$ Huh7.5 cells/well; Percentage of infected cells (left y-axis) and TCID$_{50}$ titers (right y-axis) were determined as above. * <3 of 6 replicate wells infected by 1:10 dilutions (TCID$_{50}$/mL<10$^{1.7}$); undiluted supernatant could not be tested because of the limited amount of supernatant.

Figure 14:
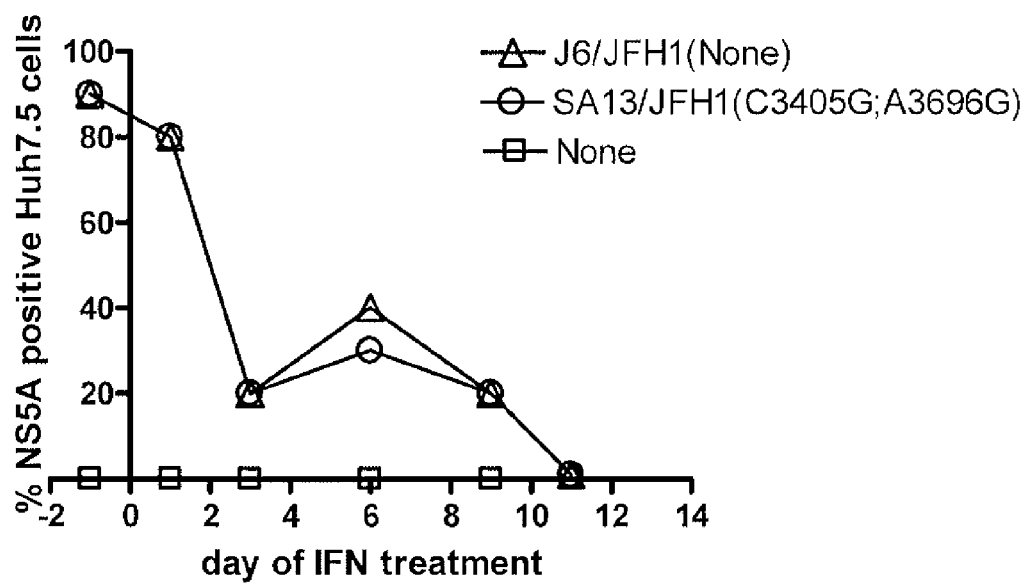

FIG. 14. Treatment of SA13/JFH1 infected cell cultures with interferon-α. INF-α treatment significantly reduces 5a/JFH1 infection of Huh7.5 cells. Huh7.5 cells were infected with SA13/JFH1$_{C3405G\text{-}A3696G}$ (SEQ ID NO: 55) (MOI 0.003). When 90% of the Huh7.5 cell culture were infected, the cells were treated with 500 IU/mL IFN-α applied 3 times within the first 24 hours, then daily up to day 4, afterwards every 1-2 days. Within the first 3 days of treatment, the percent infected cells decreased dramatically and were kept below 5% within 10 days.

DETAILED DESCRIPTION

The present invention advantageously provides hepatitis C virus (HCV) nucleotide sequences capable of replication, expression of functional HCV proteins, and infection in vivo and in vitro for development of antiviral therapeutics and diagnostics.

Nucleotide Acid Molecules (cDNA Clones and RNA Transcripts)

In a broad aspect, the present invention is directed to a genetically engineered hepatitis C virus (HCV) encoded by nucleic acid sequences such as a complementary DNA (cDNA) sequence and replicating RNA (SA13/JFH1) comprising the structural genes (Core, E1, E2), p7 and the non-structural gene NS2 of genotype 5a (e.g. strain SA13) and the non-structural genes NS3, NS4A, NS4B, NS5A and NS5B from the JFH1 strain (genotype 2a).

Thus in one embodiment, the present invention relates to a replicating RNA comprising the structural genes (Core, E1, E2), p7 and the non-structural gene NS2 of genotype 5a and the non-structural genes NS3, NS4A, NS4B, NS5A and NS5B from the JFH1 strain.

In another embodiment the genotype 5a is of the strain SA13.

In yet another embodiment the strain is SA13/JFH1

The invention provides an isolated nucleic acid molecule encoding an infectious recombinant HCV genome, which nucleic acid comprises an intergenotypic HCV genome. In one embodiment, the intergenotypic HCV genome comprises sequences encoding structural genes (Core, E1, E2), p7 and nonstructural genes (NS2) from a first HCV strain, and sequences encoding the 5' untranslated region (UTR), nonstructural genes NS3, NS4A, NS4B, NS5A, NS5B, and the 3' UTR from a second HCV strain.

In one embodiment, the first HCV strain and the second HCV strain are from different genotypes.

In one embodiment, the first HCV strain is strain SA13, and in another embodiment, the second HCV strain is strain JFH1.

In one embodiment, the HCV nucleic acid molecule of the present invention comprises the nucleic acid sequence (cDNA) of SA13/JFH1, SEQ ID NO: 1. In another embodiment the nucleic acid molecule has at least a functional portion of a sequence as shown in SEQ ID NO: 1 which represents a specific embodiment of the present invention exemplified herein.

In yet an embodiment the nucleic acid molecule comprises the nucleic acid sequence with a sequence identity of at least 90% to that of SEQ ID NO: 1.

In another embodiment, the nucleic acid comprises a sequence sharing at least 90% identity with that set forth in SEQ ID NO: 1, such as 90% identity, 91% identity, 92% identity, 93% identity, 94% identity, 95% identity, 96% identity, 97% identity, 98% identity, or 99% identity.

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

It should be noted that while SEQ ID NO: 1 is a DNA sequence, the present invention contemplates the corresponding RNA sequence, and DNA and RNA complementary sequences as well.

In a further embodiment, a region from an HCV isolate is substituted for a corresponding region, e.g., of an HCV nucleic acid having a sequence of SEQ ID NO: 1.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to SEQ ID NO: 1. Various modifications for example of the 5' and 3' UTR are also contemplated by the invention. In another embodiment, the nucleic acid further comprises a reporter gene, which, in one embodiment, is a gene encoding neomycin phosphotransferase, *Renilla luciferase*, secreted alkaline phosphatase (SEAP), *Gaussia luciferase* or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA. Thus, where particular sequences of nucleic acids of the invention are set forth, both DNA and corresponding RNA are intended, including positive and negative strands thereof.

In a further embodiment, the nucleic acid sequence of SEQ ID NO: 1 or the said nucleic acid sequence with any mutation described in this document is obtained by any other means than what is described above.

In another embodiment, the complementary DNA (cDNA) provided by the present invention encodes human hepatitis C virus of genotype 5a/JFH1, wherein said molecule is capable of expressing said virus when transfected into cells and further capable of infectivity in vivo and wherein said molecule encodes the amino acid sequence of SA13/JFH1, SEQ ID NO: 2.

According to various aspects of the invention, HCV nucleic acid, including the polyprotein coding region, can be mutated or engineered to produce variants or derivatives with, e.g., silent mutations, conservative mutations, etc. In a further preferred aspect, silent nucleotide changes in the polyprotein coding regions (i.e., variations of the first, second or third base of a codon leading to a new codon that encodes the same amino acid) are incorporated as markers of specific HCV clones.

Thus, one aspect of the present invention relates to any of the amino acid sequences disclosed herein, such as but not limited to SEQ ID NO: 2.

In yet an embodiment the isolated nucleic acid molecule encodes the amino acid sequence with a sequence identity of at least 90% to that of SEQ ID NO: 2.

In another embodiment, the amino acid sequences comprises a sequence sharing at least 90% identity with that set forth in SEQ ID NO: 3, such as 90% identity, 91% identity, 92% identity, 93% identity, 94% identity, 95% identity, 96% identity, 97% identity, 98% identity, or 99% identity.

It is to be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

In one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventors here report adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use, is characterized in that it contains one, several or all of the nucleic acid exchanges listed below and/or one or several or all of the following amino acid exchanges.

Figure 3:
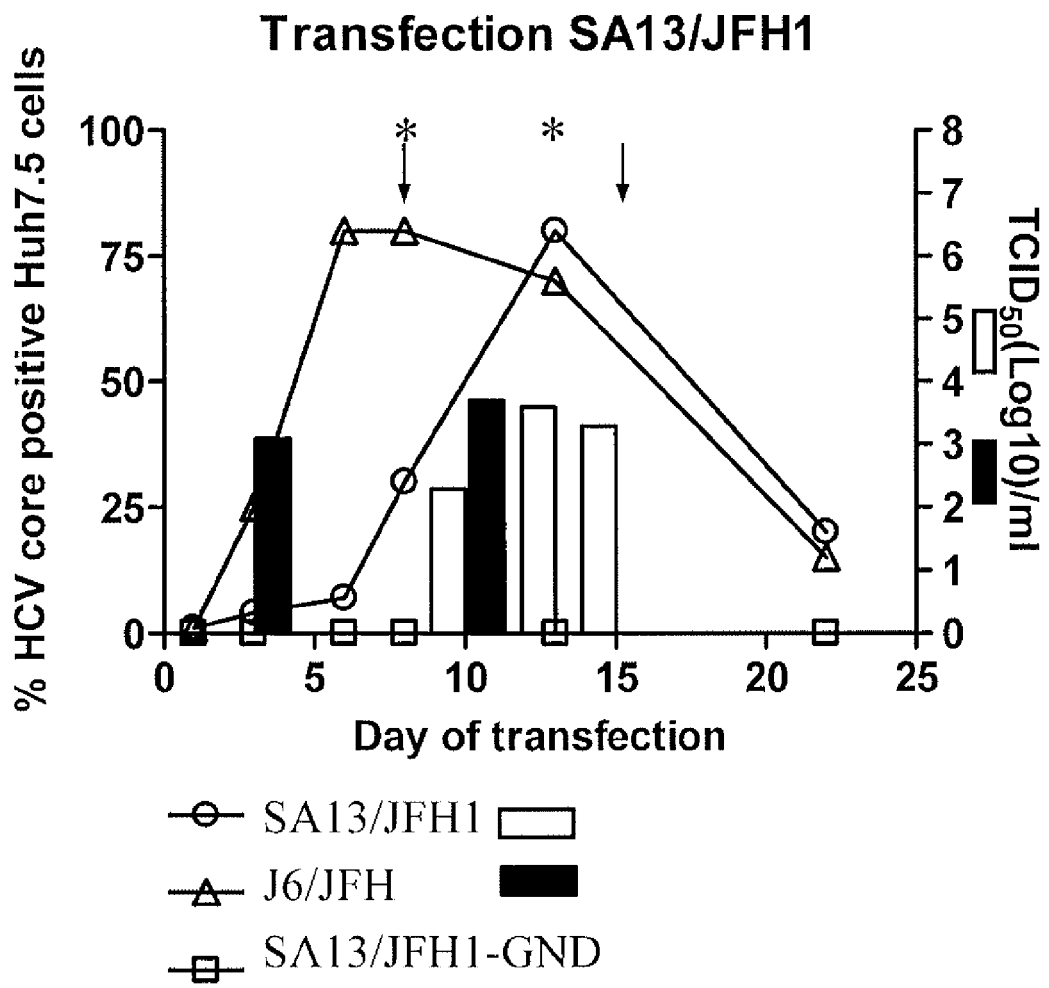
FIG. 3. Transfection of Huh7.5 cells with RNA transcripts of pSA13/JFH1 (SEQ ID NO: 1) and pFL-J6/JFH. Huh7.5 cells were transfected with 2.5 µg of RNA transcripts of pSA13/JFH1 (SEQ ID NO: 1), pFL-J6/JFH and the replication deficient pSA13/JFH1-GND. The percentage of infected cells (left y-axis) was determined as described in FIG. 8 and in Materials and Methods. Arrows indicate the time points, at which supernatants were collected used to inoculate naïve Huh7.5 cells in the 1st passage A. Stars show the time points, at which supernatant were collected used to inoculate naïve Huh7.5 cells in the 1st passage B. Day 8 supernatants were used for J6/JFH and SA13/JFH1-GND, day 13 and 15 supernatants were used for SA13/JFH1 for the two independent 1st passages (Table 7). Infectivity titers (TCID50; right y-axis) were determined by plating Huh7.5 cells at $6 \times 10^3$ cells/200 µl per well, in a polylysine coated Nunc 96 Well Optical Bottom Plate 24 hours before infecting them with 10-fold dilutions of supernatants as described in Material and Methods. The cells were washed, fixed and stained for NS5A, using anti-NS5A, 9E10, after 48-72 hrs. The cells were stained using HRP-conjugated 2° antibody and HRP substrate, diaminobenzidine (DAB). The wells were examined by light microscopy and wells with one or more positive cells were scored positive. Calculations of the TCID50 were done as described in Materials and Methods. TCID50 values are showed by white bars for SA13/JFH1 and black bars for J6/JFH.
Figure 4:
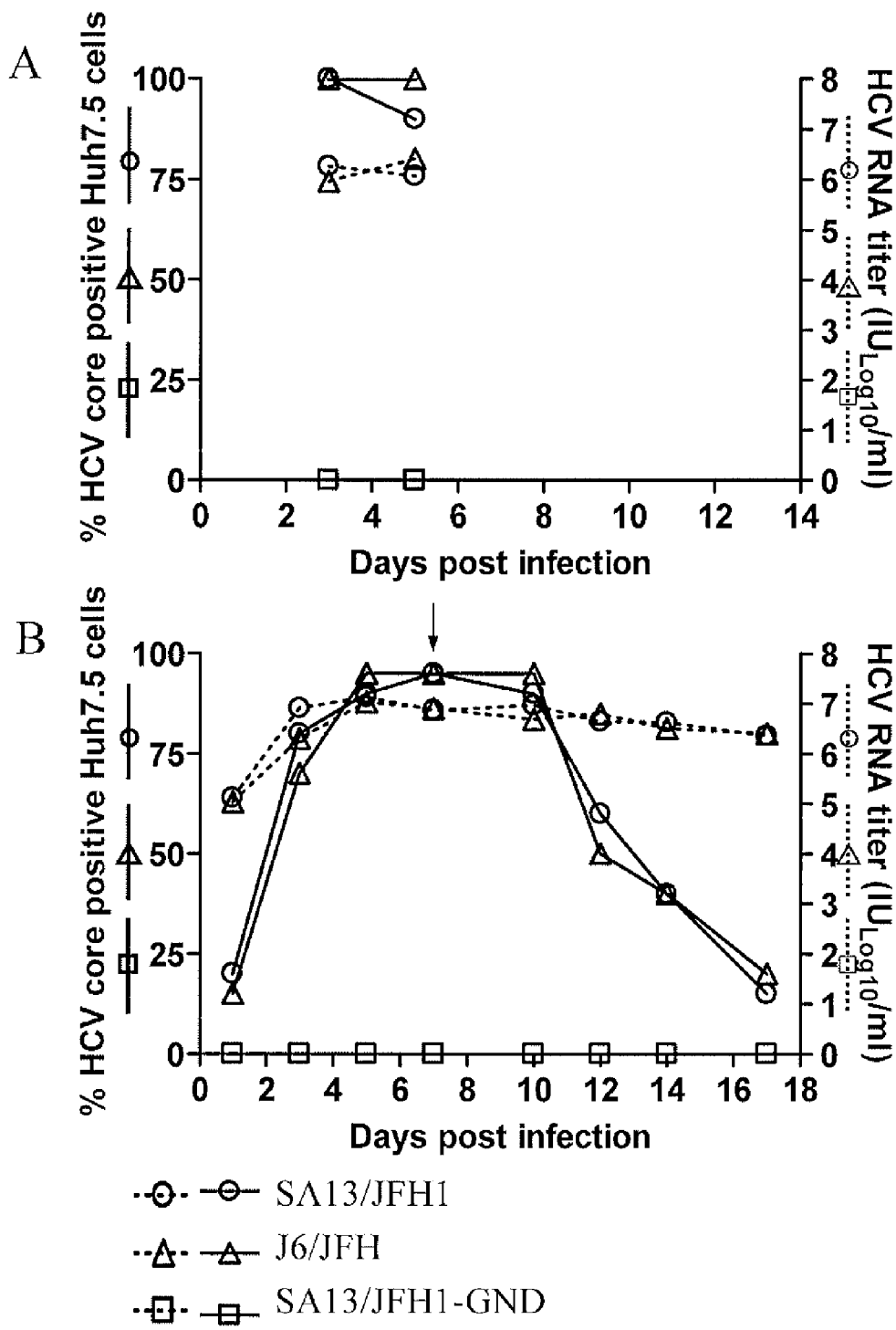
FIG. 4. 1st passage of SA13/JFH1 and J6/JFH viruses. Naïve Huh 7.5 cells were plated at $4 \times 10^5$ cells/well in a 6-well plate 24 hrs before cells were inoculated with sterile filtered supernatants from the transfection. The cells were split every 2-3 days and stained for Core and the percentage of infected cells were determined as described above (Left y-axis). HCV RNA titers were determined by the HCV TaqMan assay, an HCV specific RT-PCR assay with a 5'UTR primer pair and a fluorescent probe to quantify HCV RNA from cell culture supernatants as described in Materials and Methods. ND: not detected. A: The inocula were supernatants of a SA13/JFH1 culture from day 15 post-transfection and of a J6/JFH culture from day 8 post-transfection with an infectious dose of $10^{3.3}$ and $10^{3.1}$ TCID50 respectively. The negative control SA13/JFH1-GND was from day 8 post-transfection. The arrow shows the time point, at which supernatant of J6/JFH, SA13/JFH1 and SA13/JFH1-GND were used to inoculate naïve Huh 7.5 cells in the 2nd passage experiment (Table 7) B: The SA13/JFH1 inoculum was supernatant from day 13 post-transfection; its infectious dose was $10^{3.6}$ TCID50. The positive and the negative control, J6/JFH and SA13/JFH1-GND, respectively, were from day 8 post-transfection, as in experiment A. The arrow shows the supernatants of J6/JFH, SA13/JFH1 and SA13/JFH1-GND used to inoculate naïve Huh 7.5 cells in the 2nd passage experiment B (Table 7)

A delay in virus spread compared to the J6/JFH positive control culture occurred after transfection of SA13/JFH1 (genotype 5a/2a) RNA transcripts into Huh7.5 cells. This delayed increase in the percentage of SA13/JFH1 infected cells during the transfection experiment was mirrored by a delayed increase in infectivity titers (FIG. 3, 9 and table 6). During the 1st and 2nd viral passages (inoculated with the same dose of SA13/JFH1 and J6/JFH viruses), there was no difference in growth kinetics between the two cultures. In addition HCV RNA titers and infectivity titers were comparable at all time points analyzed (FIG. 4, 6 and table 6).

Accordingly, SA13/JFH1 might have acquired adaptive mutations during the transfection experiment, which rendered it as efficient as J6/JFH during the following passages. Thus 12 overlapping PCR products generated to span the entire ORF of SA13/JFH1 genomes recovered from 1st and 2nd passage cell culture supernatants were sequenced (Table 8).

1st passage virus pool mutation C3405G in NS2, resulting in an amino acid change, comprised the only mutation occurring in at least a 50:50 distribution together with the SA13/JFH1 sequence.

In the 2nd passage, the C3405G mutation appeared to dominate over the original sequence, and the non-coding mutations G2611T and A2728G in p7, and the coding mutation A3696G in NS3 had evolved from a minor quasispecies in the 1st passage to mutations occurring also at least as 50:50 distributions.

These results were reflected by clonal analysis (Table 8A and B), which was performed to investigate, how the different mutations observed were combined on the individual genomes. In 5 of 10 clones analyzed the present inventors found a combination of both non-coding nucleotide changes in p7 (G2611T and A2728G) and the coding nucleotide changes in NS2 (C3405G) and NS3 (A3696G). Four of 10 clones analyzed did not exhibit any of the mutations detected in direct sequence analysis thus indicating, that the original SA13/JFH1 genome might be viable, even though it might not be as efficient as the adapted genome. This finding is supported by the low infectivity titer measured on day 3 after transfection with SA13/JFH1 transcripts (Table 6).

In principle the detected mutations might enable efficient interaction between proteins of the different genotypes. Thus, the chimeric SA13/JFH1 NS2/NS3 autoprotease might require the mutations described for optimal function. This hypothesis is supported by the fact, that both amino acid changes, A1022G in NS2 and L1119R in NS3, are localized in the protease domain of the respective protein. On the other hand the described mutations might improve protein functions independent of intergenotypic interactions, for example by modulation of interactions with host cell proteins. Like this mutations in NS3 and NS5A, especially serine residues involved in hyperphosphorylation of NS5A, have been shown to play a major role for cell culture adaptation in the replicon system.

The crucial role of adaptive mutations for the viability of intergenotypic recombinant viruses has recently been found also by others. After transfection of intergenotypic 1a/2a (H77/JFH1) recombinants, a lag phase was observed following transfection before infectious viruses were produced yielding infectivity titers of $10^4$-$10^5$ FFU/ml. However, it is difficult to evaluate the performance of the 1a/2a recombinants, since the original non-adapted JFH1 genome was used as reference system, which has been shown to perform suboptimally in the absence of adaptive mutations.

The requirement for these adaptations was confirmed by reverse genetic studies. Thus, introducing these mutations, leading to constructs pSA13/JFH1-C3405G, pSA13/JFH1-C3405G-A3696G and pSA13/JFH1-G2611T-A2728G-C3405G-A3696G, (SEQ ID NO: 54, 55 and 56 with resulting amino acid sequences SEQ ID NO: 57, 58 and 59 respectively) led to immediate production of infectious viral particles after transfection in cell culture (FIG. 8, 9C and 10).

Furthermore, the present inventors demonstrate for the first time that HCV of genotype 5a utilizes CD81 and SR-BI for entry into host cells (further commented below).

One embodiment of the present invention relates to adaptive mutations, wherein the adaptive mutation is a mutation that can be observed by clonal or direct sequencing of recovered replicating genomes of SEQ ID NO: 1.

Thus in a further embodiment, the present invention relates to nucleic acid molecules according to the present invention, wherein said molecule comprises one or more adaptive mutations in p7, NS2 and NS3 singly or in combination.

In the context of the present invention the term "adaptive mutation" is meant to cover mutations identified in passaged SA13/JFH1 viruses that provide the original SA13/JFH1 genome and any other HCV sequence the ability to grow efficiently in culture. Furthermore all introductions of mutations into the SA13/JFH1 sequence described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins. This also includes other HCV genomes with adaptive mutations, all of them, combinations of them or individual mutations that grow in culture. In this case the titers might be lower than those listed.

It should be understood that any feature and/or aspect discussed above in connection with the mutations according to the invention apply by analogy to both single mutation and any combination of the mutations.

Three recombinant SA13/JFH1 genomes with mutations at nucleotide positions G2611T (p7), A2728G (p7), C3405G (NS2) and A3696G (NS3) were tested in Huh7.5 cells (FIG. 8, 9C and 10) and compared to the original SA13/JFH1 genome and J6/JFH. Mutation C3405G was tested alone (SEQ ID NO: 54), and in combination with A3696G (SEQ ID NO: 55). In addition all 4 mutations found in passaged SA13/JFH1 viruses were tested together (SEQ ID NO: 56). The first mutation that became dominant in the $1^{st}$ passages of SA13/JFH1 was C3405G, and thus the present inventors choose to test this mutation alone and in combination with other mutations. Only C3405G and A3696G caused amino acid changes (A1022G and K1119R respectively) and therefore they might have a more significant effect on adaptation. In a clonal analysis of SA13/JFH1 virus from a $2^{nd}$ passage, 5 out of 10 clones had all 4 mutations in combination. Huh7.5 cells were transfected with 2.5 µg of RNA transcripts of pSA13/JFH1, C3405G-SA13/JFH1, C3405G-A3696G-SA13/JFH1, G2611T-A2728G-C3405G-A3696G-SA13/JFH1, pFL-J6/JFH and pSA13/JFH1-GND.

As seen in the first transfection experiment with SA13/JFH1 (FIG. 3), there was a delay in the virus spread of SA13/JFH1 compared to the positive control J6/JFH1. To further illustrate the delay in viral spread of the original SA13/JFH1 genome in Huh7.5 cells compared to J6/JFH, additional infectivity titers (TCID$_{50}$) were made for three independent transfection experiments (FIGS. 9A, B and C). In all experiments similar transfection efficiencies based on percent infected cells for all genomes was shown, and in the transfection experiment in which the present inventors had collected culture supernatant at day 1 post-transfection (FIG. 9B), both SA13/JFH1 and J6/JFH had TCID$_{50}$ values below $10^1$ at day 1, however, the titer of the original SA13/JFH1 genome rose much slower than the corresponding titer of J6/JFH1 and the SA13/JFH1 mutated genomes. Furthermore, in all three transfection experiments, the present inventors found that during days 3 to 6 the TCID$_{50}$ titers were approximately 2-4 logs lower for the SA13/JFH1 genome compared to J6/JFH1

(FIGS. 9A, 9B and 9C) or SA13/JFH1 genomes with mutations (FIG. 9C), and the increase in infectivity titer over time was slower.

So even though the original sequence at adapted positions was found in four of ten clones derived from $2^{nd}$ passage viruses of the original SA13/JFH1 (Table 8A and B), suggesting that these particular mutations were not an absolute requirement for viability, the putative adaptive mutations introduced into the SA13/JFH1 construct in p7, NS2 and NS3 had a significant effect on the rate of infection in cell culture (FIGS. 8 and 10).

As seen in FIG. 8, SA13/JFH1 with the single mutation C3405G or in combination with other putative adaptive mutations spread as efficiently as the J6/JFH virus in Huh7.5 cells (FIGS. 8 and 9C).

Infectivity titers ($TCID_{50}$) were determined for SA13/JFH1, C3405G-SA13/JFH 1, C3405G-A3696G-SA13/JFH 1, G2611T-A2728G-C3405G-A3696G-SA13/JFH1 and FL-J6/JFH cultures on day 3 of the transfection experiment and were found to be $10^{2.2} TCID_{50}$/ml, $10^{3.9} TCID_{50}$/ml, $10^{4.1} TCID_{50}$/ml, $10^{4.3} TCID_{50}$/ml and $10^{4.1} TCID_{50}$/ml, respectively (Table 9). Hence, the mutations identified in direct sequencing and clonal analysis of the $2^{nd}$ passage SA13/JFH1 lead to adaptation and increase infectivity titers of the recombinant genomes compared to the original SA13/JFH1. One mutation in NS2, C3405G is sufficient for the virus to obtain titers comparable to J6/JFH.

In reverse genetic experiments it was found that SA13/JFH1 viruses with a combination of amino acid changes in NS2 (A1022G) and NS3 (K1119R), mapping to the NS2-3 autoprotease domain, were genetically stable and yielded infectivity titers of $\sim 10^5$ TCID50/mL in $1^{st}$ passage, slightly higher than titers observed in other JFH1-based intergenotypic recombinants. Amino acid changes in NS2 and NS3 are involved in cell culture adaptation of other JFH1-based intergenotypic recombinants, possibly facilitating the interaction between genotypes.

A 4a recombinant depended on mutations in NS2, while changes in NS3 conferred adaptation of 1a and 3a recombinants. Interestingly, I1313V in NS3, observed in one of the 1st passages of SA13/JFH1 (Table 8), was previously detected in a 1a/JFH1 recombinant. Introduction of this mutation had only a minor effect on the parental JFH1 strain, rather suggesting it to compensate for incompatibilities between gene sequences of different genotypes.

When sequencing HCV genomes from the supernatant of SA13/JFH1 infected cell cultures, the following changes at the nucleotide level were observed at least once; C3405G, G2611T, A2728G, A3696G, G2405A, C3623T, T3954C, A4277G, G4801A, G4801T, C4972T and C6538T.

These mutations caused the amino acid changes A1022G, R1095W, K1119R, V1205A, I1313V and Q1487H.

One embodiment of the present invention relates to adaptive mutations, wherein said adaptive mutation is at least one of the replacements of the first said nucleotide at the said position of SEQ ID NO: 1 by the following said nucleotide selected from the group consisting of C3405G, G2611T, A2728G, A3696G, G2405A, C3623T, T3954C, A4277G, G4801A, G4801T C4972T and C6538T.

One embodiment of the present invention relates to adaptive mutations, wherein said adaptive mutation is at least one of the replacements of the first said nucleotide at the said position of SEQ ID NO: 1 by the following said nucleotide selected from the group consisting of C3405G and A3696G.

One embodiment of the present invention relates to adaptive mutations, wherein said adaptive mutation is at least one of the replacements of the first said nucleotide at the said position of SEQ ID NO: 1 by the following said nucleotide selected from the group consisting of C3405G.

One embodiment of the present invention relates to adaptive mutations, wherein said adaptive mutation is a replacement of C in position 3405 of SEQ ID NO: 1 with G.

One embodiment of the present invention relates to adaptive mutations, wherein said adaptive mutation is a replacement of G in position 2611 of SEQ ID NO: 1 with T.

One embodiment of the present invention relates to adaptive mutations, wherein said adaptive mutation is a replacement of A in position 2728 of SEQ ID NO: 1 with G.

One embodiment of the present invention relates to adaptive mutations, wherein said adaptive mutation is a replacement of A in position 3696 of SEQ ID NO: 1 with G.

In another embodiment all the amino acid changes observed herein are provided by the present application. The skilled addressee can easily obtain the same amino acid change by mutating another base of the codon and hence all means of obtaining the given amino acid sequence is intended.

One embodiment of the present invention relates to adaptive mutations, wherein said adaptive mutation is at least one of the replacements of the first said nucleotide at the said position of SEQ ID NO: 2 by the following said amino acid selected from the group consisting of A1022G, R1095W, K1119R, V1205A, I1313V and Q1487H One embodiment of the present invention relates to adaptive mutations, wherein said adaptive mutation is at least one of the replacements of the first said nucleotide at the said position of SEQ ID NO: 2 by the following said amino acid selected from the group consisting of A1022G.

Another embodiment of the present invention relates said adaptive mutation is a replacement of K in position 1119 of SEQ ID NO: 2 with R.

Another embodiment of the present invention relates said adaptive mutation is a replacement of A in position 1022 of SEQ ID NO: 2 with G.

The skilled addressee may use the present invention to determine whether the identified sets of mutations can confer viability to other JFH1 based intergenotypic genotype 5a recombinants, which would allow in vitro studies of any patient 5a isolate of interest.

Finally, it would be interesting to elucidate the mechanism of action of the identified mutations. In principle they might enable efficient intergenotypic protein interaction and/or lead to improvement of protein function independent of these intergenotypic interactions, for example by influencing interactions with host cell proteins.

Titer

To determine the efficiency of the developed system, HCV RNA titers are determined in IU/ml (international units/ml) with Taq-Man Real-Time-PCR and infectious titers are determined with a tissue culture infectious dose-50 method. This titer shows the dilution of the examined viral stock, at which 50% of the replicate cell cultures used in the assay become infected and is given in $TCID_{50}$/ml.

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ $TCID_{50}$/ml or above following transfection and/or subsequent viral passage, such as a titer of at least $10^3$ TCID50/ml, such as a titer of at least $10^4$ $TCID_{50}$/ml, such as a titer of at least $10^5$ $TCID_{50}$/ml, such as a titer of at least $10^6$ $TCID_{50}$/ml, such as a titer of at least $10^7$ $TCID_{50}$/ml, such as a titer of at least $10^8$ $TCID_{50}$/ml, such as a titer of at least $10^9$ $TCID_{50}$/ml or such as a titer of at least $10^{10}$ $TCID_{50}$/ml.

It is of course evident to the skilled addressee that the titers described here is obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient, which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvmm*. Preferably, the adjuvant is pharmaceutically acceptable.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus in one embodiment the present invention relates to a method for producing a cell which replicates HCV 5a/JFH1 RNA and produces a virus particle comprising introducing the said RNA according to the invention into a cell.

In one embodiment the 5a strain is SA13.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein. Such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9 and the low-density lipid receptor.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Further the viability of the developed viruses may be determined in vivo, either in SCID-uPA mice engrafted with human liver tissue or in chimpanzees as shown in Lindenbach et al. 2006.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

Screening for Anti-Viral Drugs and the Determination of Drug Resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present study may prove useful for different research topics. Genomes with the original SA13 Core could be applied to examine genotype 5a specific features of Core.

The systems developed in this study are ideal candidates for the genotype 5a specific testing of therapeutics targeting viral entry, assembly and release.

Genomes with the SA13 sequence is valuable for testing of neutralizing antibodies and other drugs acting on entry level, such as fusion inhibitors.

The present inventors used SA13/JFH1 cultures to demonstrate that genotype 5a infection depended on CD81 and SR-BI, proving biological relevance of the system and confirming the importance of these co-receptors for HCV infection (FIGS. 11A & B).

The present inventors conducted cross-genotype neutralization studies in HCV cell culture systems recapitulating the entire viral life cycle using JFH1-based viruses with envelope sequences of all 6 major genotypes, which has previously not been possible. HCV E1/E2 assembled on HCV pseudo particles (HCVpp), used in previous neutralization studies could show an unphysiological confirmation, glycosylation pattern and/or lipoprotein association due to the nature of the HCVpp as well as the non-hepatic producer cell-lines used in such experiments. In such studies the viral particles are incubated with the neutralizing substance, e.g. patient derived antibodies present in serum, prior to incubation with cells permissive and susceptible to viral infection. The neutralizing effect, i.e. the inhibitory effect on viral entry, is measured e.g. by relating the number of focus forming units (FFUs, defined as foci of adjacent infected cells) to the equivalent count in a control experiment done under same circumstances without the active inhibitor molecule.

The inventors of the present invention showed that sera of patients chronically infected with genotype 5a, could neutralize the homologous SA13/JFH1 virus. Autologous SA13 patient serum, the source of the SA13 strain and two additional genotype 5a sera, SA1 and SA3 had relatively high titers of neutralizing antibodies against a homologous 5a/JFH1 virus (FIG. 12A and Table 10). Further, JFH1-based viruses of genotype 1a, 4a, and 6a were efficiently neutralized by the chronic phase SA1 serum derived from a South African hepatocellular carcinoma patient (Table 10). The SA3 and SA13 sera had limited or no cross-neutralization activity against genotype 1a and 4a viruses, but both sera had relatively high titers of neutralizing antibodies against the 6a virus. The 5a sera had no detectable cross-neutralizing activity against genotype 2a and 3a viruses at the 1:100 dilution (Table 10).

The results show a closer serological relationship between genotypes 1, 4, 5 and 6 as also seen in the pseudo-particle system, but they also show a genotype- and a strain-specific difference in the magnitude of this neutralization, thus demonstrating that it will be a challenge to develop vaccines that raises broadly reactive neutralizing antibodies.

Accordingly, the JFH1-based cell culture systems which has been developed for HCV genotype 1a/1b, 2a, 3a, 4a, 5a and 6a provides a valuable tool for efficiently screening for and identifying new candidate HCV genotype 1a/1b, 2a, 3a, 4a, 5a and 6a inhibitors e.g. of entry e.g. in serum derived from infected patients. Accordingly this invention, allows identification and raise of cross-neutralizing antibodies, which is important for the development of active and passive immunization strategies. Furthermore the availability of cell culture grown HCV particles bearing envelope proteins of the six major genotypes enables the development of inactivated whole virus vaccines and comprehensive virus neutralization studies.

The present inventors further used the SA13/JFH1 cultures to demonstrate specific neutralization with IgG purified from SA3 serum and chronic phase serum of genotype 1a patient H(H06). The inventors showed a dose dependent neutralization yielding a 97% inhibition with 40 μg of SA3 IgG and 98% inhibition with 40 μg H06 IgG (FIG. 12B).

Highly potent neutralizing antibodies are expected to be of importance for the development of anti-HCV immuno-therapies, applicable as post-exposure prophylaxis after needle stick injuries and as re-infection prophylaxis after liver transplantation of HCV infected patients, as well as for the development of an HCV vaccine.

Here the present inventors show that in vitro even low-dose viral infections could not be controlled by continuously treating SA13/JFH1 cultures with homologous neutralizing antibodies yielding efficient neutralization in an in vitro neutralization test. Because the present inventors were not able to achieve 100% neutralization in the neutralization assay (FIG. 12C), during the initial phase of treatment slow spread due to non-neutralized virus or alternatively cell-to-cell spread might occur. During the course of treatment viral titers might out-compete the applied dose of antibodies since relatively high infectivity titers were measured in the supernatant after a few days treatment (FIGS. 13A and B). The present inventors showed that neutralization efficiency depended on the viral dose (FIG. 12C), and in vivo rather high doses of neutralizing antibodies seemed to be required for protection.

Even though viral escape was described to occur in vivo, it is unlikely to be responsible for the observed treatment failure, since the present inventors could not detect amino acid changes in the envelope proteins of viruses recovered after the virus had spread to the entire culture. In line with these results, high titer neutralizing antibodies against the homologous virus were not always able to prevent HCV infection in uPA-SCID mice engrafted with human liver and these infections were shown to be due to neutralization failure and not viral escape.

Furthermore, JFH1 viruses have been reported to spread in vitro in the presence of neutralizing antibodies without employing obvious genetic escape mechanisms, because intracellular virus recovered after spread under neutralization pressure could still be neutralized with the same neutralizing antibodies as used for treatment. Identification of sera with higher neutralization titers, high titer IgG preparations or efficient monoclonal antibodies could perhaps permit more efficient treatment in vitro and in vivo.

In one embodiment the present invention relates to a method for identifying neutralizing antibodies.

In another embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

In one embodiment the present invention related to a method for screening new HCV genotype 1a/1b, 2a, 3a, 4a, 5a and/or 6a inhibitors or neutralizing antibodies, comprising:
  a. culturing at least one selected from the group consisting of a cell according to the present invention, a hepatitis C virus infected cell according to the present invention and a hepatitis C virus particle obtainable by the present invention together with a hepatitis C virus permissive cell,
  b. subjecting said virus or virus infected cell culture to a blood sample or derivatives thereof or synthetically produced equivalents from a HCV genotype 1a/1b, 2a, 3a, 4a, 5a and/or 6a infected patient, and
  c. detecting the amount of replicating RNA and/or the virus particles.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

As proof of principle of using the present invention in testing of anti-hepatitis C virus substances, the effects of interferon-α, currently used in combination therapy for HCV, were tested on the infected cell culture. As shown in FIG. 14, addition of interferon-α to a 5a/JFH1 infected culture immediately and significantly reduced the percentage of infected cells.

Thus, one embodiment of the present invention relates to a method for screening an anti-hepatitis C virus substance, comprising
  a) culturing at least one selected from the group consisting of a cell according to the present invention, a hepatitis C virus infected cell according to the present invention and a hepatitis C virus particle obtainable by the present invention together with a hepatitis C virus permissive cell, and
  b) detecting the replicating RNA and/or the virus particles in the resulting culture.

In another embodiment the present invention relates to a method for screening an anti-hepatitis C virus substance, comprising
  a) culturing at least one selected from the group consisting of a cell according to the present invention, a hepatitis C virus infected cell according to the present invention and a hepatitis C virus particle obtainable by the present invention together with a hepatitis C virus permissive cell,
  b) subjecting said virus or virus infected cell culture to the anti-hepatitis C virus substance, and
  c) detecting the replicating RNA and/or the virus particles in the resulting culture.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

In one embodiment, the term "antibody" refers to intact molecules as well as functional fragments thereof, such as Fab, $F(ab')_2$, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "$F(ab')_2$", refers to the fragment of the antibody that can be obtained by treating whole antibody with the enzyme pepsin without subsequent reduction, $F(ab')_2$ is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments, may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modeling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 nM to 25 µM, more preferably from about 0.0001 nM to 10 µM, and even more preferably from about 0.0001 nM to 1 µM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology shows a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew Tupaia belangeri chinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The genotype 5a cell culture system developed of the present invention will be a valuable tool to address different research topics. It will allow the genotype specific study of functions of the structural proteins (Core, E1, E2) as well as p7 and NS2 using reverse genetics. While the replicon systems facilitated testing of drugs interfering with replication such as NS3/4A protease and polymerase inhibitors, the system developed in this study is ideal for the genotype 5 specific testing of new drugs interfering with viral entry, such as fusion inhibitors, as well as assembly and release.

Accordingly the genotype 1a/1b, 2a, 3a, 4a, 5a and 6a developed cell culture system allows individual patient targeting. This means that when a new potential therapeutic candidate is discovered it is possible to test this particular candidate or combination of candidates on each of the individual genotypes. Knowing which specific genotype(s) the candidate is functioning towards, it allows an individual treatment of each patient dependent on which specific genotype the patient is infected with. Furthermore these cell culture systems allow the development of antibodies and vaccines targeting individual patients.

In addition new therapeutics targeting the putative p7 ion-channel and protease inhibitors targeting NS2 can be tested specifically for genotype 5 thus allowing individual patient targeting.

As SA13/JFH1 viability does not seem to depend on mutations in the envelope glycoproteins, these recombinant viruses will be well suited for screenings for broadly reactive neutralizing antibodies, thus aiding vaccine development.

The replication level of a virus can be determined, in other embodiments, using techniques known in the art, and in other embodiments, as exemplified herein. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaud et al., Virology 266 (2000) 180-188.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture. In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

Furthermore the invention also provide test kits, for screening for new HCV genotype 1a/1b, 2a, 3a, 4a, 5a and 6a inhibitors, neutralizing and cross neutralizing antibodies, comprising HCV virus components.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In addition, singular reference does not exclude a plurality. Thus, references to "a", "an", "first", "second" etc. do not preclude a plurality.

The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

The invention will hereinafter be described by way of the following non-limiting Figures and Examples.

Sequences

| SEQ ID | DNA/amino acid (AA) | Name |
|---|---|---|
| SEQ ID NO 1 | DNA | SA13/JFH1 |
| SEQ ID NO 2 | AA | SA13/JFH1 |
| SEQ ID NO 3 | DNA | SA13.1R901 |
| SEQ ID NO 4 | DNA | SA13seqR4524 |
| SEQ ID NO 5 | DNA | SA13R4745 |
| SEQ ID NO 6 | DNA | 9470R(24)_JFH1 |
| SEQ ID NO 7 | DNA | SA13R9488 |
| SEQ ID NO 8 | DNA | SA13R9824 |
| SEQ ID NO 9 | DNA | SA13F1 |
| SEQ ID NO 10 | DNA | SA13JFH1F341 |
| SEQ ID NO 11 | DNA | SA13JFH1 R1909 |
| SEQ ID NO 12 | DNA | SA13JFH1 F1827 |
| SEQ ID NO 13 | DNA | SA13JFH1 R3421 |
| SEQ ID NO 14 | DNA | SA13.2F2818 |
| SEQ ID NO 15 | DNA | SA13seqR3987 |
| SEQ ID NO 16 | DNA | SA13F3934 |
| SEQ ID NO 17 | DNA | SA13R9488 |
| SEQ ID NO 18 | DNA | SA13F9223 |
| SEQ ID NO 19 | DNA | SA13F9259 |
| SEQ ID NO 20 | DNA | SA13R9811 |
| SEQ ID NO 21 | DNA | −285S_HCV-MOD |
| SEQ ID NO 22 | DNA | −84S_HCV-MOD |
| SEQ ID NO 23 | DNA | SA13.1 seqR1443 |
| SEQ ID NO 24 | DNA | Chim seq F809 |
| SEQ ID NO 25 | DNA | SA13JFH1 R1987 |
| SEQ ID NO 26 | DNA | SA13 R2525 |
| SEQ ID NO 27 | DNA | SA13.2 seqF2327 |
| SEQ ID NO 28 | DNA | SA13 R3432 |
| SEQ ID NO 29 | DNA | SA13 F3246 |
| SEQ ID NO 30 | DNA | 4118R_JFH1 |
| SEQ ID NO 31 | DNA | 3880S_J6 |
| SEQ ID NO 32 | DNA | 4796R_JFH1 |
| SEQ ID NO 33 | DNA | 4528S_J6 |
| SEQ ID NO 34 | DNA | 5446R_JFH1 |
| SEQ ID NO 35 | DNA | 5272S_JFH1 |
| SEQ ID NO 36 | DNA | 6460R_J6 |
| SEQ ID NO 37 | DNA | 6186S_JFH1 |
| SEQ ID NO 38 | DNA | 7234R_JFH1 |
| SEQ ID NO 39 | DNA | 6862S_JFH1 |
| SEQ ID NO 40 | DNA | 7848R_JFH1 |
| SEQ ID NO 41 | DNA | 7741S_J6 |
| SEQ ID NO 42 | DNA | 8703R_JFH1 |
| SEQ ID NO 43 | DNA | 8137S_JFH1 |
| SEQ ID NO 44 | DNA | 9464R(24)_JFH1 |
| SEQ ID NO 45 | DNA | SA13JFH1 F11451 |
| SEQ ID NO 46 | DNA | SA13JFH1 R361 |
| SEQ ID NO 47 | DNA | SA13JFH1F341 |
| SEQ ID NO 48 | DNA | SA13JFH1 F3422 |
| SEQ ID NO 49 | DNA | SA13JFH1 R4141 |
| SEQ ID NO 50 | DNA | ppSA13F823 |
| SEQ ID NO 51 | DNA | ppSA13R1915 |
| SEQ ID NO 52 | DNA | SA13F3380-3405G |
| SEQ ID NO 53 | DNA | SA13R3430-3405G |
| SEQ ID NO 54 | DNA | pSA13/JFH1-C3405G |
| SEQ ID NO 55 | DNA | pSA13/JFH1-C3405G-A3696G |
| SEQ ID NO 56 | DNA | pSA13/JFH1-G2611T-A2728G-C3405G-A3696G |
| SEQ ID NO 57 | AA | pSA13/JFH1-C3405G |
| SEQ ID NO 58 | AA | pSA13/JFH1-C3405G-A3696G |
| SEQ ID NO 59 | AA | pSA13/JFH1-G2611T-A2728G-C3405G-A3696G |
| SEQ ID NO 60 | DNA | SA13muta A3696G R |
| SEQ ID NO 61 | DNA | SA13muta A3696G F |
| SEQ ID NO 62 | DNA | SA13muta G2611T R |
| SEQ ID NO 63 | DNA | SA13muta G2611T F |
| SEQ ID NO 64 | DNA | SA13muta A2728G R |
| SEQ ID NO 65 | DNA | SA13muta A2728G F |

EXAMPLES

Materials and Methods

Source of HCV Genotype 5a.

Plasma pooled from plasmapheresis units of a chimpanzee infected with hepatitis C virus strain SA13 was used to amplify and clone the genotype 5a genome. The chimpanzee was inoculated intravenously with serum from a hepatocellular carcinoma patient from South Africa. The genotype 5a plasma pool had an HCV RNA titer of ~$10^5$ IU/ml and an infectious titer of ~$10^4$ chimpanzee infectious doses/ml. The near full-length consensus genome sequence of HCV viruses recovered from this pool was reported previously.

RNA Extraction for Amplification of SA13 HCV RNA.

RNA from 100 µl aliquots of chimpanzee plasma was extracted with TRIZOL Reagent (Invitrogen). After 5 min incubation with 1000 TRIZOL, 2000 chloroform was added and the solution was mixed thoroughly and incubated for 3 min. Finally, the two-phase solution was centrifuged. The aqueous phase containing RNA was mixed with glycogen, an RNA carrier, and precipitated with isopropanol by centrifugation. The pellet was washed with ice-cold 70% ethanol, dried and resuspended in 10 µl solution containing 8.5 µl nuclease free water (Promega), 1 µl DTT (100 mM, Promega), and 0.5 µl RNasin (20-40 units/µl, Promega). The extracted RNA was used immediately for cDNA synthesis with primers SA13.1R901, SA13seq4524 or SA13R9488 (SEQ ID NO: 3, 4 and 7). All primers in the present study were from TAG Copenhagen.

In another extraction procedure, RNA from 200 µl aliquots of chimpanzee plasma was extracted with High Pure Viral Nucleic Acid Kit (Roche) using the manufacturers' protocol. In this extraction method nucleic acids are bound to glass fibers of spin columns and are washed to remove impurities. The RNA extracted with the kit was eluted in 22 µl of elution buffer, and used immediately in reverse transcription (RT) reactions with primers SA13R4745 or SA13R9824 (SEQ ID NO: 5 and 8).

cDNA Synthesis from SA13 HCV RNA.

RNA extracted from 100 µl plasma was subjected to RT-PCR using specific primers, as showed in the text below for each individual fragment. 9 µl RNA eluate was incubated with 2.5 µl primer (10 mM) and 10 dNTP mix (10 mM, Invitrogen) at 65° C. for 2 min and chilled on ice. After addition of 2 µl Superscript III (200 units/µl, Invitrogen), 4 µl 5x first strand buffer (Invitrogen), 0.5 µl RNasin (20-40 units/µ) and 10 DTT (100 mM) the reaction was incubated at 50° C. for 40-60 min and 55° C. for 30-60 min. The reaction was inactivated at 70° C. for 15 min, and the sample was treated with 1 µl RNaseH (4 units/µl, Invitrogen) and 10 RNAseT1 (1000 units/µl, Ambion) for 20 min at 37° C. to remove the RNA templates. The cDNA was used immediately or stored at −20° C.

All cDNA was made with Superscript III except for the 5'UTR fragment, where the 100 RNA solution was heated to 65° C. for 2 min, chilled on ice and mixed with 1 µl AMV Reverse Transcriptase (20 units/ul, Amersham), 2 µl AmpliTaq Gold 10x buffer (Applied Biosystems), 2 µl $MgCl_2$ (25 mM, Applied Biosystems), 3 µl reverse primer (10 mM), 2 µl dNTP mix (10 mM) and 0.5 µl RNasin (20-40 units/µ). The solution was incubated for 60 min at 42° C. and chilled on ice.

PCR Amplification for Determination of the SA13 Consensus Sequence.

To amplify PCR fragments from cDNA, BD Advantage 2 Polymerase Mix (Clontech) or AmpliTaq Gold DNA Polymerase (Applied Biosystems) were used as directed in the manufacturers 'descriptions. A standard reagent protocol for Advantage 2 Polymerase Mix was used if no alternative protocol is mentioned, in which the present inventors combined 5 µl 10x buffer, 1.3 µl dNTP mix (10 mM), 1 µl forward primer (10 mM), 1 µl reverse primer (10 mM), 1 µl BD Advantage 2 Polymerase Mix (50x), 2.5 µl cDNA and 38.2 µl $H_2O$ for a total volume of 50 µl in PCR tubes on ice. Cycling parameters are described below for the individual fragments. All PCR fragments were analyzed on 1% agarose gels and purified using Wizard SV gel and PCR Clean-Up System (Promega).

Depending on size amplicons were subcloned into either pCR2.1 TOPO or pCR-XL-TOPO vectors (Invitrogen) as specified below, following the TOPO-cloning kit protocol and using TOP10 (Invitrogen) or DH5α (Invitrogen) chemically competent bacteria grown on agar plates at 37° C. overnight. Single bacteria colonies were inoculated into Luria-Bertani (LB) medium (GIBCO, Invitrogen) with selective antibiotics and grown at 37° C. overnight. Plasmids were purified from bacteria cultures with the QIAprep Spin Miniprep Kit (Qiagen). For each subcloned PCR amplicon 3-12 clones were sequenced (Macrogen Inc., Seoul, South Korea). Sequence analysis was performed and the SA13 sequences were determined using Sequencher 4.6, Gene Codes Corporation.

The Following 6 Amplicons Were Obtained:

Fragment 1 from nucleotide 1 to 909 (nucleotide positions refer to full-length SA13): Following cDNA synthesis with AMV Reverse Transcriptase and reverse primer SA13.1R901 (SEQ ID NO: 3). PCR amplification was performed using 20.5 µl cDNA and adding 56.5 µl nuclease free water (Promega) before heating the solution to 95° C. for 5 min. Subsequently 0.5 µl AmpliTaq Gold (5 units/µl, Applied Biosystems), 8 µl AmpliTaq Gold 10x buffer, 8 µl $MgCl_2$ (25 mM, Applied Biosystems) 5 µl forward primer SA13F1 (10 mM) and 2 µl reverse primer SA13.1R901 (10 mM) (SEQ ID NO: 9 and 3) were mixed with the RNA solution. The forward primer had a 5' overhang containing a NotI restriction site, a T7 promoter and an initial G, in order to facilitate the development of a full-length SA13 cDNA clone for future studies. The cycle parameters were 12 min at 94° C. to heat activate the polymerase and 35 cycles of 1 min denaturation at 94° C., 2 min annealing at 45° C. and 3 min of elongation at 72° C. The PCR fragments were subcloned into pCR2.1 TOPO and 5 clones were sequenced.

Fragment 2 from nucleotide 341-1901: Following RT with Superscript III and specific primer SA13R4745 (SEQ ID NO: 5) amplification was performed by nested PCR with Advantage 2 Polymerase Mix. A $1^{st}$ round PCR with forward primer SA13F1 and reverse primer SA13R4745 (SEQ ID NO: 9 and 5) was performed as described above and run with the following cycle parameters: initial denaturation 1 min at 95° C.; 45 cycles of 30 s at 95° C., 30 s at 45° C. and 9 min at 68° C.; final elongation of 10 min at 68° C. The forward primer SA13JFH1F341 and reverse primer SA13seqR1909 (SEQ ID NO: 10 and 11) were used in the $2^{nd}$ round of PCR, in which 2.5 µl of $1^{st}$ round PCR product was added to the reaction master mix. The cycle parameters for the $2^{nd}$ round PCR were modified because of the smaller fragment and were 1 min at 95° C. and 20 cycles of 30 s at 95° C., 30 s at 45° C., 3 min at 68° C., followed by a final step of 10 min at 68° C. The fragment was subcloned into pCR2.1 TOPO and 5 clones were sequenced.

Fragment 3 from nucleotide 1827-3421: The cDNA was obtained with Superscript III and specific primer SA13seq4524 and the fragment was amplified with Advantage 2 Polymerase Mix using forward primer SA13JFH1F1827 and reverse primer SA13JFH1R3421 (SEQ ID NO: 4, 12 and 13). The PCR cycle parameters were 1 min at 95° C. and 40 cycles of 30 s at 95° C., 30 s at 67° C., 3 min at 68° C., followed by 10 min at 68° C. The fragment was subcloned into pCR2.1 TOPO and 5 clones were sequenced.

Fragment 4 from nucleotide 2818-3987: Following cDNA synthesis with Superscript III and specific primer SA13R4745 (SEQ ID NO: 5), the amplicon was generated by nested PCR with Advantage 2 Polymerase Mix. A $1^{st}$ round PCR with forward primer SA13F1 and reverse primer SA13R4745 (SEQ ID NO: 9 and 5) was carried out as above for fragment 2. For the $2^{nd}$ round PCR with 2.5 µl of the $1^{st}$ PCR product, forward primer SA13F2818 and reverse primer SA13seqR3987 (SEQ ID NO: 14 and 15) the same cycle parameters as for the $2^{nd}$ round PCR of fragment 2 were used (see above). The fragment obtained was subcloned into pCR2.1 TOPO and 5 clones were sequenced.

Fragment 5 from nucleotide 3934-9488: RT was performed with Superscript III and SA13R9488 (SEQ ID NO: 17), and the fragment was amplified from cDNA using Advantage 2 Polymerase Mix, forward primer SA13F3934 and reverse primer SA13R9488 (SEQ ID NO: 16 and 17). The forward and reverse primer introduced overhangs with a NotI and NsiI restriction site, respectively. Both sites were introduced as part of a strategy to create of a full-length cDNA clone. The PCR amplification parameters were as follows: 1 min at 95° C., 35 cycles of 30 s at 95° C., 30 s at 59° C., 9 min at 68° C., followed by 10 min at 68° C. The fragment was subcloned into pCR-XL-TOPO and 3 clones were sequenced.

Fragment 6 from nucleotide 9196-9511: Following cDNA synthesis with Superscript III and the reverse primer SA13R9824 (SEQ ID NO: 8), the fragment was amplified with nested PCR using AmpliTaq Gold. The reaction included 5 µl of 10× buffer, 1.3 µl dNTP mix (10 mM), 2 µl of each primer (10 mM), 1 µl AmpliTaq (5 units/µl), 4 µl MgCl$_2$ (25 mM), 2.5 µl cDNA (for $1^{st}$ round PCR), or 5 µl of the $1^{st}$ round PCR product (for $2^{nd}$ round PCR), and H$_2$O to a total volume of 50 µl. The 1st round PCR was performed with primers SA13F9223 and primer SA13R9824 (SEQ ID NO 18 and 8). The internal primer pair for $2^{nd}$ round PCR was SA13F9259 and SA13R9811 (Table 1) (SEQ ID NO: 19 and 20). For both PCR reactions the cycle parameters were as follows: 10 min at 95° C. and 35 cycles of 1 min at 94° C., 2 min at 60° C., 3 min at 72° C., followed by 10 min at 72° C. The fragment was subcloned into pCR2.1-TOPO and 12 clones were sequenced.

Construction of pSA13/JFH1.

The full-length SA13/JFH1 recombinant (SEQ ID NO: 1) was constructed using the SA13 sequence fragments containing the structural genes (Core, E1, E2), p7 and NS2. The nonstructural genes NS3, NS4A, NS4B, NS5A and NS5B and the 5' and 3'UTR of JFH1 were amplified from pFL-J6/JFH, which included a T7 promoter upstream of the 5'UTR and an XbaI site downstream of the 3'UTR to linearize the plasmid before in vitro transcription. Cloned Pfu DNA polymerase (Stratagene), was always used in amplification of fragments from plasmids and in fusion PCRs due to its high proofreading capacity. The standard reagent protocol for the amplification of fusion fragments included 0.5 µl of the Pfu DNA polymerase (2.5 U/µl), 5 µl 10× cloned Pfu buffer, 1 µl dNTP (10 mM), 1 µl of forward (10 mM) and reverse (10 mM) primers, 100 ng of pCR2.1 TOPO containing the subcloned SA13 fragments or 10 ng of pFL-J6/JFH and H$_2$O to a final volume of 50 µl. In the subsequent fusion PCR the same reagent protocol was followed but 100 ng of each fragment was used.

A consensus sequence of SA13 nucleotide 1827-3421 in pCR2.1 TOPO was created by using the previously generated clones of fragment 3 and employing standard restriction digest (all enzymes purchased from NEB) and ligation (Rapid DNA Ligation Kit, Roche) procedures. This plasmid containing SA13 consensus sequence (nucleotides 1827-3421) was designated SA13.2cons cl.2.

The fusion fragments of the SA13 portion of SA13/JFH1 were amplified from one of the fragment 1 clones of pCR2.1 TOPO containing SA13 nucleotides 1 to 909 (see above) with primers SA13JFH1F341 and SA13.1R901 (SEQ ID NO: 10 and 3), from the consensus clone SA13.2cons cl.2 of fragment 3 (see above) with primers SA13JFH1F1827 and SA13JFH1R3421 (SEQ ID NO: 12 and 13) and from pCMV-SA13 with primers ppSA13F823 and ppSA13R1915 (SEQ ID NO: 50 and 51). The PCR cycle parameters for all three reactions were as follows: 45 s at 95° C., 20 cycles of 45 s at 95° C., 45 s at 60° C., 3 min at 72° C., followed by 10 min at 72° C.

The 5' end of JFH1 was amplified from pFL-J6/JFH, using forward primer SA13JFH1F11451 (Table 4, which is in the vector part to include the restriction site XmnI, and reverse primer SA13JFH1R361 (SEQ ID NO: 45 and 46), which anneals at the junction between 5'UTR and core and has an overhang consisting of the first 21 nucleotides of SA13 core region to enable fusion. The PCR cycle parameters were 45 s at 95° C., 20 cycles of 45 s at 95° C., 45 s at 63° C., 1 min at 72° C., followed by 10 min at 72° C. The JFH1 fragment immediately downstream of the NS2/NS3 junction was amplified from pFL-J6/JFH, using the forward primer SA13JFH1F3422 (SEQ ID NO: 48) (Table 4), which had an overhang consisting of the last 27 nucleotides of SA13 NS2, and reverse primer SA13JFH1R4141 (SEQ ID NO 49) which is downstream of the restriction site SpeI in JFH1 NS3. The PCR cycle parameters for this fusion fragment were as follows: 45 s at 95° C., 20 cycles of 45 s at 95° C., 45 s at 61° C., 1 min at 72° C., followed by 10 min at 72° C.

A 5-piece fusion fragment of SA13 and JFH1 was amplified by using approximately 100 ng of each of the fragments described and a PCR protocol of 45 s at 95° C. and 20 cycles of 45 s at 95° C., 45 s at 45° C., 10 min at 72° C., followed by 10 min at 72° C. with primers SA13JFH1F11451 and SA13JFH1R4141 (SEQ ID NO: 45 and 49) (Table 4). The 5-piece fusion product was cloned into pCR-XL-TOPO and the entire HCV sequence of 3 clones was sequenced to verify correct fusion.

The TOPO cloned fusion product (pCR-XL-Fusion) and pFL-J6/JFH were digested with XmnI (NEB), which cuts in the pFL-J6-JFH1 vector sequence upstream of the 5'UTR and SpeI (NEB), which cuts in NS3 of JFH1. The 7447 bp fragment of pFL-J6/JFH was dephosphorylated and religated with the 4916 bp SA13/JFH1 fragment. The final construct was transformed into TOP10 bacteria. The HCV sequence of the described plasmid was verified by sequencing of the final DNA preparation (EndoFree Plasmid Maxi Kit, Qiagen).

Construction of pSA13/JFH1-GND.

In order to generate the replication defective SA13/JFH1-GND genome, the plasmid pFL-J6/JFH(GND) and the pCR-XL-fusion were digested with XmnI and SpeI as described above. The 7447 bp fragment of pFL-J6/JFH-GND was dephosphorylated and religated with the 4916 bp fusion fragment containing the chimeric junctions and SA13 Core through NS2. The construct was amplified in TOP10 bacteria.

Generation of In Vitro Transcripts.

Before in vitro transcription, 12 ug of each plasmid (pSA13/JFH1 (SEQ ID NO: 1), pFL-J6/JFH and negative controls pSA13/JFH1-GND, pFL-J6/JFH(GND)) was linearized by XbaI (NEB) following the manufacturers' guidelines, and agarose gel purified. The linearized plasmids were treated with Mung Bean Nuclease (NEB) as described by the manufacturer, to remove the single stranded overhang from the artificial XbaI site, which would result in extra nucleotides on the transcribed RNA strand, the reaction was inactivated and purified with Wizard SV gel and PCR Clean-Up System. Approximately 5 µg of the linearized plasmids were in vitro transcribed by T7 RNA Polymerase (Promega) at 37° C. for 2 hours; the reaction mix contained 20 µl of the 5× buffer, 10 µl of DTT (100 mM, Promega), 2.5 µl RNasin (20-40 units/µl, Promega), 20 µl rNTP mix (2.5 mM each, Promega), 2 µl of the T7 polymerase (20 U/µl) and $H_2O$ to a final volume of 100 µl. To estimate the amount of RNA 2 µl of RNA transcripts were run on an agarose gel.

Cell Culture.

Human hepatoma cells, Huh 7.5 were kept in the following culture medium: Dulbecco's modified eagle medium, DMEM (Gibco) 4500 mg/L Glucose, GlutaMAX™ I, Pyruvate (Gibco/Invitrogen Corporation), supplemented with 10% heat inactivated fetal bovine serum (FBS, Sigma), 1% Penicillin/Streptomycin (100 U/ml penicillin, 100 mg/ml streptomycin, Gibco/Invitrogen Corporation), which is referred to as complete medium hereafter. Cells were cultured at 37° C., in 90% humidity and 5% $CO_2$. Cells were split at confluence, every 2-3 days, in ratios of 1:2 or 1:3. The cells were washed with PBS (Dulbecco's Phosphate Buffered Saline, Sigma) before they were trypsinized with Trypsin/EDTA (Gibco/Invitrogen Corporation), resuspended in complete medium and centrifuged at 1000 rpm for 5 min. Cells were resuspended, split and kept in 10 ml complete medium in T75 flasks (Nunc).

Transfections.

Transfection of in vitro transcribed RNA was performed using a liposome method, with Lipofectamine 2000 (Invitrogen). Huh 7.5 were washed with PBS before they were trypsinized and plated out 24 hrs prior to transfection, to obtain 80-90% confluence at transfection. $7 \times 10^5$ cells/well in 2 ml DMEM without antibiotics were seeded in 6-well plates (Nunc). 5 µl Lipofectamine-2000 and 2.5 µg RNA transcripts were each diluted in 250 µl Opti-MEM (Invitrogen) combined and incubated at room temperature for 20 min for formation of transfection complexes. 500 µl of the RNA/Lipofectamine transformation complexes were added to each of the wells containing 2 ml DMEM, and incubated under usual growth conditions. The medium was changed to complete medium after 12-24 hrs.

Detailed Methods for Reverse Genetics Experiment.

Huh7.5 cells were plated in 6-well plates with $4 \times 10^5$ cells/well 24 hrs before cells were transfected. Huh7.5 cells were transfected with 2.5 µg of RNA transcripts of pSA13/JFH1 (SEQ ID NO: 1), C3405G-SA13/JFH1 (SEQ ID NO: 54), C3405G-A3696G-SA13/JFH1 (SEQ ID NO: 55), G2611T-A2728G-C3405G-A3696G-SA13/JFH1 (SEQ ID NO: 56), pFL-J6/JFH and the replication deficient pSA13/JFH1-GND with Lipofectamine 2000.

The cells were split every 2-3 days and the percentage of infected cells was evaluated by staining for HCV Core protein. 24 hrs before the staining, the cells were trypsinized and plated in 8 chamber slides with $0.5 \times 10^5$ cells/300 µl and grown overnight. After the cells were fixed, intracellular staining was performed with primary antibody (Murine Anti-Human HCV Core Protein Clone B2 (MAB, Anogen)) in PBS/5% BSA. The slides were washed with PBS and PBS/0.1% Tween, and incubated with secondary antibody, Alexa Fluor 594-conjugated goat-anti mouse IgG in PBS/0.1% Tween. Cell nuclei were stained with Hoechst dye. The slides were washed and mounted with Fluoromount-G and cover glass. Slides were evaluated for percentage of infected cells by examination with a Leica confocal fluorescence microscope.

Infectivity titers ($TCID_{50}$) were determined for SA13/JFH1 (SEQ ID NO: 1), C3405G-SA13/JFH1 (SEQ ID NO: 54), C3405G-A3696G-SA13/JFH1 (SEQ ID NO: 55), G2611T-A2728G-C3405G-A3696G-SA13/JFH1 (SEQ ID NO: 56) and FL-J6/JFH on day 3.

Infectivity titers ($TCID_{50}$) were determined by plating Huh7.5 cells at $6 \times 10^3$ cells/200 µl per well, in a polylysine coated Nunc 96 Well Optical Bottom Plate 24 hours before infecting them with 10-fold dilutions of supernatants in 6 replicates. The cells were washed, fixed and stained for NS5A, using anti-NS5A, 9E10, after 48 hrs. The cells were stained using HRP-conjugated 2° antibody and HRP substrate, diaminobenzidine (DAB). The wells were examined by light microscopy and wells with one or more positive cells were scored positive. Calculations of the $TCID_{50}$ were done as described in the below.

Collection of Supernatants for Titration and Passage of Virus.

Cell supernatants were saved every 2-3 days when the cells were split. The supernatants were sterile filtered with 0.20-0.45 µm filters (Minisart, Sartorius), aliquoted in cryotubes (Nunc) and stored at −80° C. The filtration served to remove cells so only virus from the supernatant was passed.

Immunofluorescence (indirect) staining for HCV Core antigen. The day before the staining the cells were washed with PBS, trypsinized and plated out in complete medium, in (8 chamber slide with $0.5 \times 10^5$ cells (300 µl)/well or 4 chamber slides with $1.5 \times 10^5$ cells (600 µl)/well, Nunc) and incubated overnight at 37° C., in 90% humidity and 5% $CO_2$. The cells were washed twice with PBS, fixed and permabilized with ice-cold acetone for 5 min. The grid was removed and the slide washed twice with PBS and once with PBS/0.1% Tween. Intracellular staining was performed with primary antibody, Murine Anti-Human HCV Core Protein Clone B2 (MAB, Anogen), at a dilution of 1:200 in PBS/5% BSA and incubated for 20 min. The slides were washed twice with PBS and once with PBS/0.1% Tween, and incubated with secondary antibody, Alexa Fluor 594-conjugated goat-anti mouse IgG (Invitrogen), in a 1:1000 dilution in PBS/0.1% Tween for 5 min. Cell nuclei were stained with Hoechst dye (Molecular Probes) at 1:10.000 dilution for 5 min. The slides were washed twice with PBS and mounted with Fluoromount-G (Southern Biotech) and cover glass. Slides were evaluated for percent infectivity with Leica confocal fluorescence microscope. The day of % infection refers to the day the cells were plated on the slides.

Passage of Virus to Naïve Huh7.5 Cells.

Cells were washed with PBS, trypsinized and plated out in a 6 well plate with $4 \times 10^5$ cells/well. 24 hours later medium was removed and the cells were washed with PBS, and 1 ml supernatant from infected cells was added to the cells with 1 ml of complete medium. The cells were incubated at 37° C., in 90% humidity and 5% $CO_2$ for 4-5 hours, and then the medium was removed and replaced by complete medium. Cells were passed every 2-3 days and the supernatants were saved.

Generation of PCR Products for Direct Sequencing of the ORF of SA13/JFH1 Cell Culture Supernatant Derived Viruses.

RNA from 200 µl cell culture supernatant was extracted with High Pure Viral Nucleic Acid Kit (Roche) using the manufacturers protocol. RT was performed with Superscript III and the gene specific primer 9470R_JFH1 (SEQ ID NO: 6) on RNA from 100 µl cell culture supernatant with reagents as described above for 1 hour at 50° C., followed by inactivation at 70° C. for 15 min, and treatment with 1 μl RNaseH (4 U) and 1 μl RNaseT1 (1000 U) for 20 min at 37° C. To sequence the entire ORF, the 1st round PCR produced a long fragment from nucleotide 56 to 9476 and the $2^{nd}$ round PCR produced 12 overlapping fragments spanning nucleotide 257-9469. The $1^{st}$ round PCR procedure was performed with Advantage 2 Polymerase Mix, specific primers-285S_HCV-MOD and 9470R_JFH1 (SEQ ID NO: 21 and 6) following the standard protocol. The PCR cycle parameters were modified with an increasing number of cycles and elongation time, and were as follows: 4 cycles of 35 s at 99° C., 30 s at 67° C., 10 min at 68° C.; 9 cycles of 35 s at 99° C., 30 s at 67° C., 11 min at 68° C.; 9 cycles of 35 s at 99° C., 30 s at 67° C., 12 min at 68° C.; 9 cycles of 35 s at 99° C., 30 s at 67° C., 13 min at 68° C.

The $2^{nd}$ round PCR was performed with Advantage 2 Polymerase Mix and primer pairs listed in table 3, the PCR cycle parameters were as follows: 35 s at 99° C. followed by 35 cycles of 35 s at 99° C., 30 s at 67° C., 10 min at 68° C. and a final 10 min at 68° C. The fragments were agarose gel purified (Wizard SV gel and PCR Clean-Up System) and directly sequenced in both directions.

The SA13/JFH1 RNA from supernatants of the $1^{st}$ passage B experiment day 7, $2^{nd}$ passage A and B experiment, day 7 and 8, respectively, were sequenced. The corresponding SA13/JFH1-GND supernatants were extracted and RT-PCR was performed in parallel as a negative control.

Clonal Analysis of a Long RT-PCR Amplicon Spanning the Positions with Evidence of Mutations in Cell Culture Derived SA13/JFH1 Viruses cDNA was generated from $2^{nd}$ passage A day 7 supernatant as described above. The PCR procedure was performed with Advantage 2 Polymerase Mix, following the standard protocol (see above) with primers—285S_HCV-MOD and 7234R_JFH1 (SEQ ID NO: 21 and 38) (Table 3). Cycling parameters were 35 s at 99° C. followed by 35 cycles of 35 s at 99° C., 30 s at 67° C., 9 min at 68° C. and a final 10 min at 68° C. The obtained fragment was cloned into pCR-XL-TOPO and 10 clones were sequenced.

$TCID_{50}$ Viral Titration Assay.

To determine the infectivity of the cell culture derived viruses given as 50% tissue culture infectious dose ($TCID_{50}$) serial dilutions of the supernatant were passed on to naïve cells. The virus titer capable of infecting 50% of the test units was calculated by using the cumulated values and by assuming that the proportion of infected cells is linear with $\log_{10}$ dilution (Reed and Muench, 1938). The day before infection, the cells were plated with $6 \times 10^3$ cells/200 μl per well, in a polylysine coated Nunc 96 Well Optical Bottom Plate (Nunc) and incubated overnight at 37° C., in 90% humidity and 5% $CO_2$. 24 hours later the cells were incubated, in replicates of 6 wells, with 10-fold dilutions ($10^{-1}$-$10^{-7}$) of cell culture supernatants and a negative control consisting of medium only.

48-72 hours later the cells were washed twice with PBS and fixed and permabilized with ice cold Methanol for 5 min. The plate was washed twice with PBS, once with PBS/0.1% Tween and unspecific binding was blocked with 1% BSA/0.2% skim milk in PBS for 20 min at room temperature. Endogenous peroxidase was blocked with 3% $H_2O_2$ for 5 min at room temperature. The plate was washed twice with PBS, once with PBS/0.1% Tween and incubated overnight at 4° C. with primary antibody against NS5A (anti-NS5A, 9E10, kindly provided by Charles Rice) in a 1:200 dilution in PBS/0.1% Tween. After overnight incubation the plate was washed twice with PBS, once with PBS/0.1% Tween, and secondary antibody HRP conjugated goat-anti-mouse (ECU™ Anti-mouse IgG, horseradish peroxidase linked whole antibody, Amersham Bioscience) in a 1:200 dilution in PBS/Tween was added and incubated for 30 min at room temperature. The plate was washed twice with PBS, once with PBS/0.1% Tween, and stained by adding a horseradish peroxidase substrate (DAB substrate kit, DAKO) for 30 min at room temperature. The plate was washed twice with PBS and Fluoromount-G (Southern Biotech) was added to each well. Each well was examined with light microscopy to identify cells positive for HCV NS5A protein and thereby scored positive. Wells were scored negative if no positive cells were identified. $TCID_{50}$ calculations were done as described by Reed and Muench.

Real-Time PCR (Taqman) Assay of HCV RNA.

Our laboratory has established a real-time PCR for HCV. Samples for the Real-time PCR assay for measuring HCV RNA titers were 200 μl cell culture supernatant and a quantitative standard panel covering concentrations of 0 to $5 \times 10^6$ IU/ml in one log steps (OptiQuant HCV Panel, AcroMetrix). RNA from heat inactivated cell cultures supernatant was extracted using Total Nucleic Acid Isolation Kit (Roche) in combination with the Total NA Variable Elution Volume protocol on a MagNA Pure LC Instrument (Roche) according to the manufacturers' instructions. An internal control, Phocine Distemper Virus (PDV) was included in the process by adding titrated concentrations to the lysis buffer, the value of the PDV reaction for each sample was compared to the expected value to confirm a successful purification and amplification. The Real-time PCR analyses of HCV and PDV were carried out in two separate reactions using the TaqMan EZ RT-PCR Kit (Applied Biosystems). The HCV RNA in the samples was amplified and detected using a 5' UTR based primer/probe mix, which included a forward primer, a reverse primer and FAM-labeled MGB-probe (Applied Biosystems). The primer/probe mix recognizes all six major HCV genotypes and has previously been shown to have equal sensitivity to these genotypes in different TaqMan assays. For the control virus PDV, a ready-to-use primer/probe mix was used (Erasmus Medical Centre, Rotterdam, The Netherlands). The PCR analysis was performed on a 7500 Real-Time PCR System (Applied Biosystems) and a standard curve of the HCV panel was created from the known concentrations and used to calculate the HCV concentration (IU/ml) of the remaining samples. The detection limit of the assay was 500 IU/ml.

Generation of Mutant pSA13/JFH1 C3405G (SEQ ID NO: 54).

To introduce the coding point mutation C to G at position 3405 in pSA13/JFH1, 2 overlapping fragments were generated by PCR with Pfu: the first product was amplified from pSA13/JFH1 (SEQ ID NO: 1) with primers SA13JFH1F1827 and SA13-R3430-3405G (SEQ ID NO: 12 and 53) (Table 5), and the second product was amplified with primers SA13-F3380-3405G and 4118R_JFH1 (SEQ ID NO: 52 and 30). The reagent protocol for the first fragment included 2 μl of dNTP (10 mM), 5 μl of SA13JFH1F1827 (10 mM), 5 μl of SA13-R3430-3405G (10 mM), 10 μl 10× Buffer, 20 Pfu (2.5 U/μl), 230 ng pSA13/JFH1 and H2O to a total volume of 100 μl. Cycling parameters were 45 s at 95° C. and 25 cycles of 45 s at 95° C., 45 s at 62° C., 3 min at 72° C., followed by 10 min at 72° C. The second fragment was amplified with the same cycle parameters except the elongation time being 4 min. The reagent protocol was as follows: 10 dNTP (10 mM), 20 of SA13-F3380-3405G (10 mM), 2 μl of 4118R_JFH1 (10 mM), 5 μl 10× Buffer, 0.5 μl Pfu (2.5 U/μl), 230 ng pSA13/JFH1 and H2O to a total volume of 50 μl.

The two fragments were purified and fused using primers SA13JFH1F1827 (10 mM) and 4118R_JFH1 (10 mM) (SEQ ID NO: 12 and 30) Pfu, and approximately 150 ng of each fragment. Cycling parameters were 45 s at 95° C. and 25 cycles of 45 s at 95° C., 45 s at 62° C., 5 min at 72° C., followed by 10 min at 72° C. The AflII/SpeI fragment of the fusion PCR product was introduced into pSA13/JFH1. The plasmid was transformed into TOP10 bacteria, and 3 clones were sequenced and a single clone was identified with the correct sequence. The other 2 mutants were generated in analogy using fusion PCR, with primer pairs: SA13JFH1 F 1827 and SA13mutaA3696G R (SEQ ID NO: 12 and 60) for fusion with fragment made with 4118R_JFH1 and SA13muta A3696G F(SEQ ID NO: 61 and 30), for the A3696G mutation (SEQ ID NO: 58) in pSA13/JFH1-C3405G (SEQ ID NO: 57). For pSA13/JFH1-G2611T-A2728G-C3405G-A3696G (SEQ ID NO: 59) a 4 piece fusion were made with primer pairs; SA13JFH1 F 1827 and SA13muta G2611T R, SA13muta G2611TF and SA13muta A2728G R, SA13muta A2728G F and SA13muta 3696G R, 4118R_JFH1 and SA13muta A3696G F (SEQ ID NO: 12, 62, 63, 64, 65, 60, 30 and 61) (Table 5).

Analysis of SA13/JFH1 entry by CD81 and SR-BI blocking and by incubation with 5a patient sera or purified IgG.

6×10³ Huh7.5 cells/well were plated on poly-D-lysine coated 96 well plates (Nunc) ~24 hours before the assays. For CD81 blocking, cells were incubated with anti-CD81 (JS-81, BD Biosciences, Pharmingen) or isotype matched control antibody (anti-human immunodeficiency virus, p24, clone Kal-1; DAKO) and for SR-BI blocking, cells were incubated with rabbit polyclonal anti-SR-BI (GeneTex) or rabbit polyclonal control antibody (anti human Retinoblastoma (Rb) Ab-6, Thermo Scientific), for 1 hour before adding ~150 focus forming units (FFUs) of SA13/JFH1 C3405G-A3696G or J6/JFH and incubating for 3 hours before washing once with PBS. Experiments were performed in triplicates unless stated otherwise. Cells were incubated for 2 days in complete medium and stained to determine the number of FFUs. Percent inhibition by anti-CD81 and anti-SR-BI was calculated by comparison to the FFU mean of 3 replicate wells incubated with virus only.

For neutralization assays, heat inactivated (56° C. for 30 min) sera were pre-incubated with ~50, 100, 200, 400 or 800 TCID50 of SA13/JFH1C3405G-A3696G virus or ~100-200 TCID50 of JFH1-based recombinant viruses of genotypes 1a, 2a, 3a, 4a, and 6a (Gottwein, unpublished) for 1 hour at 37° C., preceding 3 hours incubation on Huh7.5 cells plated on 96 well plates.

Polyclonal IgG was purified from 200 µl serum from selected samples; IgG purification was performed with Protein G HP SpinTrap (GE Healthcare) and Ab Buffer Kit (GE Healthcare) as described by the manufacturer and quantified by standard methods (Department of Clinical Biochemistry, Copenhagen University Hospital, Hvidovre). For neutralization with IgG, 100 FFUs SA13/JFH1 C3405G-A3696G were pre-incubated with 40, 20, 10, 5, 2.5, 1.25, 0.625 µg of the respective IgG for 1 hour at 37° C. before incubating 3 hours on Huh7.5 cells plated on 96 well plates. Neutralization experiments with Patient sera and IgG were performed in triplicates and after 3 hours incubation, cells were washed with PBS and incubated with complete medium for 2 days and stained to determine the number of FFU. Percent inhibition by patient sera was calculated by comparison to the serum control. The inventors of the present invention have found that incubation of each of the genotype viruses with this serum control at 1:50 or 1:100 dilutions resulted in similar counts of FFU as the corresponding virus only control (data not shown). Percent inhibition by purified IgG was calculated by comparison to 6 replicates of virus only. Genotype 5a positive sera (SA1, SA3 and SA13) used for neutralization were from South African hepatocellular carcinoma patients. Treatment of HCV Infected Cells with Neutralizing Antibodies.

A 1:50 or 1:200 dilution of heat inactivated patient serum (SA3) or serum control were pre-incubated with ~50 or ~100 TCID50 of SA13/JFH1 virus, respectively, for 1 hour at 37° C. and added to 1×10⁵ or 1.5×10⁵ Huh7.5 cells/well, respectively, of a 24 well plate (Nunc) for 24 hours. Cells were washed with PBS, and fresh medium supplemented with the SA3 serum or serum control at a 1:50 or 1:200 dilution, respectively, was added every 24 hours. The envelope sequences of recovered viruses were determined from amplicons obtained from supernatant in a JFH1 specific RT-PCR with RT primer 4118R_JFH1 (see above) and PCR primers—285S_HCV-MOD and JFH1R4141 (SEQ ID NO: 30, 21 and 49). Amplicons for direct sequencing of both treatment experiments were generated with primer mix 1-4 (see above). For clonal analysis of the amplicons from the low dose (1:200) experiment, the PCR product (nts 86-4140) was cloned into pCR-XL-TOPO (Invitrogen) and sequenced, to further analyze a position with evidence of change in direct sequencing.

Example 1

Cloning and Determination of the Consensus Sequence of the SA13 Genome

The consensus sequence of SA13 (nts.1-9523; numbers of nucleotide positions refer to full-length SA13), containing the ORF and all but the first 34 nucleotides of the 5' UTR and the last 81 nucleotides of the 3' UTR was determined.

Figure 1:
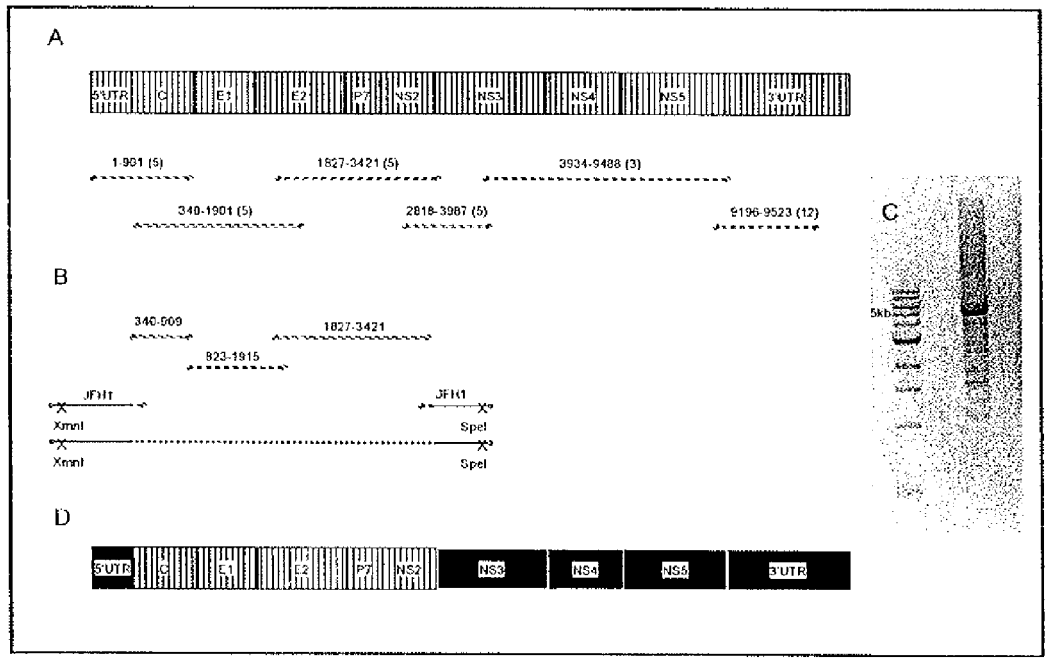
FIG. 1. Determination of SA13 consensus sequence and generation of SA13/JFH1 chimera (SEQ ID NO: 1) from subcloned amplicons. SA13 sequence is shown in striped/dashed, and JFH1 sequence is shown in black. A: Schematic representation of the HCV genome and the PCR fragments amplified from plasma of a genotype 5a infected chimpanzee. The nucleotide positions correspond to the full-length SA13 genome sequence, the number of clones sequenced is shown in brackets. B: The SA13 and JFH1 fragments were amplified from plasmids and fused in a 5-piece fusion PCR (Agarose gel electrophoresis of the 5-piece fusion PCR product of approximately 5 kb is shown to the right). The restriction sites used to introduce the SA13 sequence into the JFH1 backbone are indicated on the two JFH1 fragments and on the final fusion product. C: Agarose gel electrophoresis of the 5 piece fusion PCR product at approximately 5 kb. D: The intergenotypic SA13/JFH1 genome (SEQ ID NO: 1) with the structural genes and p7, NS2 of SA13 and the 5'UTR, 3'UTR and NS3 through NS5B of JFH1.

HCV specific RT-PCR on RNA extracted from the chimpanzee genotype 5a plasma pool was used to amplify the near complete genome in 6 overlapping fragments (FIG. 1).

All 6 fragments were subcloned and 3 to 12 clones were sequenced and analyzed to determine the consensus sequence, which represents the most common nucleotide at each position among the clones analyzed. Heterogeneity was observed at 271 nucleotide positions (3%) in the ORF and at 86 amino acid positions (2.9%) of the polyprotein. These differences could be the result of errors introduced during PCR amplification although a polymerase with proofreading function was used or they could represent the quasispecies nature of HCV. The consensus sequences deduced from the clonal analysis of amplicons were aligned to the previously determined consensus SA13 sequence obtained from direct sequencing of amplicons (GenBank accession number AF064490). In the 5'UTR no differences was observed. In the ORF, 54 nucleotide differences was observed, which resulted in amino acid changes at 8 positions. At 19 of the 54 nucleotide positions with differences, the sequence previously reported was observed among at least one of the clones analyzed in the present study. Within the 3'UTR, there were no specific nucleotide differences in the 3' variable region, the poly-pyrimidine tract and the portion of the conserved X region analyzed. However, there was some variation in the length of the 3'UTR in the 12 clones sequenced, entirely due to differences in the length of the polypyrimidine tract. That region varied from 48 to 67 nucleotides in length among the 12 clones analyzed in the present study and from 44-127 nucleotides among clones analyzed in the original study of the SA13 strain (Bukh et al., 1998). The differences observed in the SA13 sequence published previously and the one which was amplified from the same chimpanzee plasma pool probably reflects the quasispecies nature of HCV, as also evidenced by the fact that clonal heterogeneity at many of the positions with difference between the consensus sequence in this study and the one determined previously (see above) was observed. In HCV infected humans a pool of closely related viruses exists, developing in part as a result of immune evasion (Hoofnagle, 2002), and probably being the major reason for the heterogeneity detected. In addition in the previous and the actual study different methods for determination of the consensus sequence were used (Bukh et al., 1998). While the published SA13 sequence has primarily been determined by direct sequencing of PCR products the consensus sequence in this study is deduced from clonal analysis, which should provide a more detailed analysis of the actual combination of nucleotides in each fragment.

Example 2

Generation of Full-Length SA13/JFH1 Consensus Clone

Until recently there was no reproducible cell culture system to grow HCV. Full-length genomes found to be infectious in chimpanzees did not show clear evidence of replication in cell culture (Bukh and Purcell, 2006). However, in 2005, it was reported that full-length RNA transcripts of a genotype 2a strain (strain JFH1) could replicate in Huh7 cells and produce infectious particles (Zhong et al., 2005; Wakita et al., 2005) and that a genotype 2a/2a recombinant constructed on the backbone of JFH1 but with the structural genes (Core, E1, E2), p7 and NS2 from another 2a strain (strain HC-J6) could generate higher titers in Huh7.5 cells (Lindenbach et al., 2005). Thus a viable intergenotypic 5a/2a recombinant was generated.

The pSA13/JFH1 plasmid (SEQ ID NO: 1) was constructed by inserting the structural genes (Core, E1, E2), p7 and NS2 of genotype 5a strain SA13 into pFL-J6/JFH. As a result, only the nonstructural genes NS3, NS4A, NS4B, NS5A and NS5B and the 5'- and 3'-UTR originates from strain JFH1, but these are the regions important for RNA replication. Therefore in the intergenotypic recombinants of the present invention the unique replication characteristics of JFH1 are utilized.

To generate pSA13/JFH1, five overlapping PCR fragments of SA13 and JFH1 were amplified and fused together by a 5-piece fusion PCR to obtain a chimeric PCR fragment (FIGS. 1B, C). The SA13 fragments from Core to NS2 were amplified from clones generated in the present study to obtain the amplicons with the sequence from nucleotides 341 to 901 and nucleotides 1827-3421 of SA13; the clones used represented clones that had been corrected to have the consensus sequence, as described in the "materials and methods" part. The fragment from nucleotide 823-1915 was amplified from pCMV-SA13, which were previously constructed to generate retroviral pseudo-particles of strain SA13 (Meunier et al., 2005). This sequence was used due to an excessive number of mutations at different positions in all 5 clones of our PCR fragment, making it difficult to make a consensus clone. The JFH1 PCR fragments were amplified from pFL-J6/JFH, and besides an overhang into the SA13 sequence each fragment had a unique restriction site as showed in FIG. 1B. Finally, the 5-piece fusion product was generated from purified amplicons with a high fidelity enzyme and the extreme 5' forward and 3' reverse primers, TOPO cloned and sequenced. The fusion product was introduced into the pFL-J6/JFH by restriction digest with XmnI/SpeI (see FIG. 1 and as described in the "material and methods" part)

The final SA13 sequence in the SA13/JFH1 genome had 2 nucleotide (0.06%) differences from the consensus sequence determined for SA13 in the present study; one of these difference resulted in an amino acid change (N384S in HVR1 of E2; number of amino acid positions refer to SA13/JFH1 polyprotein).

Example 3

Generation of Replication Defective Control Plasmid PSA13/JFH1-GND

HCV can be rendered infection and replication deficient by introduction of a point mutation in the NS5B RNA polymerase active site, which results in the amino acid change GDD to GND (Lindenbach et al., 2005). The replication deficient pFL-J6/JFH-GND and the cloned and sequenced 5-piece fusion products (see above) were digested with XmnI and SpeI, and the J6 part of the plasmid was exchanged with the SA13 Core through NS2. RNA transcripts of pSA13/JFH1-GND were shown not to replicate in Huh7.5 cells.

Example 4

Cell Culture of Recombinant JFH1 Based Viruses of HCV

Figure 2:
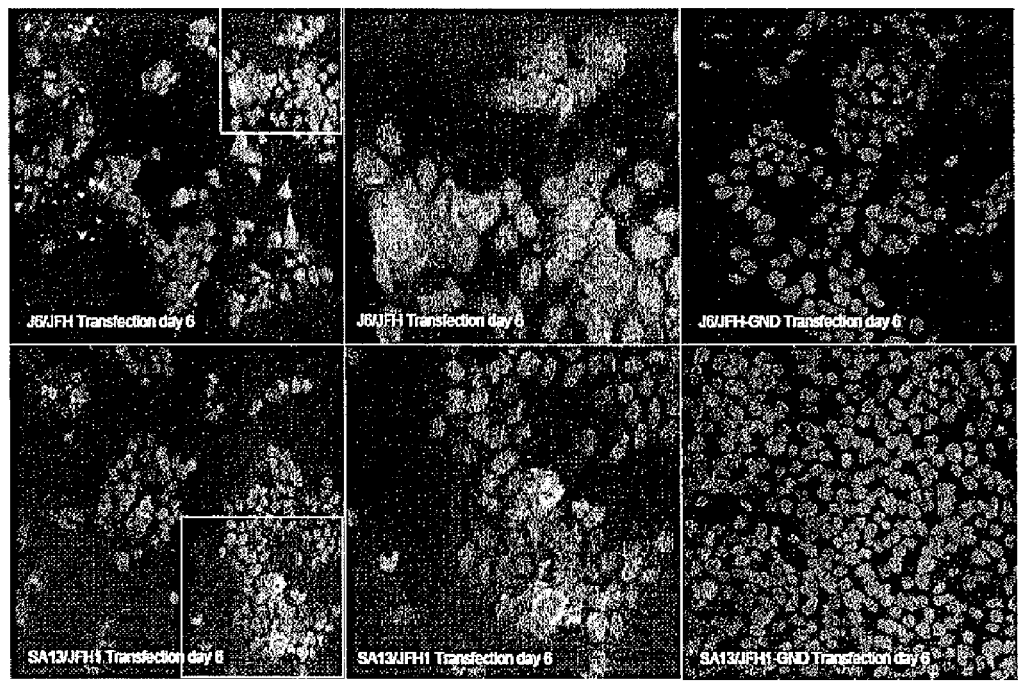
FIG. 2. Immunofluorescence staining of transfected Huh7.5 cells for HCV Core antigen. The figure shows cell slides of the transfection at day 6 for SA13/JFH1 (SEQ ID NO: 1), J6/JFH and the replication deficient SA13/JFH1-GND and J6/JFH-GND. The white boxes in the 1st column show the enlarged detail shown in the 2nd column. Huh7.5 cells were plated in 6-well plates with $4 \times 10^5$ cells/well 24 hrs before cells were transfected. Each well was transfected with 2.5 µg RNA transcripts of SA13/JFH1 (SEQ ID NO: 1), J6/JFH and the replication deficient GND genomes with Lipofectamine 2000. The cells were split every 2-3 days and the percentage of infected cells was evaluated by staining for HCV Core protein. 24 hrs before the staining, the cells were trypsinized and plated in 8 chamber slides with $0.5 \times 10^5$ cells/300 µl or 4 chamber slides with $1.5 \times 10^5$ cells/600 µl and incubated overnight at standard conditions as described in Materials and Methods. After the cells were fixed, intracellular staining was performed with primary antibody (Murine Anti-Human HCV Core Protein Clone B2 (MAB, Anogen)) in PBS/5% BSA. The slides were washed with PBS and PBS/0.1% Tween, and incubated with secondary antibody, Alexa Fluor 594-conjugated goat-anti mouse IgG in PBS/0.1% Tween. Cell nuclei were stained with Hoechst dye. The slides were washed and mounted with Fluoromount-G and cover glass. Slides were evaluated for percentage of infected cells by examination with a Leica confocal fluorescence microscope.

Transfection of Huh7.5 cells with SA13/JFH1 (SEQ ID NO: 1) and J6/JFH genomes Since it has been documented that J6/JFH (intragenotypic 2a/2a genome) can replicate and produce infectious particles in Huh7.5 cells, said genome was used as a positive control for the study of the viability of the intergenotypic 5a/2a genome. RNA transcripts of J6/JFH, SA13/JFH1 (SEQ ID NO: 1), J6/JFH-GND and SA13/JFH-GND were transfected into naïve Huh7.5 cells with Lipofectamine 2000. To verify SA13/JFH1 replication, immunostaining of the HCV Core protein was performed when the cells were split, and the percentage of infected cells was determined by microscopy as shown in FIG. 2.

The J6/JFH and SA13/JFH1 (SEQ ID NO: 1) genomes were successfully transfected into Huh7.5 cells, since intracellular cytoplasmic cellular Core antigen staining in cells collected on day 1 post-transfection in both cultures could detect the. It was found that the J6/JFH replicated and infected Huh7.5 cells, showing that it was possible to reproduce the experiments that were the foundation of the HCV cell culture system, and thereby validating the virus cell culture assay. On day 3, J6/JFH had infected 25% of the cells and reached peak infection levels on days 6 and 9 post-transfection (FIG. 3).

During the next two weeks, following massive cell death in the culture, the percentage of infected cells slowly declined to 20%.

In the SA13/JFH1 culture, less than 5% of the Huh7.5 cells were Core-antigen positive on days 1, 3 and 6 (FIG. 3). However, at day 8 post-transfection, SA13/JFH1 viruses had spread in the cell culture infecting 30% of the cells and within the next 4 days the infection reached its peak at 80% infected cells, as high a percentage as seen in the J6/JFH culture. Furthermore, at peak infection a observed massive cell death was observed and thereafter, as observed for J6/JFH, the percentage of infected cells decreased as the cells recovered, with 20% infected cells at three weeks post-transfection. The decrease in the percentage of infected cells after peak infection occurred in all cell culture experiments conducted in this report and is preceded by a phase of massive cell death. This may be due to natural selection of cells, which are less susceptible to virus infection. This has been observed also in other studies of the JFH1 virus in Huh7 cells (Zhong et al., 2006).

The replication deficient SA13/JFH1-GND and J6/JFH-GND served as negative controls and were both negative throughout the experiment (J6/JFH-GND; data not shown for simplicity of the graphs). The supernatants collected at the peak of infection had infectivity titers of $10^{3.7}$ TCID$_{50}$/ml for day 10 of the J6/JFH culture and $10^{3.6}$ TCID$_{50}$/ml for day 13 of the SA13/JFH1 culture (FIG. 3 and Table 6) demonstrating that the SA13/JFH1 (SEQ ID NO: 1) intergenotypic recombinant can reach as high titers as seen in the established J6/JFH1 culture. In comparison to J6/JFH viruses slow spread of SA13/JFH1 viruses, was reflected in the TCID$_{50}$ values determined at days 3 and 10 post-transfection, with titers of less than $10^{1.3}$ TCID$_{50}$/ml and $10^{2.3}$ TCID$_{50}$/ml, respectively, for the SA13/JFH1 culture compared to titers of $10^{3.1}$ and $10^{3.7}$ TCID$_{50}$/ml for the J6/JFH culture (FIG. 3).

The different cell cultures were all transfected with 2.5 µg of RNA transcripts, so the input RNA should be the same for both recombinants, as well as the replication deficient controls. Thus, the delayed course of infection and lower infectivity titers showed that the original SA13/JFH1 viruses (SEQ ID NO: 1) were less virulent or fit than J6/JFH1 viruses, but at peak infection SA13/JFH1 viruses (SEQ ID NO: 1) had as high infectivity titers as J6/JFH. This could show that the growth capacity of the 5a/2a recombinant increased during the transfection experiment, presumably because of the acquisition of adaptive mutations. However, due to the input DNA/RNA from the transfection it was not possible to directly analyze the genome sequence of viruses obtained in the transfection experiment. Two passages of SA13/JFH1 viruses (SEQ ID NO: 1) from the transfection experiment were performed with supernatant collected at days 13 and 15 post-transfection, respectively (FIG. 3, Table 7). Subsequently, viruses from each of these $1^{st}$ passage experiments were passed in a $2^{nd}$ passage experiments. The inoculums used in these experiments are showed in Table 7.

To further illustrate the delay of spread in SA13/JFH1 (SEQ ID NO: 1) cultures compared to J6/JFH, the three independent transfections of Huh7.5 cells with RNA transcripts are shown only with infectivity titers, TCID$_{50}$ (FIGS. 9A, B and C). SA13/JFH1 (SEQ ID NO: 1) was shown to yield supernatant infectivity titers of less than $10^{1.5}$ TCID$_{50}$/mL for the first 6 days after transfection (FIGS. 9A and B). However, the J6/JFH positive control culture, showing infectivity titers below $10^1$ TCID$_{50}$/mL on day 1 (FIG. 9B), yielded titers of $10^4$-$10^{4.5}$ TCID$_{50}$/mL on day 6 (FIGS. 9A and B), when HCV Core was expressed in most cells of the culture. For SA13/JFH1 (SEQ ID NO: 1), similar infectivity titers and a high percentage of infected cells were not observed until day 13, 10 and 9, respectively (FIGS. 9A,B and C).

$1^{st}$ Passages of SA13/JFH1 and J6/JFH Viruses

To further characterize the SA13/JFH1 virus (SEQ ID NO: 1) produced in the transfection experiment and to adapt it to better growth in culture, naïve Huh7.5 cells were inoculated with sterile filtered supernatants from the transfection cell culture, thereby only transmitting free virus particles. In the $1^{st}$ passage A, supernatants from around peak infection (day 15 post-transfection for SA13/JFH1, day 8 post-transfection for positive control J6/JFH and the negative control SA13/JFH1-GND), were passed on to the naïve Huh7.5 cells. The infectivity dose of the inoculum was approximately $10^{3.3}$ TCID$_{50}$ for SA13/JFH1 and $10^{3.1}$ TCID$_{50}$ for J6/JFH (Table 7). The cells were kept for only 8 days since massive cells death occurred at this time, and the experiment was closed. However, the immunostaining for Core protein in the cells showed a high percentage of infected cells for both SA13/JFH1 and J6/JFH on days 3 and 5 post-infection (FIG. 4A). It was difficult to make conclusions on the kinetics of the viruses based on only two data points, but the experiment showed that SA13/JFH1 and J6/JFH1 infected an equal percentage of cells in the same amount of time, with SA13/JFH1 spreading faster than observed in the transfection experiment. The HCV RNA titers were measured for both recombinant viruses at days 3 and 5 and were found to be similar at ~$10^6$ IU/ml (FIG. 4A), and the infectivity titers were $10^{3.3}$ TCID$_{50}$/ml in both the SA13/JFH1 and the J6/JFH1 culture at day 3 post-infection (Table 6). The specific infectivity (genomes in IU per infectious dose) for SA13/JFH1 and J6/JFH on day 3 was 1:1000 and 1:501, respectively.

A subsequent $1^{st}$ passage (FIG. 4B) was performed using SA13/JFH1 supernatant from an earlier time point of the transfection (day 13 post-transfection). The virus dose of the inoculum was $10^{3.6}$ TCID$_{50}$ for SA13/JFH1 and $10^{3.1}$ TCID$_{50}$ for J6/JFH (Table 7). The cell culture was followed for 17 days and the first passage viruses showed similar percentage of infected cells at each time point analyzed for J6/JFH and SA13/JFH1. Both viruses had spread to most cells at day 3 post-infection and reached the peak of infection at day 7 (FIGS. 4B and 5). The SA13/JFH1-GND showed no staining at any time point.

The experiments showed an accelerated kinetics of the SA13/JFH1 virus recovered late during the transfection compared with the original genome. In order to evaluate the infectivity titers of $1^{st}$ passage B SA13/JFH1 viruses, infectious titers were measured for supernatant from the day of the peak percentage infected cells, day 7 for both SA13/JFH1 and J6/JFH. The infectivity titers at the peak of infection (day 7) were $10^{4.2}$ TCID$_{50}$/ml for SA13/JFH1 and $10^{4.3}$ TCID$_{50}$ for J6/JFH, respectively (Table 6). It is noticeable that these infectivity titers are about 1 log higher than those determined at the peak of infection in the transfection experiment (Table 6). The SA13/JFH1 RNA titers of this $1^{st}$ passage could not be compared with the titers from the transfection, because it is not possible to get those since there is too much input DNA/RNA to get reliable results in the TaqMan procedure. However with values of ~10' (between days 3-10) for SA13 they were comparable to those of J6/JFH. At last also the specific infectivities for SA13/JFH1 and J6/JFH viruses were similar with 1:501 and 1:398, respectively, at the peak of infection (day 7) (Table 6).

This $1^{st}$ passage experiment shows that the SA13/JFH1 viruses that evolved in the transfection experiment are, in contrast to the original SA13/JFH1 viruses, as infectious and spread as fast as J6/JFH viruses in cell culture.

Comparison of growth kinetics of serially passed SA13/JFH1 and J6/JFH viruses. To systematically compare the growth kinetics of the intergenotypic SA13/JFH1 viruses obtained in the $1^{st}$ passages A and B with those of J6/JFH viruses, two independent $2^{nd}$ passages experiments were conducted (A and B, FIG. 6 and Table 7) by inoculation of naïve Huh7.5 cells with the same infectious dose of SA13/JFH1 and J6/JFH $1^{st}$ passage viruses.

For inoculation of the $2^{nd}$ passage A supernatants of SA13/JFH1 and J6/JFH were derived at day 3 of the $1^{st}$ passage A (FIG. 4A), showing an infectivity titer of $10^{3.3}$ TCID$_{50}$ for both viruses and an HCV RNA titer of $10^{6.3}$ IU and $10^{6.0}$ IU for SA13/JFH1 and J6/JFH, respectively (Table 6). SA13/JFH1-GND negative control supernatants were derived at the same day. After infection the present inventors observed a very similar kinetic for SA13/JFH1 and J6/JFH. More than 50% of the cells were infected at day 3 and most cells were infected on days 5 and 7, with SA13/JFH1 reaching the peak of infection before J6/JFH. The negative control SA13/JFH1-GND culture showed no staining at any time point. When comparing the infectivity titers of the two viruses at days 1, 3, 5 and 7 they followed each other closely with less than 0.3 $\log_{10}$ differences in $TCID_{50}$ (FIG. 6). The HCV RNA titers were also very similar for SA13/JFH1 and J6/JFH throughout the experiment with peak titers at days 5 and 7 (FIG. 6). The highest specific infectivity for SA13/JFH1 was measured on day 1 (1:158) and for J6/JFH on day 1 and 3 (1:126). Thus the specific infectivity had increased from the $1^{st}$ to the $2^{nd}$ passage of this experimental line.

For inoculation of the $2^{nd}$ passage B the supernatants of SA13/JFH1 and J6/JFH from $1^{st}$ passage B, day 7 (FIG. 4B) were used showing infectivity titers of $10^{4.2}$ $TCID_{50}$ and $10^{4.3}$ $TCID_{50}$, respectively (Table 7), which is about 1 $\log_{10}$ higher than the dose used for the other kinetic experiment (Experiment A). SA13/JFH1-GND supernatants were from the same day as SA13/JFH1.

The percentage of infected cells in the SA13/JFH1 and J6/JFH cultures both peaked at around days 6 and 8 post-infection, as seen in the other $2^{nd}$ passage experiment (FIG. 6B). The negative control showed no replication at any time point. The RNA titers for SA13/JFH1 and J6/JFH1 in this kinetic experiment were higher on day 1 compared to the first kinetic experiment in accordance with the higher dose of the inocula, but this initial increase was not seen at day 3 and onwards, and the titers in general were not as high as in the first kinetic experiment (Table 6). The infectivity titers for this kinetic experiment were a bit lower than the ones measured for SA13/JFH1 at peak percent infection in the first kinetic experiment with $10^{4.3}$ and $10^{4.7}$ for day 6 and 8 respectively, but still showed an increase compared to the $1^{st}$ passage. Infectivity titers for J6/JFH were not measured, so specific infectivity could only be determined for SA13/JFH1, which was 1:398 and 1:200 at day 6 and 8, respectively. These specific infectivities were much higher than for the $1^{st}$ passage of this virus. Thus the increased input of virus did not change the course of infection significantly, perhaps due to the faster selection of resistant cells as the massive cell death occurred at an earlier time point in $2^{nd}$ passage B compared to $2^{nd}$ passage A experiment.

The J6/JFH chimera showed the same kinetic through all the passages, peaking at approximately the same time points in the transfection, $1^{st}$ and $2^{nd}$ passages. This might be due to the fact, that this 2a/2a recombinant does not require further adaptation for efficient growth in cell culture. Evidence for a genetically stable J6/JFH in the present cell culture system has been provided from sequence analysis of serially passed virus in our laboratory (J. Gottwein and T. Scheel, personal communication). SA13/JFH1 on the other hand shows a significant change in kinetics from the transfection to $1^{st}$ and $2^{nd}$ passages. This intergenotypic 5a/2a recombinant reached peak titer about one week later than the control virus J6/JFH in the transfection experiment During the $1^{st}$ passage however the virus spread was similar for SA13/JFH1 and J6/JFH1. There was no further increase in the rate at which infection spread from the $1^{st}$ to $2^{nd}$ passage for SA13/JFH1. However, infectivity titers, RNA titers and specific infectivities, increased in both experiments from the $1^{st}$ passage to the $2^{nd}$ passage (Table 6). These findings show that the SA13/JFH1 viruses were adapting and that the virions were more infectious in the serially passed virus.

Example 5

Putative Adaptive Mutations in Serially Passed SA13/JFH1 Viruses

The results from the cell culture studies support that J6/JFH was fully viable in Huh7.5 cells. In contrast the growth potential of SA13/JFH1 (SEQ ID NO: 1) appeared to improve from the transfection experiment to the $1^{st}$ passages. One possibility is that the SA13/JFH1 genome (SEQ ID NO: 1) acquired adaptive mutations, since adaptations of the cells would not be important here, as naïve cells were used for each passage of the virus. To investigate reasons for the increased growth/infectivity potential of the intergenotypic 5a/2a virus, sequencing of the viruses rescued from the $1^{st}$ and $2^{nd}$ passages of SA13/JFH1 was performed.

Direct Sequencing of $1^{st}$ and $2^{nd}$ Passage SA13/JFH1 Viruses

Direct sequence analysis was performed on SA13/JFH1 genomes recovered from day 7 supernatant of the $2^{nd}$ passage A (FIG. 6A) and from day 8 supernatant of the $2^{nd}$ passage B (FIG. 6B). Direct sequencing was performed on 12 overlapping PCR fragments that comprised nucleotides 257-9469, including the entire ORF. The mutation analyses were performed by comparing the sequence of the rescued viral genomes with the sequence of the pSA13/JFH1 plasmid used in the transfection experiment. As seen in Table 8, at several nucleotide positions the mutated sequence is present together with the original nucleotide sequence, indicating the presence of a quasispecies population in the passed SA13/JFH1 virus pools. The mutations found in the $2^{nd}$ passage viruses were located at nucleotides 2611 and 2728 in the p7 gene, at nucleotide 3405 in NS2, at nucleotide 3696 in NS3 and at nucleotide 6839 and in NS5A (nucleotide position numbers refer to pSA13/JFH1 (SEQ ID NO: 1)). All the mutations showed a 50:50 distribution in the $2^{nd}$ passage virus pool, except the one at position 6839, where the mutation represented the minor quasispecies. The nucleotide mutations in NS2, NS3 and NS5A result in changes in the deduced amino acid sequence, whereas the mutations in p7 are silent (Table 8A+B).

To determine at which time point these mutations arose, direct sequencing was also performed on $1^{st}$ passage B viruses recovered from day 7 supernatant (FIG. 4B). Evidence was found of the described mutations already during this $1^{st}$ passage, but the mutations in p7, NS3 and NS5A were all clearly minor sequences while the coding mutation at position 3405 showed a 50:50 distribution already in the first passage (see FIG. 7). This shows that the 3405 mutation might be particularly important for adaptation to cell culture. In summary, during serial passage of SA13/JFH1 viruses, apparently several putative adaptive mutations evolved, which are likely to be responsible for the improved growth characteristics of the late passages.

Sequencing of clones derived from second passage SA13/JFH1 viruses. To determine, how the putative adaptive mutations detected with direct sequencing were combined on individual SA13/JFH1 genomes, a long PCR fragment (including nucleotides 56-7371) of the $2^{nd}$ passage A day 7 virus was amplified, which thus contained all positions with evidence of mutations. The fragments were subcloned and 10 clones were sequenced.

It was found that 4 out of 10 clones had the original sequence at the 5 positions with evidence of mutations in p7, NS2, NS3 and NS5A by direct sequencing, which could show that the original viruses were viable. In 5 out of 10 clones a combination of G2611T and A2728G in p7, C3405G in NS2 and A3696G in NS3 was seen. In one of 10 clones only a single mutation was seen; G2611T located in p7. The mutation in NS5A, C6839T, was not detected in any of the 10 clones, but in the direct sequencing this position never showed a 50/50 distribution, indicating a very low prevalence in the virus population. Besides the expected mutations, a number of additional mutations was detected in each of the 10 clones analyzed; the majority of these mutations being represented only in a single clone. Thus the 10 clones are in fact different and do not in any case represent contamination with the original SA13/JFH1 genome. Clearly these additional mutations could represent adaptive mutations, also in the genomes with the original sequence at the positions with evidence of mutations in the direct sequencing. On the other hand, several of these mutations might represent PCR mistakes. It will require reverse genetics analysis of recombinant SA13/JFH1 genomes (SEQ ID NO: 1) with putative adaptive mutations to determine which mutations might be important for more efficient growth of SA13/JFH1.

Example 6

Transfection of 3 Recombinant SA13/JFH1 Genomes with Adaptive Mutations

Three recombinant SA13/JFH1 genomes with mutations at nucleotide positions G2611T (p7), A2728G (p7), C3405G (NS2) and A3696G (NS3) were tested in Huh7.5 cells (FIG. 8) and compared to the original SA13/JFH1 genome and J6/JFH. Mutation C3405G was tested alone and in combination with A3696G or all 3 mutations found in passed SA13/JFH1 viruses. The first mutation that became dominant in the $1^{st}$ passages of SA13/JFH1 was C3405G, and this is the reason the present inventors choose to test this mutation alone and in combination with other mutations. Only C3405G and A3696G caused amino acid changes (A1022G and K1119R respectively) and therefore they might have a more significant effect on adaptation, but in a clonal analysis of SA13/JFH1 virus from a $2^{nd}$ passage 5 out of 10 clones had all 4 mutations in combination. Huh7.5 cells were transfected with 2.5 μg of RNA transcripts of pSA13/JFH1 (SEQ ID NO: 1), C3405G-SA13/JFH1 (SEQ ID NO: 54), C3405G-A3696G-SA13/JFH1 (SEQ ID NO: 55), G2611T-A2728G-C3405G-A3696G-SA13/JFH1 (SEQ ID NO: 56), pFL-J6/JFH and pSA13/JFH1-GND.

As seen in the first transfection experiment with SA13/JFH1 (FIG. 3), there is a delay in the virus spread of SA13/JFH1 compared to the positive control J6/JFH1. However, the putative adaptive mutations introduced into the SA13/JFH1 construct in p7, NS2 and NS3 have a significant effect on rate of infection of SA13/JFH1 in the cell culture (FIG. 8).

As seen on the graph, SA13/JFH1 with the single mutation C3405G or in combination with other putative adaptive mutations spread as efficiently as the J6/JFH virus in Huh7.5 cells (FIG. 8).

Infectivity titers (TCID$_{50}$) were determined for SA13/JFH1 (SEQ ID NO: 1), C3405G-SA13/JFH1 (SEQ ID NO: 54), C3405G-A3696G-SA13/JFH1 (SEQ ID NO: 55), G2611T-A2728G-C3405G-A3696G-SA13/JFH1 (SEQ ID NO: 56) and FL-J6/JFH cultures on day 3 and were $10^{2.2}$ TCID$_{50}$/ml, $10^{3.9}$ TCID$_{50}$/ml, $10^{4.1}$ TCID$_{50}$/ml, $10^{4.3}$ TCID$_{50}$/ml, $10^{4.1}$ TCID$_{50}$/ml. When looking at infectivity titers, during transfection SA13/JFH1 (SEQ ID NO: 1) required an adaptation phase of at least 13 days before achieving titers of ~$10^5$ TCID50/mL (FIG. 9C, data not shown) and acquired an NS3 mutation in $1^{st}$ passage viruses (Table 8). In contrast, all three mutated recombinants showed growth characteristics comparable to J6/JFH with peak infectivity titers of ~$10^5$ TCID$_{50}$/mL in transfection and $1^{st}$ passage experiments (FIGS. 9C and 10) and peak HCV RNA titers of ~$10^{7.5}$ IU/mL in $1^{st}$ passage (FIG. 10); SA13/JFH1$_{C3405G}$ and SA13/JFH1$_{C3405G-A3696G}$ were genetically stable (SEQ ID NO: 54 and 55), whereas SA13/JFH1$_{G2611T-A2728G-C3405G-A3696G}$ (SEQ ID NO: 56) acquired a synonymous mutation in NS5A (Table 8B). It seems the mutations identified in direct sequencing and clonal analysis of the $2^{nd}$ passage SA13/JFH1 are adaptive mutation increasing infectivity titers of the recombinant genomes compared to the original SA13/JFH1 (SEQ ID NO: 1) and J6/JFH, and it seems the one mutation in NS2, C3405G is sufficient for the virus to be comparable to J6/JFH.

Example 7

Blocking of CD81 and SR-BI Inhibits Entry of Genotype 5a Viruses

In vitro infection of Huh7 derived cells with HCV genotypes 1 to 4 has been shown to depend on the cell surface receptor CD81 and genotypes 1 and 2 entry was shown to depend on SR-BI.

The present inventors demonstrated that genotype 5a entry also depended on CD81, since pre-incubation of Huh7.5 cells with anti-CD81 antibodies inhibited infection with SA13/JFH1$_{C3405G-A3696G}$ (SEQ ID NO: 55) virus in a dose dependent manner, achieving above 90% inhibition at 2.5 μg/mL (FIG. 11A). A dose dependent inhibition of entry was also seen when pre-incubating Huh7.5 cells with anti-SR-BI antibodies, yielding a 97% inhibition at a 1:10 dilution (FIG. 11B). For both receptor-blocking experiments, we tested inhibition of entry of J6/JFH1 in parallel and found comparable dose dependent results (FIGS. 11A and 3B).

Example 8

Efficient Neutralization of Genotype 5a Viruses by Chronic-Phase Sera and Purified IgG from Genotype 5a Infected Patients It was investigated whether sera of genotype 5a infected patients could neutralize ~100 TCID$_{50}$ of the homologous SA13/JFH1 virus (SEQ ID NO: 1) (FIG. 12A and Table 10). Autologous SA13 patient serum, the source of the SA13 strain, exhibited >50% neutralization at a dilution of 1:1,600. Two additional genotype 5a sera, SA1 and SA3, showed >50% neutralization at a dilution of 1:25,600 and 1:6,400, respectively. Thus, sera of patients chronically infected with genotype 5a had relatively high titers of neutralizing antibodies against a homologous 5a/JFH1 virus.

To rule out unspecific inhibition by serum factors, neutralizations with purified IgG from the SA3 serum was performed. A dose dependent neutralization yielding a 97% inhibition at 40 μg of SA3 IgG and >50% neutralization with 1.25 μg IgG (FIG. 12B) was shown. The present inventors also investigated neutralization of IgG purified in parallel from chronic phase serum of genotype 1a patient H(H06), which neutralized SA13/JFH1 with a 50% neutralization titer of 1:25,600, a potency mirrored by 98% inhibition at 40 μg IgG and >50% inhibition at 0.625 μg IgG (the lowest amount tested) (FIG. 12B).

Example 9

Cross-Genotype Neutralization Potential of Genotype 5a Sera

The inventors of the present invention found that chronic phase sera from genotype 1a and 4a infected patients could cross-neutralize intergenotypic recombinant viruses of genotype 1a, 4a, 5a and 6a, but failed to neutralize recombinants of genotype 2a and 3a. Thus, the ability of 5a sera (SA1, SA3, SA13, two-fold dilutions starting at 1:100) to cross-neutralize intergenotypic recombinants of the different genotypes were examined. The SA1 serum had the highest reciprocal 50% cross-neutralization titers, being 1,600, 400 and >51,200 against genotype 1a, 4a, and 6a viruses, respectively (Table 10). The SA3 and SA13 sera had limited or no cross-neutralization activity against genotype 1a and 4a viruses, but both sera had relative high titers of neutralizing antibodies against the 6a virus (Table 10). The 5a sera had no detectable cross-neutralizing activity against the genotypes 2a and 3a viruses at the 1:100 dilution. However, when subsequently testing a 1:50 dilution of the SA1 serum, which had the highest homologous neutralization titer, the inventors of the present invention observed >50% neutralization of the genotype 2a and 3a viruses (data not shown).

Example 10

Treatment with Homologous Neutralizing Antibodies Fails to Prevent SA13/JFH1 Spread In Vitro To investigate the treatment potential of neutralizing antibodies in vitro, the present inventors used SA3 serum because of its availability and a relatively high 50% neutralizing titer (1:6,400) against SA13/JFH1. As shown in FIG. 12C, 1:50 diluted SA3 serum had a strong neutralizing effect that, however, decreased with increasing doses of SA13/JFH1$_{C3405G-A3696G}$ virus (SEQ ID NO: 55); thus, 50, 100, 200, 400 and 800 TCID$_{50}$ were neutralized with 97%, 97%, 86%, 90% and 88% efficacy, respectively. ~100 and ~50 TCID$_{50}$ SA13/JFH1$_{C3405G-A3696G}$ was used, pre-incubated with SA3 serum at a 1:200 (FIG. 13A) or a 1:50 (FIG. 13B) dilution, respectively, to infect Huh7.5 cells. Subsequently, cells were treated with SA3 serum containing medium every 24 hours; the reciprocal 50% neutralization titer was ~32 (1:200 dilution) and ~128 (1:50 dilution), respectively.

Even though there was observed a delay in infection kinetics in both SA3 treated cultures compared to serum control (and virus only control), these cultures also became fully infected after 10 days (FIGS. 13A and B). The consensus sequence of the envelope genes of released viruses at day 11 showed evidence of quasispecies at one position in HVR1 of E2 (C1500T/C) encoding amino acid change T386I in the culture treated with the lowest neutralizing antibody dose; in clonal analysis this mutation was only seen in one of 3 clones. Furthermore, changes in the consensus sequence of genomes recovered at day 10 during treatment with the four-fold higher neutralizing antibody dose could not be detected. During treatment with the higher dose (FIG. 13B), supernatant infectivity titers at day 2 and 4 were <10$^{1.7}$ TCID$_{50}$/mL. At day 7, the titer had increased to 10$^{2.7}$ TCID$_{50}$/mL, still lower than the titer of the control cultures. However, at day 9 similar infectivity titers for both treated and control cultures (FIG. 13B) was found. Thus, treatment of HCV with homologous neutralizing antibodies did not appear to prevent viral spread in culture.

Example 11

Use of the 5a/JFH1 System in Drug Testing; Treatment with Inf-α 2b has an Antiviral Effect In Vitro To investigate the use of the 5a/JFH1 system to test antiviral drugs, the present inventors applied the antiviral drug IFN-α 2b, which is a constituent of the currently used combination therapy (IFN-α and Ribavirin) against HCV, to 5a/JFH1 infected cell cultures (FIG. 14). Huh7.5 cells were infected with 5a/JFH1 (MOI 0.003). On day 5, when 90% of the cultured cells were infected, treatment was commenced with 500 IU/mL IFN-α applied 3 times within the first 24 hours, then daily up to day 4, afterwards every 1-2 days. Within the first 3 days of treatment, the percent infected cells decreased dramatically and was kept below 5% within 10 days.

Tables

TABLE 1

Primers used for reverse transcription of extracted virus RNA.

| Primer | Primer sequence |
|---|---|
| SA13.1R901 (SEQ ID NO 3) | 5'-GACAGTCAGGCATGAAAGAAGTG-3' |
| SA13seqR4524 (SEQ ID NO 4) | 5'-GCAGAAGATGAGATGCCTAC-3' |
| SA13R4745 (SEQ ID NO 5) | 5'-GTG GTG TTG CAG TCT ATG ACA GAA TCA AAG TCG CCG GTA AAC-3' |
| 9470R(24)_JFH1 (SEQ ID NO 6) | 5'-CTATGGAGTGTACCTAGTGTGTGC-3' |
| SA13R9488 (SEQ ID NO 7) | 5'-<u>ATGCAT</u>CAGGAGTTATGGAGTGTTTAGC TCCCAGC-3' |
| SA13R9824 (SEQ ID NO 8) | 5'-TCATGCGGCTCACGGACCTTTCACAGCTAG-3' |

Underlined: Restriction sites (NsiI).

TABLE 2

Primers for amplification of PCR fragments used for determination of SA13 consensus sequence and for generation of SA13/JFH1 recombinant.

| Primer | Primer sequence |
|---|---|
| SA13F1 (SEQ ID NO 9) | 5'-<u>GCGGCCGC</u>TAATACGACTCACTATAGACCCGCCCCTTAT TGGGGCGACAC TCCACCATG-3' |
| SA13.1R901 (SEQ ID NO 3) | 5'-GACAGTCAGGCATGAAAGAAGTG-3' |

TABLE 2-continued

Primers for amplification of PCR fragments used for determination of SA13 consensus sequence and for generation of SA13/JFH1 recombinant.

| Primer | Primer sequence |
| --- | --- |
| SA13JFH1F341 (SEQ ID NO 10) | 5'-ATGAGCACGAATCCTAAACCTCAAAGAAAAACCAAAAG-3' |
| SA13JFH1 R1909 (SEQ ID NO 11) | 5'-CTTGCGGTCTGTGGTGCCGACGAC-3' |
| SA13JFH1 F1827 (SEQ ID NO 12) | 5'-GAA TAGTGCCAGCCCGAGGTGTCTGCG-3' |
| SA13JFH1 R3421 (SEQ ID NO 13) | 5'-GAGAAGTCGCCAGCCCGCCTCTCTGATG-3' |
| SA13R4745 (SEQ ID NO 4) | 5'-GTG GTG TTG CAG TCT ATG ACA GAA TCA AAG TCG CCG GTA AAC-3' |
| SA13.2F2818 (SEQ ID NO 14) | 5'-CTTACAATCTTCACACTCAC-3' |
| SA13seqR3987 (SEQ ID NO 15) | 5'-TGTGCTGTTGTCAGTGAACAC-3' |
| SA13F3934 (SEQ ID NO 16) | 5'-GCGGCCGCGGTGTCGCGAAGGCGCTCGATTTCATTCC-3' |
| SA13R9488 (SEQ ID NO 17) | 5'-ATGCATCAGGAGTTATGGAGTGTTTAGCTCCCAGC-3' |
| SA13F9223 (SEQ ID NO 18) | 5'-GCCGCCATCTGCGGCATCTATCTCTTCAACTG-3' |
| SA13R9824 (SEQ ID NO 8) | 5'-TCATGCGGCTCACGGACCTTTCACAGCTAG-3' |
| SA13F9259 (SEQ ID NO 19) | 5'-GCGGCCGCGTGAAAACAAAGCGCAAACTCACTCCATTAGCTGACG-3' |
| SA13R9811 (SEQ ID NO 20) | 5'-GGACCTTTCACAGCTAGCCGTGACTAGGG-3' |

Italics: T7 promoter.
Underlined: Restriction sites (NotI, NsiI).

TABLE 3

Primers for long RT-PCR and for nested PCR of 12 overlapping fragments of SA13/JFH1 for direct sequencing.

| | Primer | Primer sequence |
| --- | --- | --- |
| 1st Round PCR | -285S_HCV-MOD (SEQ ID NO 21) | 5'-ACTGTCTTCACGCAGAAAGCGCCTAGCCAT-3' |
| | 9470R(24)_JFH1 (SEQ ID NO 6) | 5'-CTATGGAGTGTACCTAGTGTGTGC-3' |
| 2nd Round PCR | | |
| Product 1 | -84S_HCV-MOD (SEQ ID NO 22) | 5'-GTAGCGTTGGGTTGCGAAAGGCCTTGTGGTACTGCCTGAT-3' |
| | SA13.1 seqR1443 (SEQ ID NO 23) | 5'-CAGTTAGCCGCCGACGCGTAGTATG-3' |
| Product 2 | Chim seq F809 (SEQ ID NO 24) | 5'-GTCCTTGAGGACGGGGTAAACTATGCAACAG-3' |
| | SA13JFH1 R1987 (SEQ ID NO 25) | 5'-CTTGACAAACCCTGTGGAATTCATCCAGGTGCAGCCAAACCAG-3' |
| Product 3 | SA13JFH1 F1827 (SEQ ID NO 12) | 5'-GAA TAGTGCCAGCCCGAGGTGTCTGCG-3' |
| | SA13 R2525 (SEQ ID NO 26) | 5'-CATAGTGCTGGCCTTCTTATTACTTGCTG-3' |

TABLE 3-continued

Primers for long RT-PCR and for nested PCR of 12 overlapping fragments of SA13/JFH1 for direct sequencing.

| | Primer | Primer sequence |
|---|---|---|
| Product 4 | SA13.2 seqF2327 (SEQ ID NO 27) | 5'-CTGAGCCCGCTCCTACATACCAC-3' |
| | SA13 R3432 (SEQ ID NO 28) | 5'-CAGAGAGGCGGGCTGGCGACTTCTCGCTCCCATCAC-3' |
| Product 5 | SA13 F3246 (SEQ ID NO 29) | 5'-GCAGTGGCCACGGAGCCCATCATATTCTC-3' |
| | 4118R_JFH1 (SEQ ID NO 30) | 5'-CGCCCGAGGCCTACCTCTTCTATATC-3' |
| Product 6 | 3880S_J6 (SEQ ID NO 31) | 5'-CCCATCACGTACTCCACATATGGC-3' |
| | 4796R_JFH1 (SEQ ID NO 32) | 5'-GCGCACACCGTAGCTTGGTAGG-3' |
| Product 7 | 4528S_J6 (SEQ ID NO 33) | 5'-GAGCGAGCCTCAGGAATGTTTGACA-3' |
| | 5446R_JFH1 (SEQ ID NO 34) | 5'-TGATGTTGAGAAGGATGGTGGTAC-3' |
| Product 8 | 5272S_JFH1 (SEQ ID NO 35) | 5'-TGGCCCAAAGTGGAACAATTTTGG-3' |
| | 6460R_J6 (SEQ ID NO 36) | 5'-CAACGCAGAACGAGACCTCATCCC-3' |
| Product 9 | 6186S_JFH1 (SEQ ID NO 37) | 5'-GACCTTTCCTATCAATTGCTACAC-3' |
| | 7234R_JFH1 (SEQ ID NO 38) | 5'-GAAGCTCTACCTGATCAGACTCCA-3' |
| Product 10 | 6862S_JFH1 (SEQ ID NO 39) | 5'-TGGGCACGGCCTGACTACAA-3' |
| | 7848R_JFH1 (SEQ ID NO 40) | 5'-GGCCATTTTCTCGCAGACCCGGAC-3' |
| Product 11 | 7741S_J6 (SEQ ID NO 41) | 5'-ATGGCCAAAAATGAGGTGTTCTGC-3' |
| | 8703R_JFH1 (SEQ ID NO 42) | 5'-AAGGTCCAAAGGATTCACGGAGTA-3' |
| Product 12 | 8137S_JFH1 (SEQ ID NO 43) | 5'-GGTCAAACCTGCGGTTACAGACGTTG-3' |
| | 9464R(24)_JFH1 (SEQ ID NO 44) | 5'-GTGTACCTAGTGTGTGCCGCTCTA |

TABLE 4

Primers used for the construction of pSA13/JFH1.

| | |
|---|---|
| SA13JFH1 F11451 (SEQ ID NO 45) | 5'-GTGTATGCGGCGACCGAGTTGCTCTTG-3' |
| SA13JFH1 R361 (SEQ ID NO 46) | 5'-AGGTTTAGGATTCGTGCTCATGGTGCACGGTCTACGAGACCTC-3' |
| SA13JFH1F341 (SEQ ID NO 47) | 5'-ATGAGCACGAATCCTAAACCTCAAAGAAAAACCAAAG-3' |
| SA13JFH1 R1909 (SEQ ID NO 11) | 5'-CTTGCGGTCTGTGGTGCCGACGAC-3' |

TABLE 4-continued

Primers used for the construction of pSA13/JFH1.

| | |
|---|---|
| SA13JFH1 F1827 (SEQ ID NO 12) | 5'-GAA TAGTGCCAGCCCGAGGTGTCTGCG-3' |
| SA13JFH1 R3421 (SEQ ID NO 13) | 5'-GAGAAGTCGCCAGCCCGCCTCTCTGATG-3' |
| SA13JFH1 F3422 (SEQ ID NO 48) | 5'-ATCAGAGAGGCGGGCTGGCGACTTCTCGCTCCC ATCACTGCTTATGCCCAGCA-3' |
| SA13JFH1 R4141 (SEQ ID NO 49) | 5'-GGATTGATGCCATGTGCCTTGGATAGGTAC-3' |
| ppSA13F823 (SEQ ID NO 50) | 5'-GTAAACTATGCAACAGGGAATTTACCCGGTTGCTCT TTCTCTATCTTTATCCTTGCAC-3' |
| ppSA13R1915 (SEQ ID NO 51) | 5'-GAT TCC CCT TGC GGT CTG TGG TGC CGA CGA-3' |

Bold: SA13 sequence overhang.

TABLE 5

Primers used for introduction of C3405G mutation in pSA13/JFH

| | |
|---|---|
| SA13F3380-3405G (SEQ ID NO 52) | 5'-GGGCCAGCCGATGACATCAGAGAGGGGGCTGGCGACTTCT-3' |
| 4118R_JFH1 (SEQ ID NO 30) | 5'-CGCCCGAGGCCTACCTCTTCTATATC-3' |
| SA13JFH1 F1827 (SEQ ID NO 12) | 5'-GAA TAGTGCCAGCCCGAGGTGTCTGCG-3' |
| SA13R3430-3405G (SEQ ID NO 53) | 5'-GATGGGAGCGAGAAGTCGCCAGCCCCCCTCTCTGATGTCATC-3' |
| SA13JFH1 F 1827 (SEQ ID NO 12) | 5'-GAA TAGTGCCAGCCCGAGGTGTCTGCG-3' |
| SA13muta A3696G R (SEQ ID NO 60) | 5'-CACTTGCACGGCTCCAAAGACCTGGTCCCAG-3' |
| 4118R_JFH1 (SEQ ID NO 30) | 5'-CGCCCGAGGCCTACCTCTTCTATATC-3' |
| SA13muta A3696G F (SEQ ID NO 61) | 5'-CCAGCCCCCCTGGGACCAGGTCTTTGGAG-3' |
| SA13JFH1 F 1827 (SEQ ID NO 12) | 5'-GAA TAGTGCCAGCCCGAGGTGTCTGCG-3' |
| SA13muta G2611T R (SEQ ID NO 62) | 5'-ATGAGTCCCCGCAGCCGCAGCAGCGTTTAGGAC-3' |

TABLE 5-continued

Primers used for introduction of C3405G mutation in pSA13/JFH

| | |
|---|---|
| SA13muta G2611T F (SEQ ID NO 63) | 5'-GAACGTCATTGTCCTAAACGCTGCTGCGGCTG-3' |
| SA13muta A2728G R (SEQ ID NO 64) | 5'-CAGGAGGAAAAGGAGTAAGAGTAACGGCCAAATG-3' |
| SA13muta A2728G F (SEQ ID NO 65) | 5'-TTGCTTGGGCATTTGGCCGTTACTCTTACTCC-3' |
| SA13muta A3696G R (SEQ ID NO 60) | 5'-CACTTGCACGGCTCCAAAGACCTGGTCCCAG-3' |
| 4118R_JFH1 (SEQ ID NO 30) | 5'-CGCCCGAGGCCTACCTCTTCTATATC-3' |
| SA13muta A3696G F (SEQ ID NO 61) | 5'-CCAGCCCCCCTGGGACCAGGTCTTTGGAG-3' |

TABLE 6

Comparison of infectious titers (TCID$_{50}$) and HCV RNA titers of cell culture derived SA13/JFH1 and J6/JFH viruses. Infectious titers (TCID$_{50}$) and HCV RNA titers were determined as described in Materials and Methods. Specific infectivity was determined as infectious dose (TCID$_{50}$/ml) per genomes (IU/ml).

| Supernatant | Day | TCID$_{50}$ per ml SA13/JFH1 | TCID$_{50}$ per ml J6/JFH | HCV RNA titers (IU/ml) SA13/JFH1 | HCV RNA titers (IU/ml) J6/JFH | Specific infectivity SA13/JFH1 | Specific infectivity J6/JFH |
|---|---|---|---|---|---|---|---|
| Transfection | day 3 | <10$^{1.3}$* | 10$^{3.1}$ | | | | |
| | day 10 | 10$^{2.3}$ | 10$^{3.7}$ | | | | |
| | day 13 | 10$^{3.6}$ | NT | | | | |
| | day 15 | 10$^{3.3}$ | NT | | | | |
| 1$^{st}$ Passage A | day 3 | 10$^{3.3}$ | 10$^{3.3}$ | 10$^{6.3}$ | 10$^{6}$ | 1:1000 | 1:501 |
| 2$^{nd}$ Passage A | day 1 | 10$^{2.2}$ | 10$^{2.4}$ | 10$^{4.4}$ | 10$^{4.5}$ | 1:158 | 1:126 |
| | day 3 | 10$^{4.2}$ | 10$^{4.2}$ | 10$^{6.6}$ | 10$^{6.3}$ | 1:251 | 1:126 |
| | day 5 | 10$^{5.2}$ | 10$^{4.9}$ | 10$^{7.6}$ | 10$^{7.5}$ | 1:251 | 1:398 |
| | day 7 | 10$^{4.9}$ | 10$^{5.2}$ | 10$^{7.7}$ | 10$^{7.4}$ | 1:631 | 1:158 |
| 1$^{st}$ Passage B | day 7 | 10$^{4.2}$ | 10$^{4.3}$ | 10$^{6.9}$ | 10$^{6.9}$ | 1:501 | 1:398 |
| 2$^{nd}$ Passage B | day 6 | 10$^{4.3}$ | NT | 10$^{6.9}$ | 10$^{6.3}$ | 1:398 | |
| | day 8 | 10$^{4.7}$ | NT | 10$^{7.0}$ | 10$^{6.7}$ | 1:200 | |

NT: not tested.
*Transfection day 3 for SA13/JFH1 was scored as <10$^{1.3}$ TCID$_{50}$/ml as only one of 6 wells was positive in the titration assay at a 10$^{-1}$ dilution and the undiluted sample has not yet been tested.

TABLE 7

Inocula used for 1$^{st}$ and 2$^{nd}$ passage experiments of SA13/JFH1 and J6/JFH. Supernatants from the transfection were used to inoculate naive Huh7.5 cells for a 1$^{st}$ passage in two independent experiments and 1$^{st}$ passage supernatants were used to inoculate naive cells for their respective 2$^{nd}$ passages. The supernatants are characterized by the day rescued from cell culture, the percentage of infected cells in this cell culture at that day and the infectious dose of the inoculum. The percentage of infected cells and the TCID$_{50}$ were determined as described in Materials and Methods.

| Transfection supernatant passed to: | Recipient culture: 1$^{st}$ Passage A % infected cells | TCID$_{50}$ | Recipient culture: 1$^{st}$ Passage B % infected cells | TCID$_{50}$ | supernatant passed to: | Recipient culture: 2$^{nd}$ Passage A % infected cells | TCID$_{50}$ | Recipient culture: 2$^{nd}$ Passage B % infected cells | TCID$_{50}$ |
|---|---|---|---|---|---|---|---|---|---|
| SA13/JFH1 | Day 15 80% | 10$^{3.3}$ | Day 13 80% | 10$^{3.6}$ | SA13/JFH1 | Day 3 100% | 10$^{3.3}$ | Day 7 95% | 10$^{4.2}$ |
| J6/JFH | Day 8 80% | 10$^{3.1}$ | Day 8 80% | 10$^{3.1}$ | J6/JFH | Day 3 100% | 10$^{3.3}$ | Day 7 95% | 10$^{4.3}$ |
| SA13/JFH1-GND | Day 8 0% | — | Day 8 0% | — | SA13/JFH1-GND | Day 3 0% | — | Day 7 0% | — |

1$^{st}$ Passage

TABLE 8A

Putative adaptive mutations in serially passed SA13/JFH1 determined by direct sequencing and clonal analysis. A: The table shows the nucleotide positions on the SA13/JFH1 genome with detected heterogeneity and in which HCV gene the mutation is located. To standardize numbering of HCV sequence and proteins it has been proposed to use the sequence of H77 (AF009606) as a reference strain, which is showed in the rows below the SA13/JFH1 sequence (Kuiken et al., 2006). The specific nucleotide at a particular position is given as a capital or lower case letter: The first letter represents the original nucleotide of pSA13/JFH1 and the second letters shows the mutated nucleotide at that position. Capital letters show the presence of one determinate sequence peak at the respective nucleotide position. Two capital letters separated by a slash show the presence of a quasispecies in a 50/50 distribution, whereas a capital separated by a slash from a lowercase letter showes a quasispecies with a predominant versus a minor sequence at the given position. To determine the combination of mutations on individual virus genomes, PCR on cDNA from the $2^{nd}$ passage A day 7 was performed to obtain nucleotides 56-7371. The PCR fragments were subcloned and 10 clones were sequenced. B: Amino acid positions correlating to nucleotide positions in A.

A

| Nucleotid position SA13/JFH1 | 2611 | 2728 | 3405 | 3696 | 6839 |
|---|---|---|---|---|---|
| Nucleotid position H77 | 2609 | 2726 | 3403 | 3694 | 6837 |
| Gene | p7 | p7 | NS2 | NS3 | NS5A |
| pSA13/JFH1 | G | A | C | A | C |
| Direct sequencing of SA13/JFH1 viruses | | | | | |
| $1^{st}$ Passage B, day 7 | G/t | A/g | C/G | A/g | C/t |
| $2^{nd}$ Passage A, day 7 | G/t | A/g | C/G | A/g | C/t |
| $2^{nd}$ Passage B, day 8 | G/T | A/G | C/G | A/G | C/t |
| Clones of SA13/JFH1 2nd passage A | | | | | |
| Clone 1 | G | A | C | A | C |
| Clone 2 | T | G | G | G | C |
| Clone 3 | G | A | C | A | C |
| Clone 4 | T | G | G | G | C |
| Clone 5 | T | G | G | G | C |
| Clone 6 | T | A | C | A | C |
| Clone 7 | T | G | G | G | C |
| Clone 8 | G | A | C | A | C |
| Clone 9 | G | A | C | A | C |
| Clone 10 | T | G | G | G | C |

B

| Aminoacid position SA13/JFH1 | 757 | 796 | 1022 | 1119 | 2167 |
|---|---|---|---|---|---|
| Aminoacid position H77 | 756 | 795 | 1021 | 1118 | 2166 |
| pSA13/JFH1 | Ala | Pro | Ala | Lys | Pro |
| $1^{st}$ Passage B, day 7 | Ala | Pro | Ala/Gly | Lys/arg | Pro/ser |
| $2^{nd}$ Passage A, day 7 | Ala | Pro | Ala/Gly | Lys/arg | Pro/ser |
| $2^{nd}$ Passage B, day 8 | Ala | Pro | Ala/Gly | Lys/Arg | Pro/ser |
| Clones of SA13/JFH1 2nd passage A | | | | | |
| Clone 1 | Ala | Pro | Ala | Lys | Pro |
| Clone 2 | Ala | Pro | Gly | Arg | Pro |
| Clone 3 | Ala | Pro | Ala | Lys | Pro |
| Clone 4 | Ala | Pro | Gly | Arg | Pro |
| Clone 5 | Ala | Pro | Gly | Arg | Pro |
| Clone 6 | Ala | Pro | Ala | Lys | Pro |
| Clone 7 | Ala | Pro | Gly | Arg | Pro |
| Clone 8 | Ala | Pro | Ala | Lys | Pro |
| Clone 9 | Ala | Pro | Ala | Lys | Pro |
| Clone 10 | Ala | Pro | Gly | Arg | Pro |

TABLE 8B

Mutations of SA13/JFH1(SEQ ID NO 1), SA13/JFH1-C3405G (SEQ ID NO 54), SA13/JFH1-C3405G-A3696G (SEQ ID NO 55) and SA13/JFH1-G2611T-A2728G-C3405G-A3696G (SEQ ID NO 56) recovered from cell culture supernatants.

A. Nucleotide changes

| Nucleotide position SA13/JFH1 | 2405 | 2611 | 2728 | 3405 | 3623 | 3696 | 3954 | 4277 | 4801 | 4972 | 6538 |
|---|---|---|---|---|---|---|---|---|---|---|---|
| Nucleotide position H77[a] | 2403 | 2609 | 2726 | 3403 | 3621 | 3694 | 3952 | 4275 | 4799 | 4970 | 6536 |
| Gene | E2 | p7 | p7 | NS2 | NS3 | NS3 | NS3 | NS3 | NS3 | NS3 | NS5A |
| pSA13/JFH1 | G | G | A | C | C | A | T | A | G | C | C |

Transfection experiment with SA13/JFH1

Direct sequencing of SA13/JFH1 viruses

| | | | | | | | | | | | |
|---|---|---|---|---|---|---|---|---|---|---|---|
| 1st Passage, day 7 | — | G/t | A/g | C/G | — | A/g | — | — | — | — | — |
| 2nd Passage, day 7[b,c] | — | G/t | A/g | C/G | — | A/g | — | — | — | — | — |
| 2nd Passage, day 8 | — | G/T | A/G | C/G | — | A/G | — | — | — | — | — |

2nd passage clonal distribution[b]

| | | | | | | | | | | | |
|---|---|---|---|---|---|---|---|---|---|---|---|
| 3/10 | — | — | — | — | — | — | — | — | — | — | — |
| 2/10 | — | T | G | G | — | G | — | — | — | — | — |
| 2/10 | A | T | G | G | — | G | — | — | — | — | — |
| 1/10 | — | T | G | G | — | G | — | — | A[d] | — | — |
| 1/10 | — | T | — | — | — | — | — | — | — | — | — |
| 1/10 | — | — | — | — | — | — | — | — | T[d] | — | — |

1st Transfection experiment with mutated SA13/JFH1

Direct sequencing, 1st Passage day 6

| | | | | | | | | | | | |
|---|---|---|---|---|---|---|---|---|---|---|---|
| SA13/JFH1 | — | — | — | — | C/T | — | — | — | — | C/T | — |
| SA13/JFH1_{C3405G} | — | — | — | G[e] | — | — | T/C | — | — | — | — |

2nd Transfection experiment with mutated SA13/JFH1

Direct sequencing, 1st Passage day 3

| | | | | | | | | | | | |
|---|---|---|---|---|---|---|---|---|---|---|---|
| SA13/JFH1 | — | — | — | — | — | — | — | A/G | — | — | — |
| SA13/JFH1_{C3405G} | — | — | — | G[e] | — | — | — | — | — | — | — |
| SA13/JFH1_{C3405G-A3696G}[f] | — | — | — | G[e] | — | G[e] | — | — | — | — | — |
| SA13/JFH1_{G2611T-A2728G-C3405G-A3696G} | — | T[e] | G[e] | G[e] | — | G[e] | — | — | — | — | c/T |

B. Positions with amino acid changes

| Amino acid position SA13/JFH1 | 1022 | 1095 | 1119 | 1205 | 1313 | 1487 |
|---|---|---|---|---|---|---|
| Amino acid position H77 | 1021 | 1094 | 1118 | 1204 | 1312 | 1486 |
| SA13/JFH1 | Ala | Arg | Lys | Val | Ile | Gln |
| Change | Gly | Trp | Arg | Ala | Val | His |

Nucleotide or amino acid positions refer to SA13/JFH1 (SEQ ID NO 1). Capital and lower case letters indicate a dominant or non-dominant nucleotide, respectively; two capital letters indicates that a dominant sequence was not determinable. Mutations representing at least a 50/50 percent distribution in one passage are shown.
[a]Nucleotide or amino acid positions refer to the H77 reference strain (Accession number AF009606).
[b]In one of two independent 2nd passages, clonal analysis was performed. Only nucleotide changes found at the same positions in at least 2 clones are shown. Additionally, in all analyzed clones, mutations occurring in only one clone were found.
[c]Used in neutralization assay (FIG. 12A).
[d]G4801A, non-coding; and G4801T, coding.
[e]Mutation introduced into SA13/JFH1.
[f]Used in virus treatment experiments, neutralization assay (FIG. 12A and C), anti-CD81 and SR-BI experiments (FIG. 11A and B) (SEQ ID NO 55).

TABLE 9

Infectivity titers (TCID$_{50}$) determined for SA13/JFH1(SEQ ID NO 1), C3405G-SA13/JFH1 (SEQ ID NO 54), C3405G-A3696G-SA13/JFH1 (SEQ ID NO 55), G2611T-A2728G-C3405G-A3696G-SA13/JFH1 (SEQ ID NO 56) and FL-J6/JFH cultures on day 3.

| TCID$_{50}$ | Day 3 |
|---|---|
| SA13/JFH1 | $10^{2.2}$ TCID$_{50}$/ml |
| C3405G-SA13/JFH1 | $10^{3.9}$ TCID$_{50}$/ml |
| C3405G-A3696G-SA13/JFH1 | $10^{4.1}$ TCID$_{50}$/ml |
| G2611T-A2728G-C3405G-A3696G-SA13/JFH1 | $10^{4.3}$ TCID$_{50}$/ml |
| J6/JFH | $10^{4.1}$ TCID$_{50}$/ml |

TABLE 10

Neutralization of JFH1-based HCV recombinants of genotypes 1-6 with genotype 5a sera.

| | Envelope genotype of JFH1-based recombinants | | | | | |
|---|---|---|---|---|---|---|
| | 1a | 2a | 3a | 4a | 5a | 6a |
| | Reciprocal 50% neutralization titer | | | | | |
| SA1 serum | 1,600 | <100 | <100 | 400 | 25,600 | >51,200 # |
| SA3 serum | <100 | <100 | <100 | 200 | 6,400 | 12,800 |

TABLE 10-continued

Neutralization of JFH1-based HCV recombinants of genotypes 1-6 with genotype 5a sera.

| | Envelope genotype of JFH1-based recombinants | | | | | |
|---|---|---|---|---|---|---|
| | 1a | 2a | 3a | 4a | 5a | 6a |
| | Reciprocal 50% neutralization titer | | | | | |
| SA13 serum | <100 | <100 | <100 | <100 | 1,600 | 3,200 |

Neutralization of HCV was performed against 100-200 $TCID_{50}$ of JFH1-based recombinants containing Core-NS2 of genotypes 1-6. The recombinant viruses were incubated in triplicates with 2-fold serial dilutions of chronic phase sera of patients infected with HCV genotype 5a (SA1, SA3 and SA13) or 2-fold serial dilutions of a control serum mixture before testing on Huh7.5 cells. Reciprocal neutralization titers were determined as the highest serum dilution showing a reduction of 50% FFUs compared to the average FFUs counts for the control serum. The average FFUs in the controls in the different genotype experiments ranged from 10 to 70 FFUs/well. In control serum experiments for a particular genotype there was no significant difference in the FFU counts between the different dilutions (data not shown). [a] Neutralization ~75% at a 1:51, 200 dilution.

REFERENCES

Bukh, J., Purcell, R. H., and Miller, R. H. (1993). At least 12 genotypes of hepatitis C virus predicted by sequence analysis of the putative E1 gene of isolates collected worldwide. Proc Natl Acad Sci USA 90, 8234-8238.

Kato, T.; Furusaka, A.; Miyamoto, M.; Date, T.; Yasui, K.; Hiramoto, J.; Nagayama, K.; Tanaka, T.; Wakita, T. (2001). Sequence analysis of hepatitis C virus isolated from a fulminant hepatitis patient. J Med. Virol. 64, 334-339

Kato, T., Date, T., Miyamoto, M., Furusaka, A., Tokushige, K., Mizokami, M., and Wakita, T. (2003). Efficient replication of the genotype 2a hepatitis C virus subgenomic replicon. Gastroenterology. 125, 1808-1817.

Lindenbach, B. D., Evans, M. J., Syder, A. J., Wolk, B., Tellinghuisen, T. L., Liu, C. C., Maruyama, T., Hynes, R. O., Burton, D. R., McKeating, J. A., and Rice, C. M. (2005). Complete replication of hepatitis C virus in cell culture. Science. 309, 623-626.

Lindenbach, B. D., Meuleman, P., Ploss, A., Vanwolleghem, T., Syder, A. J., McKeating, J. A., Lanford, R. E., Feinstone, S. M., Major, M. E., Leroux-Roels, G., and Rice, C. M. (2006). Cell culture-grown hepatitis C virus is infectious in vivo and can be recultured in vitro. Proc. Natl. Acad. Sci. U.S.A. 103, 3805-3809.

Meunier, J. C. et al. (2005) Evidence for Cross-Genotype Neutralization of Hepatitis C Virus Pseudo-Particles and Enhancement of Infectivity by Apolipoprotein C1 *Proc Natl Acad Sci USA* 102, 4560-4565.

TABLE 11

Primer pairs used to analyse for virus escape in treatment experiments (FIG. 13A and B)

| | Primer | Primer sequence |
|---|---|---|
| 1st Round PCR | -285S_HCV-MOD (SEQ ID NO 21) | 5'-ACTGTCTTCACGCAGAAAGCGCCTAGCCAT-3' |
| | 9470R(24)_JFH1 (SEQ ID NO 6) | 5'-CTATGGAGTGTACCTAGTGTGTGC-3' |
| 2nd Round PCR | | |
| Product 1 | -84S_HCV-MOD (SEQ ID NO 22) | 5'-GTAGCGTTGGGTTGCGAAAGGCCTTGTGGT ACTGCCTGAT-3' |
| | SA13.1 seqR1443 (SEQ ID NO 23) | 5'-CAGTTAGCCGCCGACGCGTAGTATG-3' |
| Product 2 | Chim seq F809 (SEQ ID NO 24) | 5'-GTCCTTGAGGACGGGGTAAACTATGCAACAG-3' |
| | SA13JFH1 R1987 (SEQ ID NO 25) | 5'-CTTGACAAACCCTGTGGAATTCATCCAGGTGCAG CCAAACCAG-3' |
| Product 3 | SA13JFH1 F1827 (SEQ ID NO 12) | 5'-GAA TAGTGCCAGCCCGAGGTGTCTGCG-3' |
| | SA13 R2525 (SEQ ID NO 26) | 5'-CATAGTGCTGGCCTTCTTATTACTTGCTG-3' |
| Product 4 | SA13.2 seqF2327 (SEQ ID NO 27) | 5'-CTGAGCCCGCTCCTACATACCAC-3' |
| | SA13 R3432 (SEQ ID NO 28) | 5'-CAGAGAGGCGGGCTGGCGACTTCTCGCTCCCATCAC-3' |

Pietschmann, T., Kaul, A., Koutsoudakis, G., Shavinskaya, A., Kallis, S., Steinmann, E., Abid, K., Negro, F., Dreux, M., Cosset, F. L., and Bartenschlager, R. (2006). Construction and characterization of infectious intragenotypic and 30 intergenotypic hepatitis C virus chimeras. Proc. Natl. Acad. Sci. U.S. A 103, 7408-7413.

Wakita, T., Pietschmann, T., Kato, T., Date, T., Miyamoto, M., Zhao, Z., Murthy, K., Habermann, A., Krausslich, H. G., Mizokami, M., Bartenschlager, R., and Liang, T. J. (2005). Production of infectious hepatitis C virus in tissue culture from a cloned viral genome. Nat. Med. 11, 791-796.

Zhong, J., Gastaminza, P., Cheng, G., Kapadia, S., Kato, T., Burton, D. R., Wieland, S. F., Uprichard, S. L., Wakita, T., and Chisari, F. V. (2005). Robust hepatitis C virus infection in vitro. Proc. Natl. Acad. Sci. U.S.A. 102, 9294-9299.

The invention claimed is:

1. An isolated nucleic acid molecule comprising a nucleic acid sequence which encodes an amino acid sequence with a sequence identity of at least 92% to that of SEQ ID NO: 2, wherein said nucleic acid molecule encodes a genetically engineered human hepatitis C virus of genotype 5a/2a that comprises at least one adaptive mutation in the amino acid sequence of NS2 or NS3 selected from the group consisting of A1022G and K1119R, wherein the genotype 2a is strain JFH-1, and wherein said nucleic acid molecule is capable of producing said hepatitis C virus when said nucleic acid molecule is transfected into cells in vitro.

2. The nucleic acid molecule according to claim 1, wherein said nucleic acid molecule comprises a nucleic acid sequence with a sequence identity of at least 92% to that of SEQ ID NO: 1 and that is selected from the group consisting of double stranded DNA, complementary DNA (cDNA), positive-sense cDNA, negative-sense cDNA, positive-sense RNA, negative-sense RNA, and double stranded RNA, wherein said nucleic acid molecule comprises at least one adaptive mutation in the nucleic acid sequence encoding NS2 or NS3 selected from the group consisting of C3405G, G2611T, A2728G and A3696G.

3. The nucleic acid molecule according to claim 1, wherein the adaptive mutation is a mutation that can be observed by clonal or direct sequencing of recovered replicating genomes of SEQ ID NO: 1.

4. A composition comprising the nucleic acid molecule according to claim 1 and a pharmaceutically acceptable diluent or excipient.

5. A cassette vector comprising the nucleic acid molecule of claim 1 and an active promoter, wherein said nucleic acid sequence which encodes a human hepatitis C virus of genotype 5a/2a of the nucleic acid molecule is inserted in said cassette vector downstream of said active promoter.

6. A method for producing a cell comprising introducing a nucleic acid molecule into a cell, wherein said nucleic acid molecule comprises a nucleic acid sequence which encodes a genetically engineered human hepatitis C virus of genotype 5a/2a with at least 92% identity to that of SEQ ID NO: 1 and wherein said nucleic acid molecule comprises at least one adaptive mutation in the nucleic acid sequence encoding NS2 or NS3 selected from the group consisting of C3405G, G2611T, A2728G and A3696G, wherein the genotype 2a is strain TFH-1, and wherein said cell replicates hepatitis C virus genotype 5a/JFH1 and produces an infectious hepatitis C virus genotype 5a/JFH1 viral particle.

7. The method according to claim 6, wherein said cell is Huh7.5.

8. The method according to claim 6, further comprising culturing said cell to produce the hepatitis C virus genotype 5a/2a viral particle.

9. The method of claim 8, further comprising isolating the hepatitis C virus genotype 5a/2a viral particle.

10. The method of claim 6, further comprising culturing said hepatitis C virus genotype 5a/2a viral particle with other cells in vitro to produce a hepatitis C virus-infected cell.

11. The method of claim 10, further comprising isolating said hepatitis C virus infected cell.

12. A method for identifying an anti-hepatitis C virus substance, comprising:
  culturing a cell or viral particle that comprises the nucleic acid molecule of claim 1 with a hepatitis C virus permissive cell;
  contacting the cell or viral particle that comprises the nucleic acid molecule of claim 1 or the hepatitis C virus permissive cell with a substance; and detecting the replicating RNA or the virus particles in the culture, wherein a decrease in the level of HCV infection, replication or cell-to-cell spread indicates that the substance is an anti-hepatitis C virus substance.

13. The method of claim 12, wherein said nucleic acid molecule comprises a sequence with a sequence identity of at least 92% to that of SEQ ID NO: 1 and, wherein said nucleic acid comprises at least one adaptive mutation in the nucleic acid sequence encoding NS2 or NS3 selected from the group consisting of C3405G, G2611T, A2728G and A3696G.

14. An immunogenic composition comprising the nucleic acid molecule of claim 1.

15. The immunogenic composition of claim 14, wherein said nucleic acid molecule comprises a nucleic acid sequence with a sequence identity of at least 92% to that of SEQ ID NO: 1 and, wherein said nucleic acid molecule comprises at least one adaptive mutation in the nucleic acid sequence encoding NS2 or NS3 selected from the group consisting of C3405G, G2611T, A2728G and A3696G.

16. The nucleic acid molecule according to claim 1, wherein said nucleic acid molecule is capable of infectivity in vivo.

17. The nucleic acid molecule according to claim 1, wherein said nucleic acid molecule comprises the Core, E1, E2, p7, and NS2 genes of HCV genotype 5a, and the NS3, NS4A, NS4B, NS5A, and NS5B genes from the HCV JFH1 strain.

18. The nucleic acid molecule according to claim 1, wherein said nucleic acid molecule comprises the Core, E1, E2, p7, and NS2 genes of HCV genotype 5a, and the 5' untranslated region, NS3 gene, NS4A gene, NS4B gene, NS5A gene, NS5B gene, and 3' untranslated region from the HCV JFH1 strain.

19. The nucleic acid molecule according to claim 18, wherein said HCV genotype 5a strain is SA13.

20. The method according to claim 6, wherein said nucleic acid molecule comprises the Core, E1, E2, p7, and NS2 genes of HCV genotype 5a, and the NS3, NS4A, NS4B, NS5A, and NS5B genes from the HCV JFH1 strain.

21. The method according to claim 6, wherein said nucleic acid molecule comprises the Core, E1, E2, p7, and NS2 genes of HCV genotype 5a, and the 5' untranslated region, NS3 gene, NS4A gene, NS4B gene, NS5A gene, NS5B gene, and 3' untranslated region from the HCV JFH1 strain.

22. The method according to claim 21, wherein said HCV genotype 5a strain is SA13.

* * * * *

SEQUENCE LISTING

<160> NUMBER OF SEQ ID NOS: 65

<210> SEQ ID NO 1
<211> LENGTH: 9669
<212> TYPE: DNA
<213> ORGANISM: Hepatitis C virus

<400> SEQUENCE: 1

```
acctgcccct aatagggggcg acactccgcc atgaatcact cccctgtgag gaactactgt      60
cttcacgcag aaagcgccta gccatggcgt tagtatgagt gtcgtacagc ctccaggccc     120
cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttggttg cgaaaggcct tgtggtactg cctgataggg     300
cgcttgcgag tgccccggga ggtctcgtag accgtgcacc atgagcacga tcctaaacc      360
tcaaagaaaa accaaaagaa acaccaaccg ccgcccacag gacgtcaagt tcccgggcgg     420
tggtcagatc gttggtggag tttacttgtt gccgcgcagg ggcctaggt tgggtgtgcg      480
cgcaactcgg aagacttcag aacggtcgca accccgtgga cggcgtcagc ctatccccaa     540
ggcgcgccag cccacgggcc ggtcctgggg tcaacccggg taccttggc ccctttatgc      600
caatgagggc ctcgggtggg cagggtggtt gctctccccc cgaggctctc ggcctaattg     660
gggccccaat gaccccggc ggaaatcgcg caacttgggg aaggtcatcg atacctgac      720
gtgcggattc gccgacctca tgggtacat cccgctcgta ggcggccccg ttggggcgt      780
cgcaagggct ctcgcacacg tgtgagggt ccttgaggac ggggtaaact atgcaacagg     840
gaatttaccc ggttgctctt tctctatctt tatccttgca cttctttcat gcctgactgt     900
cccgacctct gccgttccct accgaaatgc ctctggggtt tatcatgtca ccaatgattg     960
cccaaactct tctatcgtct atgaggctga agacctgatc ttacacgcac ctggttgcgt    1020
gccctgtgtt aggcagggta atgtcagtag gtgctgggtc cagatcaccc ccacactgtc    1080
agccccgagc ctcggagcgg tcacggctcc tcttcggagg gccgttgact acttagcggg    1140
gggggctgcc ctttgctccg cgttatacgt cggagacgcg tgcgggcag tgttttggt     1200
aggtcaaatg ttcacctata gccctcgccg gcataatgtt gtgcaggact gcaactgttc    1260
catttacagt ggccacatca ccggccaccg gatggcatgg gacatgatga tgaattggtc    1320
acctacaaca gctttggtga tggcccagtt gttacgggatt ccccaggtgg tcattgacat    1380
cattgccggg gcccactggg gggtcttgtt cgccgccgca tactacgcgt cggcggctaa    1440
ctgggccaag gttgtgctgg tcctgtttct gtttgcgggg gtcgatgcca gcacccgcac    1500
tgtgggtggt agtgcggccc aaggcgcgcg cgggctcgct tcacttttca ccctgggcc     1560
gcagcagaac ttgcagctca taaataccaa cgggagctgg cacatcaaca gaactgccct    1620
taactgtaat gacagcctcc agactgggtt tgtagccggg ctcctgtatt atcacaagtt    1680
caactccact gggtgtccgc agcggatggc tagctgtagg ccctcgccg cattcgacca    1740
```

```
gggctgggga actatcagct atgccgccgt gtcgggcccc agtgatgaca agccctattg    1800
ctggcactac cccccacgcc cgtgcggaat agtgccagcg cgaggtgtct gcggtccggt    1860
ctattgtttt acacctagcc cggtggtcgt cggcaccaca gaccgcaagg ggaatcccac    1920
ttacagttgg ggcgaaaatg agactgacat ctttctcttg aacaacacga ggcccctac     1980 tggcaactgg tttggctgca cctggatgaa ttccacaggg tttgtcaaga cttgcggggc    2040
tccaccctgc aacttagggc ctacaggcaa caatagcctt aagtgtccta ctgattgctt    2100
ccgcaagcac ccagacgcca cctacaccaa gtgtgggtca ggaccctggc tcactcccg     2160 gtgtctggtg cattacccett accggttgtg gcattacccg tgcaccctaa attacaccat    2220
cttcaaggtg cgcatgtaca ttgggggcct cgagcacagg ctcgaggtgg catgcaactg    2280
gacccgtggt gagcggtgtg atcttgaaga cagggatagg gccgagctga gcccgctcct    2340
acataccacc acgcagtggg ccatattgcc gtgctctttc acaccacac ccgctcttag     2400 cactggtctc atacacttac atcaaaatat agtagacacc cagtatcttt acggtctgag    2460
ctccagcatc gtctcgtggg ccgttaagtg ggagtacata gtgctggcct tcttattact    2520
tgctgatgcc cgtatttgta cttgcctatg gatcatgctc ctggtttgtc aggccgaagc    2580
ggccctggag aacgtcattg tcctaaacgc ggctgcggct gcgggactc atgggttttt     2640 ctggggcctg ctcgtcatct gcttcgcctg gcacttcaag ggcaggttgg tccctggggc    2700
cacctacctt tgcttgggca tttggccatt actcttactc cttttcctcc tgccccaaag    2760
ggctctagcc ctggactcaa gcgatggcgg gactgtgggt tgtcttgtgt taaccatcct    2820
tacaatcttc acactcaccc ccgggtacaa gaagatggta gtgttggtca tatggtggct    2880
tcagtatttc atagcccggg tagaggcctt tatccatgtg tgggtgcccc cgttgcaggt    2940
taggggtggt cgtgatgcta ttatcatgct cacatgcctt ttccatcctg ccctgggtt     3000 tgaggtcacg aaaatcctcc tcgggatact aggtcctttg tacctgctgc agtactcgct    3060
catcaagctg ccttatttca tcagggcgcg cgccctgctg agggcgtgcc tgctagcgaa    3120
gcacttggcc tgtggcaggt acgtgcaggc ggccttgctc caccttggta ggctgaccgg    3180
aacgtacatt tatgaccacc ttgcccccat gaaggattgg gcagcgtccg ggctgcgcga    3240
cttagcagtg gccacggagc ccatcatatt ctcccctatg gagacgaagg tcatcacgtg    3300
gggggctgac acggccgcat gtgggacat acttgccggc cttcctgtat cagctaggcg     3360
aggccatgaa atcttcctgg ggccagccga tgacatcaga gaggcgggct ggcgacttct    3420
cgctcccatc actgcttatg cccagcaaac acgaggcctc ctgggcgcca tagtggtgag    3480
tatgacgggg cgtgacagga cagaacaggc cggggaagtc caaatcctgt ccacagtctc    3540
tcagtccttc ctcggaacaa ccatctcggg ggttttgtgg actgtttacc acggagctgg    3600
caacaagact ctagccggct tacggggtcc ggtcacgcag atgtactcga gtgctgaggg    3660
ggacttggta ggctggccca gcccccctgg gaccaagtct ttggagccgt gcaagtgtgg    3720
agccgtcgac ctatatctgg tcacgcgcaa cgctgatgtc atcccggctc ggagacgcgg    3780
ggacaagcgg ggagcattgc tctccccgag acccatttcg accttgaagg ggtcctcggg    3840
ggggccggtg ctctgcccta ggggccacgt cgttgggctc ttccgagcag ctgtgtgctc    3900
tcggggcgtg gccaaatcca tcgatttcat ccccgttgag acactcgacg ttgttacaag    3960
gtctcccact ttcagtgaca acagcacgcc accggctgtg cccagacct atcaggtcgg     4020 gtacttgcat gctccaactg gcagtggaaa gagcaccaag gtccctgtcg cgtatgccgc    4080
ccaggggtac aaagtactag tgcttaaccc ctcggtagct gccaccctgg ggtttgggc     4140
```

```
gtacctatcc aaggcacatg gcatcaatcc caacattagg actggagtca ggaccgtgat    4200
gaccggggag gccatcacgt actccacata tggcaaattt ctcgccgatg ggggctgcgc    4260
tagcggcgcc tatgcatcca tcatatgcga tgaatgccac gctgtggatg ctacctccat    4320
tctcggcatc ggaacggtcc ttgatcaagc agagacagcc ggggtcagac taactgtgct    4380
ggctacggcc acaccccccg ggtcagtgac aacccccccat cccgatatag aagaggtagg    4440
cctcgggcgg gagggtgaga tccccttcta tgggagggcg attccccctat cctgcatcaa    4500 gggagggaga cacctgattt tctgccactc aaagaaaaag tgtgacgagc tcgcggcggc    4560
ccttcggggc atgggcttga atgccgtggc atactataga gggttggacg tctccataat    4620
accagctcag ggagatgtgg tggtcgtcgc caccgacgcc ctcatgacgg ggtacactgg    4680
agactttgac tccgtgatcg actgcaatgt agcggtcacc caagctgtcg acttcagcct    4740
ggaccccacc ttcactataa ccacacagac tgtcccacaa gacgctgtct cacgcagtca    4800
gcgccgcggg cgcacaggta gaggaagaca gggcacttat aggtatgttt ccactggtga    4860
acgagcctca ggaatgtttg acagtgtagt gctttgtgag tgctacgacg caggggctgc    4920
gtggtacgat ctcacaccag cggagaccac cgtcaggctt agagcgtatt tcaacacgcc    4980
cggcctaccc gtgtgtcaag accatcttga attttgggag gcagttttca ccggcctcac    5040
acacatagac gcccacttcc tctcccaaac aaagcaagcg gggagaaact tcgcgtacct    5100
agtagcctac caagctacgg tgtgcgccag agccaaggcc cctcccccgt cctgggacgc    5160
catgtggaag tgcctggccc gactcaagcc tacgcttgcg ggcccacac ctctcctgta    5220 ccgtttgggc cctattacca atgaggtcac cctcacacac cctgggacga agtacatcgc    5280
cacatgcatg caagctgacc ttgaggtcat gaccagcacg tgggtcctag ctggaggagt    5340
cctggcagcc gtcgccgcat attgcctggc gactggatgc gtttccatca tcggccgctt    5400
gcacgtcaac cagcgagtcg tcgttgcgcc ggataaggag gtcctgtatg aggcttttga    5460
tgagatggag gaatgcgcct ctagggcggc tctcatcgaa gaggggcagc ggatagccga    5520
gatgttgaag tccaagatcc aaggcttgct gcagcaggcc tctaagcagg cccaggacat    5580
acaacccgct atgcaggctt catggcccaa agtggaacaa ttttgggcca gacacatgtg    5640
gaacttcatt agcggcatcc aatacctcgc aggattgtca acactgccag ggaaccccgc    5700
ggtggcttcc atgatggcat tcagtgccgc cctcaccagt ccgttgtcga ccagtaccac    5760
catccttctc aacatcatgg gaggctggtt agcgtcccag atcgcaccac ccgcgggggc    5820
caccggcttt gtcgtcagtg gcctggtggg ggctgccgtg ggcagcatag gcctgggtaa    5880
ggtgctggtg gacatcctgg caggatatgg tgcgggcatt tcggggggccc tcgtcgcatt    5940 caagatcatg tctggcgaga agccctctat ggaagatgtc atcaatctac tgcctgggat    6000
cctgtctccg ggagccctgg tggtgggggt catctgcgcg gccattctgc gccgccacgt    6060
gggaccgggg gagggcgcgg tccaatggat gaacaggctt attgcctttg cttccagagg    6120
aaaccacgtc gcccctactc actacgtgac ggagtcggat gcgtcgcagc gtgtgacccc    6180
actacttggc tctcttacta taaccagcct actcagaaga ctccacaatt ggataactga    6240
ggactgcccc atcccatgct ccggatcctg gctccgcgac gtgtgggact gggtttgcac    6300
catcttgaca gacttcaaaa attggctgac ctctaaattg ttccccaagc tgcccggcct    6360
ccccttcatc tcttgtcaaa agggggtacaa gggtgtgtgg gccggcactg gcatcatgac    6420
cacgcgctgc ccttgcggcg ccaacatctc tggcaatgtc cgcctgggct ctatgaggat    6480
cacagggcct aaaacctgca tgaacacctg gcaggggacc tttcctatca attgctacac    6540
```

```
ggagggccag tgcgcgccga aaccccccac gaactacaag accgccatct ggagggtggc    6600
ggcctcggag tacgcggagg tgacgcagca tgggtcgtac tcctatgtaa caggactgac    6660
cactgacaat ctgaaaattc cttgccaact accttctcca gagttttttct cctgggtgga   6720 cggtgtgcag atccataggt ttgcacccac accaaagccg ttttccggg atgaggtctc     6780 gttctgcgtt gggcttaatt cctatgctgt cgggtcccag cttccctgtg aacctgagcc    6840
cgacgcagac gtattgaggt ccatgctaac agatccgccc cacatcacgg cggagactgc    6900
ggcgcggcgc ttggcacggg gatcacctcc atctgaggcg agctcctcag tgagccagct    6960
atcagcaccg tcgctgcggg ccacctgcac cacccacagc aacacctatg acgtggacat    7020
ggtcgatgcc aacctgctca tggagggcgg tgtggctcag acagagcctg agtccagggt    7080
gcccgttctg gactttctcg agccaatggc cgaggaagag agcgaccttg agccctcaat    7140
accatcggag tgcatgctcc ccaggagcgg gtttccacgg gccttaccgg cttgggcacg    7200
gcctgactac aacccgccgc tcgtggaatc gtggaggagg ccagattacc aaccgcccac    7260
cgttgctggt tgtgctctcc ccccccaa gaaggccccg acgcctcccc caaggagacg      7320
ccggacagtg ggtctgagcg agagcaccat atcagaagcc ctccagcaac tggccatcaa    7380
gacctttggc cagcccccct cgagcggtga tgcaggctcg tccacggggg cgggcgccgc    7440
cgaatccggc ggtccgacgt cccctggtga gccggccccc tcagagacag gttccgcctc    7500
ctctatgccc cccctcgagg gggagcctgg agatccggac ctggagtctg atcaggtaga    7560
gcttcaacct cccccccagg ggggggggt agctcccggt tcgggctcgg ggtcttggtc     7620
tacttgctcc gaggaggacg ataccaccgt gtgctgctcc atgtcatact cctggaccgg    7680
ggctctaata actccctgta gccccgaaga ggaaaagttg ccaatcaacc ctttgagtaa    7740
ctcgctgttg cgataccata acaaggtgta ctgtacaaca tcaaagagcg cctcacagag    7800
ggctaaaaag gtaacttttg acaggacgca agtgctcgac gcccattatg actcagtctt    7860
aaaggacatc aagctagcgg cttccaaggt cagcgcaagg ctcctcacct tggaggaggc    7920
gtgccagttg actccacccc attctgcaag atccaagtat ggattcgggg ccaaggaggt    7980
ccgcagcttg tccgggaggg ccgttaacca catcaagtcc gtgtggaagg acctcctgga    8040
agacccacaa acaccaattc ccacaaccat catggccaaa aatgaggtgt tctgcgtgga    8100
ccccgccaag gggggtaaga aaccagctcg cctcatcgtt taccctgacc tcggcgtccg    8160
ggtctgcgag aaaatggccc tctatgacat tacacaaaag cttcctcagg cggtaatggg    8220
agcttcctat ggcttccagt actcccctgc ccaacgggtg gagtatctct tgaaagcatg    8280
ggcggaaaag aaggaccca tgggtttttc gtatgatacc cgatgcttcg actcaaccgt     8340
cactgagaga gacatcagga ccgaggagtc catataccag gcctgctccc tgcccgagga    8400
ggcccgcact gccatacact cgctgactga gagactttac gtaggagggc ccatgttcaa    8460
cagcaagggt caaacctgcg gttacagacg ttgccgcgcc agcggggtgc taaccactag    8520
catgggtaac accatcacat gctatgtgaa agccctagcg gcctgcaagg ctgcggggat    8580
agttgcgccc acaatgctgg tatgcggcga tgacctagta gtcatctcag aaagccaggg    8640
gactgaggag gacgagcgga acctgagagc cttcacggag gccatgacca ggtactctgc    8700
ccctcctggt gatcccccca gaccggaata tgacctggag ctaataacat cctgttcctc    8760
aaatgtgtct gtggcgttgg gcccgcgggg ccgccgcaga tactacctga ccagagaccc    8820
aaccactcca ctcgcccggg ctgcctggga aacagttaga cactcccta tcaattcatg     8880 gctgggaaac atcatccagt atgctccaac catatgggtt cgcatggtcc taatgacaca    8940
```

```
cttcttctcc attctcatgg tccaagacac cctggaccag aacctcaact ttgagatgta    9000
tggatcagta tactccgtga atcctttgga ccttccagcc ataattgaga ggttacacgg    9060
gcttgacgcc ttttctatgc acacatactc tcaccacgaa ctgacgcggg tggcttcagc    9120
cctcagaaaa cttggggcgc caccctcag ggtgtggaag agtcgggctc gcgcagtcag    9180
ggcgtccctc atctcccgtg gagggaaagc ggccgtttgc ggccgatatc tcttcaattg    9240
ggcggtgaag accaagctca aactcactcc attgccggag gcgcgcctac tggacttatc    9300
cagttggttc accgtcggcg ccggcggggg cgacattttt cacagcgtgt cgcgcgcccg    9360
accccgctca ttactcttcg gcctactcct acttttcgta ggggtaggcc tcttcctact    9420
ccccgctcgg tagagcggca cactaggt acactccata gctaactgtt ccttttttt    9480 tttttttttt tttttttttt tttttttttt ttttttcttttt tttttttttt ccctctttct    9540
tcccttctca tcttattcta ctttctttct tggtggctcc atcttagccc tagtcacggc    9600
tagctgtgaa aggtccgtga gccgcatgac tgcagagagt gccgtaactg gtctctctgc    9660
agatcatgt                                                             9669
```

<210> SEQ ID NO 2
<211> LENGTH: 3030
<212> TYPE: PRT
<213> ORGANISM: Hepatitis C virus

<400> SEQUENCE: 2

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Thr Ser Ala Val
            180                 185                 190

Pro Tyr Arg Asn Ala Ser Gly Val Tyr His Val Thr Asn Asp Cys Pro
        195                 200                 205

Asn Ser Ser Ile Val Tyr Glu Ala Glu Asp Leu Ile Leu His Ala Pro
    210                 215                 220

Gly Cys Val Pro Cys Val Arg Gln Gly Asn Val Ser Arg Cys Trp Val
225                 230                 235                 240
```

-continued

```
Gln Ile Thr Pro Thr Leu Ser Ala Pro Ser Leu Gly Ala Val Thr Ala
            245                 250                 255

Pro Leu Arg Arg Ala Val Asp Tyr Leu Ala Gly Ala Ala Leu Cys
        260                 265                 270

Ser Ala Leu Tyr Val Gly Asp Ala Cys Gly Ala Val Phe Leu Val Gly
            275                 280                 285

Gln Met Phe Thr Tyr Ser Pro Arg Arg His Asn Val Val Gln Asp Cys
        290                 295                 300

Asn Cys Ser Ile Tyr Ser Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Val Val Ile Asp Ile Ile Ala Gly Ala His
            340                 345                 350

Trp Gly Val Leu Phe Ala Ala Ala Tyr Tyr Ser Ala Ala Asn Trp
        355                 360                 365

Ala Lys Val Val Leu Val Leu Phe Leu Phe Ala Gly Val Asp Ala Ser
        370                 375                 380

Thr Arg Thr Val Gly Gly Ser Ala Ala Gln Gly Ala Arg Gly Leu Ala
385                 390                 395                 400

Ser Leu Phe Thr Pro Gly Pro Gln Gln Asn Leu Gln Leu Ile Asn Thr
            405                 410                 415

Asn Gly Ser Trp His Ile Asn Arg Thr Ala Leu Asn Cys Asn Asp Ser
        420                 425                 430

Leu Gln Thr Gly Phe Val Ala Gly Leu Leu Tyr Tyr His Lys Phe Asn
        435                 440                 445

Ser Thr Gly Cys Pro Gln Arg Met Ala Ser Cys Arg Pro Leu Ala Ala
450                 455                 460

Phe Asp Gln Gly Trp Gly Thr Ile Ser Tyr Ala Ala Val Ser Gly Pro
465                 470                 475                 480

Ser Asp Asp Lys Pro Tyr Cys Trp His Tyr Pro Pro Arg Pro Cys Gly
            485                 490                 495

Ile Val Pro Ala Arg Gly Val Cys Gly Pro Val Tyr Cys Phe Thr Pro
            500                 505                 510

Ser Pro Val Val Gly Thr Thr Asp Arg Lys Gly Asn Pro Thr Tyr
            515                 520                 525

Ser Trp Gly Glu Asn Glu Thr Asp Ile Phe Leu Leu Asn Asn Thr Arg
        530                 535                 540

Pro Pro Thr Gly Asn Trp Phe Gly Cys Thr Trp Met Asn Ser Thr Gly
545                 550                 555                 560

Phe Val Lys Thr Cys Gly Ala Pro Pro Cys Asn Leu Gly Pro Thr Gly
            565                 570                 575

Asn Asn Ser Leu Lys Cys Pro Thr Asp Cys Phe Arg Lys His Pro Asp
        580                 585                 590

Ala Thr Tyr Thr Lys Cys Gly Ser Gly Pro Trp Leu Thr Pro Arg Cys
        595                 600                 605

Leu Val His Tyr Pro Tyr Arg Leu Trp His Tyr Pro Cys Thr Leu Asn
        610                 615                 620

Tyr Thr Ile Phe Lys Val Arg Met Tyr Ile Gly Gly Leu Glu His Arg
625                 630                 635                 640

Leu Glu Val Ala Cys Asn Trp Thr Arg Gly Glu Arg Cys Asp Leu Glu
                645                 650                 655

Asp Arg Asp Arg Ala Glu Leu Ser Pro Leu Leu His Thr Thr Thr Gln
            660                 665                 670
```

-continued

```
Trp Ala Ile Leu Pro Cys Ser Phe Thr Pro Thr Pro Ala Leu Ser Thr
            675                 680                 685

Gly Leu Ile His Leu His Gln Asn Ile Val Asp Thr Gln Tyr Leu Tyr
        690                 695                 700

Gly Leu Ser Ser Ser Ile Val Ser Trp Ala Val Lys Trp Glu Tyr Ile
705                 710                 715                 720

Val Leu Ala Phe Leu Leu Leu Ala Asp Ala Arg Ile Cys Thr Cys Leu
                725                 730                 735

Trp Ile Met Leu Leu Val Cys Gln Ala Glu Ala Ala Leu Glu Asn Val
            740                 745                 750

Ile Val Leu Asn Ala Ala Ala Ala Gly Thr His Gly Phe Phe Trp
        755                 760                 765

Gly Leu Leu Val Ile Cys Phe Ala Trp His Phe Lys Gly Arg Leu Val
770                 775                 780

Pro Gly Ala Thr Tyr Leu Cys Leu Gly Ile Trp Pro Leu Leu Leu
785                 790                 795                 800

Leu Phe Leu Leu Pro Gln Arg Ala Leu Ala Leu Asp Ser Ser Asp Gly
                805                 810                 815

Gly Thr Val Gly Cys Leu Val Leu Thr Ile Leu Thr Ile Phe Thr Leu
            820                 825                 830

Thr Pro Gly Tyr Lys Lys Met Val Val Leu Val Ile Trp Trp Leu Gln
        835                 840                 845

Tyr Phe Ile Ala Arg Val Glu Ala Phe Ile His Val Trp Val Pro Pro
850                 855                 860

Leu Gln Val Arg Gly Gly Arg Asp Ala Ile Ile Met Leu Thr Cys Leu
865                 870                 875                 880

Phe His Pro Ala Leu Gly Phe Glu Val Thr Lys Ile Leu Leu Gly Ile
                885                 890                 895

Leu Gly Pro Leu Tyr Leu Leu Gln Tyr Ser Leu Ile Lys Leu Pro Tyr
            900                 905                 910

Phe Ile Arg Ala Arg Ala Leu Leu Arg Ala Cys Leu Leu Ala Lys His
        915                 920                 925

Leu Ala Cys Gly Arg Tyr Val Gln Ala Ala Leu Leu His Leu Gly Arg
930                 935                 940

Leu Thr Gly Thr Tyr Ile Tyr Asp His Leu Ala Pro Met Lys Asp Trp
945                 950                 955                 960

Ala Ala Ser Gly Leu Arg Asp Leu Ala Val Ala Thr Glu Pro Ile Ile
                965                 970                 975

Phe Ser Pro Met Glu Thr Lys Val Ile Thr Trp Gly Ala Asp Thr Ala
            980                 985                 990

Ala Cys Gly Asp Ile Leu Ala Gly Leu Pro Val Ser Ala Arg Arg Gly
        995                 1000                1005

His Glu Ile Phe Leu Gly Pro Ala Asp Asp Ile Arg Glu Ala Gly
    1010                1015                1020

Trp Arg Leu Leu Ala Pro Ile Thr Ala Tyr Ala Gln Gln Thr Arg
    1025                1030                1035

Gly Leu Leu Gly Ala Ile Val Val Ser Met Thr Gly Arg Asp Arg
    1040                1045                1050

Thr Glu Gln Ala Gly Glu Val Gln Ile Leu Ser Thr Val Ser Gln
    1055                1060                1065

Ser Phe Leu Gly Thr Thr Ile Ser Gly Val Leu Trp Thr Val Tyr
    1070                1075                1080

His Gly Ala Gly Asn Lys Thr Leu Ala Gly Leu Arg Gly Pro Val
```

-continued

```
              1085                1090                1095
Thr Gln Met Tyr Ser Ser Ala Glu Gly Asp Leu Val Gly Trp Pro
              1100                1105                1110
Ser Pro Pro Gly Thr Lys Ser Leu Glu Pro Cys Lys Cys Gly Ala
              1115                1120                1125
Val Asp Leu Tyr Leu Val Thr Arg Asn Ala Asp Val Ile Pro Ala
              1130                1135                1140
Arg Arg Arg Gly Asp Lys Arg Gly Ala Leu Leu Ser Pro Arg Pro
              1145                1150                1155
Ile Ser Thr Leu Lys Gly Ser Ser Gly Gly Pro Val Leu Cys Pro
              1160                1165                1170
Arg Gly His Val Val Gly Leu Phe Arg Ala Ala Val Cys Ser Arg
              1175                1180                1185
Gly Val Ala Lys Ser Ile Asp Phe Ile Pro Val Glu Thr Leu Asp
              1190                1195                1200
Val Val Thr Arg Ser Pro Thr Phe Ser Asp Asn Ser Thr Pro Pro
              1205                1210                1215
Ala Val Pro Gln Thr Tyr Gln Val Gly Tyr Leu His Ala Pro Thr
              1220                1225                1230
Gly Ser Gly Lys Ser Thr Lys Val Pro Val Ala Tyr Ala Ala Gln
              1235                1240                1245
Gly Tyr Lys Val Leu Val Leu Asn Pro Ser Val Ala Ala Thr Leu
              1250                1255                1260
Gly Phe Gly Ala Tyr Leu Ser Lys Ala His Gly Ile Asn Pro Asn
              1265                1270                1275
Ile Arg Thr Gly Val Arg Thr Val Met Thr Gly Glu Ala Ile Thr
              1280                1285                1290
Tyr Ser Thr Tyr Gly Lys Phe Leu Ala Asp Gly Gly Cys Ala Ser
              1295                1300                1305
Gly Ala Tyr Asp Ile Ile Ile Cys Asp Glu Cys His Ala Val Asp
              1310                1315                1320
Ala Thr Ser Ile Leu Gly Ile Gly Thr Val Leu Asp Gln Ala Glu
              1325                1330                1335
Thr Ala Gly Val Arg Leu Thr Val Leu Ala Thr Ala Thr Pro Pro
              1340                1345                1350
Gly Ser Val Thr Thr Pro His Pro Asp Ile Glu Glu Val Gly Leu
              1355                1360                1365
Gly Arg Glu Gly Glu Ile Pro Phe Tyr Gly Arg Ala Ile Pro Leu
              1370                1375                1380
Ser Cys Ile Lys Gly Gly Arg His Leu Ile Phe Cys His Ser Lys
              1385                1390                1395
Lys Lys Cys Asp Glu Leu Ala Ala Ala Leu Arg Gly Met Gly Leu
              1400                1405                1410
Asn Ala Val Ala Tyr Tyr Arg Gly Leu Asp Val Ser Ile Ile Pro
              1415                1420                1425
Ala Gln Gly Asp Val Val Val Ala Thr Asp Ala Leu Met Thr
              1430                1435                1440
Gly Tyr Thr Gly Asp Phe Asp Ser Val Ile Asp Cys Asn Val Ala
              1445                1450                1455
Val Thr Gln Ala Val Asp Phe Ser Leu Asp Pro Thr Phe Thr Ile
              1460                1465                1470
Thr Thr Gln Thr Val Pro Gln Asp Ala Val Ser Arg Ser Gln Arg
              1475                1480                1485
```

-continued

Arg Gly Arg Thr Gly Arg Gly Arg Gln Gly Thr Tyr Arg Tyr Val
1490            1495                1500

Ser Thr Gly Glu Arg Ala Ser Gly Met Phe Asp Ser Val Val Leu
1505            1510                1515

Cys Glu Cys Tyr Asp Ala Gly Ala Ala Trp Tyr Asp Leu Thr Pro
1520            1525                1530

Ala Glu Thr Thr Val Arg Leu Arg Ala Tyr Phe Asn Thr Pro Gly
1535            1540                1545

Leu Pro Val Cys Gln Asp His Leu Glu Phe Trp Glu Ala Val Phe
1550            1555                1560

Thr Gly Leu Thr His Ile Asp Ala His Phe Leu Ser Gln Thr Lys
1565            1570                1575

Gln Ala Gly Glu Asn Phe Ala Tyr Leu Val Ala Tyr Gln Ala Thr
1580            1585                1590

Val Cys Ala Arg Ala Lys Ala Pro Pro Pro Ser Trp Asp Ala Met
1595            1600                1605

Trp Lys Cys Leu Ala Arg Leu Lys Pro Thr Leu Ala Gly Pro Thr
1610            1615                1620

Pro Leu Leu Tyr Arg Leu Gly Pro Ile Thr Asn Glu Val Thr Leu
1625            1630                1635

Thr His Pro Gly Thr Lys Tyr Ile Ala Thr Cys Met Gln Ala Asp
1640            1645                1650

Leu Glu Val Met Thr Ser Thr Trp Val Leu Ala Gly Gly Val Leu
1655            1660                1665

Ala Ala Val Ala Ala Tyr Cys Leu Ala Thr Gly Cys Val Ser Ile
1670            1675                1680

Ile Gly Arg Leu His Val Asn Gln Arg Val Val Ala Pro Asp
1685            1690                1695

Lys Glu Val Leu Tyr Glu Ala Phe Asp Glu Met Glu Glu Cys Ala
1700            1705                1710

Ser Arg Ala Ala Leu Ile Glu Glu Gly Gln Arg Ile Ala Glu Met
1715            1720                1725

Leu Lys Ser Lys Ile Gln Gly Leu Leu Gln Gln Ala Ser Lys Gln
1730            1735                1740

Ala Gln Asp Ile Gln Pro Ala Met Gln Ala Ser Trp Pro Lys Val
1745            1750                1755

Glu Gln Phe Trp Ala Arg His Met Trp Asn Phe Ile Ser Gly Ile
1760            1765                1770

Gln Tyr Leu Ala Gly Leu Ser Thr Leu Pro Gly Asn Pro Ala Val
1775            1780                1785

Ala Ser Met Met Ala Phe Ser Ala Ala Leu Thr Ser Pro Leu Ser
1790            1795                1800

Thr Ser Thr Thr Ile Leu Leu Asn Ile Met Gly Gly Trp Leu Ala
1805            1810                1815

Ser Gln Ile Ala Pro Pro Ala Gly Ala Thr Gly Phe Val Val Ser
1820            1825                1830

Gly Leu Val Gly Ala Ala Val Gly Ser Ile Gly Leu Gly Lys Val
1835            1840                1845

Leu Val Asp Ile Leu Ala Gly Tyr Gly Ala Gly Ile Ser Gly Ala
1850            1855                1860

Leu Val Ala Phe Lys Ile Met Ser Gly Glu Lys Pro Ser Met Glu
1865            1870                1875

Asp Val Ile Asn Leu Leu Pro Gly Ile Leu Ser Pro Gly Ala Leu
1880            1885                1890

-continued

Val Val Gly Val Ile Cys Ala Ala Ile Leu Arg Arg His Val Gly
1895                1900                1905

Pro Gly Glu Gly Ala Val Gln Trp Met Asn Arg Leu Ile Ala Phe
1910                1915                1920

Ala Ser Arg Gly Asn His Val Ala Pro Thr His Tyr Val Thr Glu
1925                1930                1935

Ser Asp Ala Ser Gln Arg Val Thr Gln Leu Leu Gly Ser Leu Thr
1940                1945                1950

Ile Thr Ser Leu Leu Arg Arg Leu His Asn Trp Ile Thr Glu Asp
1955                1960                1965

Cys Pro Ile Pro Cys Ser Gly Ser Trp Leu Arg Asp Val Trp Asp
1970                1975                1980

Trp Val Cys Thr Ile Leu Thr Asp Phe Lys Asn Trp Leu Thr Ser
1985                1990                1995

Lys Leu Phe Pro Lys Leu Pro Gly Leu Pro Phe Ile Ser Cys Gln
2000                2005                2010

Lys Gly Tyr Lys Gly Val Trp Ala Gly Thr Gly Ile Met Thr Thr
2015                2020                2025

Arg Cys Pro Cys Gly Ala Asn Ile Ser Gly Asn Val Arg Leu Gly
2030                2035                2040

Ser Met Arg Ile Thr Gly Pro Lys Thr Cys Met Asn Thr Trp Gln
2045                2050                2055

Gly Thr Phe Pro Ile Asn Cys Tyr Thr Glu Gly Gln Cys Ala Pro
2060                2065                2070

Lys Pro Pro Thr Asn Tyr Lys Thr Ala Ile Trp Arg Val Ala Ala
2075                2080                2085

Ser Glu Tyr Ala Glu Val Thr Gln His Gly Ser Tyr Ser Tyr Val
2090                2095                2100

Thr Gly Leu Thr Thr Asp Asn Leu Lys Ile Pro Cys Gln Leu Pro
2105                2110                2115

Ser Pro Glu Phe Phe Ser Trp Val Asp Gly Val Gln Ile His Arg
2120                2125                2130

Phe Ala Pro Thr Pro Lys Pro Phe Phe Arg Asp Glu Val Ser Phe
2135                2140                2145

Cys Val Gly Leu Asn Ser Tyr Ala Val Gly Ser Gln Leu Pro Cys
2150                2155                2160

Glu Pro Glu Pro Asp Ala Asp Val Leu Arg Ser Met Leu Thr Asp
2165                2170                2175

Pro Pro His Ile Thr Ala Glu Thr Ala Ala Arg Arg Leu Ala Arg
2180                2185                2190

Gly Ser Pro Pro Ser Glu Ala Ser Ser Ser Val Ser Gln Leu Ser
2195                2200                2205

Ala Pro Ser Leu Arg Ala Thr Cys Thr Thr His Ser Asn Thr Tyr
2210                2215                2220

Asp Val Asp Met Val Asp Ala Asn Leu Leu Met Glu Gly Gly Val
2225                2230                2235

Ala Gln Thr Glu Pro Glu Ser Arg Val Pro Val Leu Asp Phe Leu
2240                2245                2250

Glu Pro Met Ala Glu Glu Glu Ser Asp Leu Glu Pro Ser Ile Pro
2255                2260                2265

Ser Glu Cys Met Leu Pro Arg Ser Gly Phe Pro Arg Ala Leu Pro
2270                2275                2280

Ala Trp Ala Arg Pro Asp Tyr Asn Pro Pro Leu Val Glu Ser Trp

```
                2285                2290                2295

Arg Arg Pro Asp Tyr Gln Pro Pro Thr Val Ala Gly Cys Ala Leu
    2300                2305                2310

Pro Pro Pro Lys Lys Ala Pro Thr Pro Pro Arg Arg Arg Arg
    2315                2320                2325

Thr Val Gly Leu Ser Glu Ser Thr Ile Ser Glu Ala Leu Gln Gln
    2330                2335                2340

Leu Ala Ile Lys Thr Phe Gly Gln Pro Pro Ser Ser Gly Asp Ala
    2345                2350                2355

Gly Ser Ser Thr Gly Ala Gly Ala Ala Glu Ser Gly Gly Pro Thr
    2360                2365                2370

Ser Pro Gly Glu Pro Ala Pro Ser Glu Thr Gly Ser Ala Ser Ser
    2375                2380                2385

Met Pro Pro Leu Glu Gly Glu Pro Gly Asp Pro Asp Leu Glu Ser
    2390                2395                2400

Asp Gln Val Glu Leu Gln Pro Pro Gln Gly Gly Gly Val Ala
    2405                2410                2415

Pro Gly Ser Gly Ser Gly Ser Trp Ser Thr Cys Ser Glu Glu Asp
    2420                2425                2430

Asp Thr Thr Val Cys Cys Ser Met Ser Tyr Ser Trp Thr Gly Ala
    2435                2440                2445

Leu Ile Thr Pro Cys Ser Pro Glu Glu Glu Lys Leu Pro Ile Asn
    2450                2455                2460

Pro Leu Ser Asn Ser Leu Leu Arg Tyr His Asn Lys Val Tyr Cys
    2465                2470                2475

Thr Thr Ser Lys Ser Ala Ser Gln Arg Ala Lys Lys Val Thr Phe
    2480                2485                2490

Asp Arg Thr Gln Val Leu Asp Ala His Tyr Asp Ser Val Leu Lys
    2495                2500                2505

Asp Ile Lys Leu Ala Ala Ser Lys Val Ser Ala Arg Leu Leu Thr
    2510                2515                2520

Leu Glu Glu Ala Cys Gln Leu Thr Pro Pro His Ser Ala Arg Ser
    2525                2530                2535

Lys Tyr Gly Phe Gly Ala Lys Glu Val Arg Ser Leu Ser Gly Arg
    2540                2545                2550

Ala Val Asn His Ile Lys Ser Val Trp Lys Asp Leu Leu Glu Asp
    2555                2560                2565

Pro Gln Thr Pro Ile Pro Thr Thr Ile Met Ala Lys Asn Glu Val
    2570                2575                2580

Phe Cys Val Asp Pro Ala Lys Gly Gly Lys Lys Pro Ala Arg Leu
    2585                2590                2595

Ile Val Tyr Pro Asp Leu Gly Val Arg Val Cys Glu Lys Met Ala
    2600                2605                2610

Leu Tyr Asp Ile Thr Gln Lys Leu Pro Gln Ala Val Met Gly Ala
    2615                2620                2625

Ser Tyr Gly Phe Gln Tyr Ser Pro Ala Gln Arg Val Glu Tyr Leu
    2630                2635                2640

Leu Lys Ala Trp Ala Glu Lys Lys Asp Pro Met Gly Phe Ser Tyr
    2645                2650                2655

Asp Thr Arg Cys Phe Asp Ser Thr Val Thr Glu Arg Asp Ile Arg
    2660                2665                2670

Thr Glu Glu Ser Ile Tyr Gln Ala Cys Ser Leu Pro Glu Glu Ala
    2675                2680                2685
```

```
Arg Thr Ala Ile His Ser Leu Thr Glu Arg Leu Tyr Val Gly Gly
    2690            2695                2700
Pro Met Phe Asn Ser Lys Gly Gln Thr Cys Gly Tyr Arg Arg Cys
2705            2710                2715
Arg Ala Ser Gly Val Leu Thr Thr Ser Met Gly Asn Thr Ile Thr
2720            2725                2730
Cys Tyr Val Lys Ala Leu Ala Ala Cys Lys Ala Ala Gly Ile Val
2735            2740                2745
Ala Pro Thr Met Leu Val Cys Gly Asp Asp Leu Val Val Ile Ser
2750            2755                2760
Glu Ser Gln Gly Thr Glu Glu Asp Glu Arg Asn Leu Arg Ala Phe
2765            2770                2775
Thr Glu Ala Met Thr Arg Tyr Ser Ala Pro Pro Gly Asp Pro Pro
2780            2785                2790
Arg Pro Glu Tyr Asp Leu Glu Leu Ile Thr Ser Cys Ser Ser Asn
2795            2800                2805
Val Ser Val Ala Leu Gly Pro Arg Gly Arg Arg Arg Tyr Tyr Leu
2810            2815                2820
Thr Arg Asp Pro Thr Thr Pro Leu Ala Arg Ala Ala Trp Glu Thr
2825            2830                2835
Val Arg His Ser Pro Ile Asn Ser Trp Leu Gly Asn Ile Ile Gln
2840            2845                2850
Tyr Ala Pro Thr Ile Trp Val Arg Met Val Leu Met Thr His Phe
2855            2860                2865
Phe Ser Ile Leu Met Val Gln Asp Thr Leu Asp Gln Asn Leu Asn
2870            2875                2880
Phe Glu Met Tyr Gly Ser Val Tyr Ser Val Asn Pro Leu Asp Leu
2885            2890                2895
Pro Ala Ile Ile Glu Arg Leu His Gly Leu Asp Ala Phe Ser Met
2900            2905                2910
His Thr Tyr Ser His His Glu Leu Thr Arg Val Ala Ser Ala Leu
2915            2920                2925
Arg Lys Leu Gly Ala Pro Pro Leu Arg Val Trp Lys Ser Arg Ala
2930            2935                2940
Arg Ala Val Arg Ala Ser Leu Ile Ser Arg Gly Gly Lys Ala Ala
2945            2950                2955
Val Cys Gly Arg Tyr Leu Phe Asn Trp Ala Val Lys Thr Lys Leu
2960            2965                2970
Lys Leu Thr Pro Leu Pro Glu Ala Arg Leu Leu Asp Leu Ser Ser
2975            2980                2985
Trp Phe Thr Val Gly Ala Gly Gly Gly Asp Ile Phe His Ser Val
2990            2995                3000
Ser Arg Ala Arg Pro Arg Ser Leu Leu Phe Gly Leu Leu Leu Leu
3005            3010                3015
Phe Val Gly Val Gly Leu Phe Leu Leu Pro Ala Arg
3020            3025                3030
```

<210> SEQ ID NO 3
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 3
gacagtcagg catgaaagaa gtg                                             23

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
gcagaagatg agatgcctac                                          20

<210> SEQ ID NO 5
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 5
gtggtgttgc agtctatgac agaatcaaag tcgccggtaa ac                 42

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 6
ctatggagtg tacctagtgt gtgc                                     24

<210> SEQ ID NO 7
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 7
atgcatcagg agttatggag tgtttagctc ccagc                         35

<210> SEQ ID NO 8
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 8
tcatgcggct cacggacctt tcacagctag                               30

<210> SEQ ID NO 9
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 9
gcggccgcta atacgactca ctatagaccc gccccttatt ggggcgacac tccaccatg    59

<210> SEQ ID NO 10
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 10
atgagcacga atcctaaacc tcaaagaaaa accaaaag                              38

<210> SEQ ID NO 11
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 11
cttgcggtct gtggtgccga cgac                                            24

<210> SEQ ID NO 12
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 12
gaatagtgcc agcccgaggt gtctgcg                                         27

<210> SEQ ID NO 13
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 13
gagaagtcgc cagcccgcct ctctgatg                                        28

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
cttacaatct tcacactcac                                                 20

<210> SEQ ID NO 15
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 15
tgtgctgttg tcagtgaaca c                                               21

<210> SEQ ID NO 16
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 16
gcggccgcgg tgtcgcgaag gcgctcgatt tcattcc                              37

<210> SEQ ID NO 17
<211> LENGTH: 35

```
<212> TYPE: DNA
<213> ORGANISM: Artificial Sequence
<220> FEATURE:
<223> OTHER INFORMATION: synthetic oligonucleotide

<400> SEQUENCE: 17
atgcatcagg agttatggag tgtttagctc ccagc                              35

<210> SEQ ID NO 18
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 18
gccgccatct gcggcatcta tctcttcaac tg                                 32

<210> SEQ ID NO 19
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 19
gcggccgcgt gaaaacaaag cgcaaactca ctccattagc tgacg                   45

<210> SEQ ID NO 20
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 20
ggacctttca cagctagccg tgactaggg                                     29

<210> SEQ ID NO 21
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 21
actgtcttca cgcagaaagc gcctagccat                                    30

<210> SEQ ID NO 22
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 22
gtagcgttgg gttgcgaaag gccttgtggt actgcctgat                         40

<210> SEQ ID NO 23
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 23
cagttagccg ccgacgcgta gtatg                                         25
```

<210> SEQ ID NO 24
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 24
gtccttgagg acggggtaaa ctatgcaaca g                                    31

<210> SEQ ID NO 25
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 25
cttgacaaac cctgtggaat tcatccaggt gcagccaaac cag                       43

<210> SEQ ID NO 26
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 26
catagtgctg gccttcttat tacttgctg                                       29

<210> SEQ ID NO 27
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 27
ctgagcccgc tcctacatac cac                                             23

<210> SEQ ID NO 28
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 28
cagagaggcg ggctggcgac ttctcgctcc catcac                               36

<210> SEQ ID NO 29
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 29
gcagtggcca cggagcccat catattctc                                       29

<210> SEQ ID NO 30
<211> LENGTH: 26
<212> TYPE: DNA
<213> ORGANISM: Artificial Sequence
<220> FEATURE:
<223> OTHER INFORMATION: synthetic oligonucleotide

```
<400> SEQUENCE: 30
cgcccgaggc ctacctcttc tatatc                                          26

<210> SEQ ID NO 31
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 31
cccatcacgt actccacata tggc                                            24

<210> SEQ ID NO 32
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 32
gcgcacaccg tagcttggta gg                                              22

<210> SEQ ID NO 33
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 33
gagcgagcct caggaatgtt tgaca                                           25

<210> SEQ ID NO 34
<211> LENGTH: 24
<212> TYPE: DNA
<213> ORGANISM: Hepatitis C virus

<400> SEQUENCE: 34
tgatgttgag aaggatggtg gtac                                            24

<210> SEQ ID NO 35
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 35
tggcccaaag tggaacaatt ttgg                                            24

<210> SEQ ID NO 36
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 36
caacgcagaa cgagacctca tccc                                            24

<210> SEQ ID NO 37
<211> LENGTH: 24
<212> TYPE: DNA
<213> ORGANISM: Artificial Sequence
```

```
<220> FEATURE:
<223> OTHER INFORMATION: synthetic oligonucleotide

<400> SEQUENCE: 37
gacctttcct atcaattgct acac                                              24

<210> SEQ ID NO 38
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 38
gaagctctac ctgatcagac tcca                                              24

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
tgggcacggc ctgactacaa                                                   20

<210> SEQ ID NO 40
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 40
ggccattttc tcgcagaccc ggac                                              24

<210> SEQ ID NO 41
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 41
atggccaaaa atgaggtgtt ctgc                                              24

<210> SEQ ID NO 42
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 42
aaggtccaaa ggattcacgg agta                                              24

<210> SEQ ID NO 43
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 43
ggtcaaacct gcggttacag acgttg                                            26
```

```
<210> SEQ ID NO 44
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 44
gtgtacctag tgtgtgccgc tcta                                              24

<210> SEQ ID NO 45
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 45
gtgtatgcgg cgaccgagtt gctcttg                                           27

<210> SEQ ID NO 46
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 46
aggtttagga ttcgtgctca tggtgcacgg tctacgagac ctc                         43

<210> SEQ ID NO 47
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 47
atgagcacga atcctaaacc tcaaagaaaa accaaaag                               38

<210> SEQ ID NO 48
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 48
atcagagagg cgggctggcg acttctcgct cccatcactg cttatgccca gca              53

<210> SEQ ID NO 49
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 49
ggattgatgc catgtgcctt ggataggtac                                        30

<210> SEQ ID NO 50
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 50
```

```
gtaaactatg caacagggaa tttacccggt tgctctttct ctatctttat ccttgcac        58
```

<210> SEQ ID NO 51
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 51

```
gattcccctt gcggtctgtg gtgccgacga                                        30
```

<210> SEQ ID NO 52
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 52

```
gggccagccg atgacatcag agagggggc tggcgacttc t                            41
```

<210> SEQ ID NO 53
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 53

```
gatgggagcg agaagtcgcc agccccctc tctgatgtca tc                           42
```

<210> SEQ ID NO 54
<211> LENGTH: 9669
<212> TYPE: DNA
<213> ORGANISM: Hepatitis C virus

<400> SEQUENCE: 54

```
acctgcccct aatagggcg acactccgcc atgaatcact ccctgtgag gaactactgt       60
cttcacgcag aaagcgccta gccatggcgt tagtatgagt gtcgtacagc ctccaggccc     120
cccctcccg ggagagccat agtggtctgc ggaaccggtg agtacaccgg aattgccggg     180
aagactgggt cctttcttgg ataaacccac tctatgcccg ccatttggg cgtgcccccg     240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaaagaa acaccaaccg ccgcccacag gacgtcaagt ccccgggcgg    420
tggtcagatc gttggtggag tttacttgtt gccgcgcagg ggccctaggt tgggtgtgcg    480
cgcaactcgg aagacttcag aacggtcgca acccgtgga cggcgtcagc ctatccccaa    540
ggcgcgccag cccacgggcc ggtcctgggg tcaacccggg tacccttggc ccctttatgc    600
caatgagggc ctcgggtggg cagggtggtt gctctccccc cgaggctctc ggcctaattg    660
gggcccaat gacccccggc ggaaatcgcg caacttgggt aaggtcatcg ataccctgac    720
gtgcggattc gccgacctca tgggtacat cccgctcgta ggcggccccg ttggggcgt    780
cgcaagggct ctcgcacacg tgtgagggt ccttgaggac ggggtaaact atgcaacagg    840
gaatttaccc ggttgctctt tctctatctt tatccttgca cttctttcat gcctgactgt    900
cccgacctct gccgttccct accgaaatgc ctctggggtt tatcatgtca ccaatgattg    960
cccaaactct tctatcgtct atgaggctga agacctgatc ttacacgcac ctggttgcgt   1020
```

```
gccctgtgtt aggcagggta atgtcagtag gtgctgggtc cagatcaccc ccacactgtc   1080
agccccgagc ctcggagcgg tcacggctcc tcttcggagg gccgttgact acttagcggg   1140
gggggctgcc ctttgctccg cgttatacgt cggagacgcg tgcggggcag tgttttggt    1200 aggtcaaatg ttcacctata gccctcgccg gcataatgtt gtgcaggact gcaactgttc   1260
catttacagt ggccacatca ccggccaccg gatggcatgg gacatgatga tgaattggtc   1320
acctacaaca gctttggtga tgcccagtt gttacggatt ccccaggtgg tcattgacat    1380
cattgccggg gcccactggg gggtcttgtt cgccgccgca tactacgcgt cggcggctaa   1440
ctgggccaag gttgtgctgg tcctgtttct gtttgcgggg gtcgatgcca gcacccgcac   1500
tgtgggtggt agtgcggccc aaggcgcgcg cgggctcgct tcactttca ccctgggcc     1560 gcagcagaac ttgcagctca taaataccaa cgggagctgg cacatcaaca gaactgccct   1620
taactgtaat gacagcctcc agactgggtt tgtagccggc ctcctgtatt atcacaagtt   1680
caactccact gggtgtccgc agcggatggc tagctgtagg cccctcgccg cattcgacca   1740
gggctgggga actatcagct atgccgccgt gtcgggcccc agtgatgaca gccctattg    1800 ctggcactac cccccacgcc cgtgcggaat agtgccagcg cgaggtgtct gcggtccggt   1860
ctattgtttt acacctagcc cggtggtcgt cggcaccaca gaccgcaagg ggaatcccac   1920
ttacagttgg ggcgaaaatg agactgacat ctttctcttg aacaacacga ggccccctac   1980
tggcaactgg tttggctgca cctggatgaa ttccacaggg tttgtcaaga cttgcggggc   2040
tccaccctgc aacttagggc ctacaggcaa caatagcctt aagtgtccta ctgattgctt   2100
ccgcaagcac ccagacgcca cctacaccaa gtgtgggtca ggaccctggc tcactcccg    2160 gtgtctggtg cattaccctt accggttgtg gcattacccg tgcacccta attacaccat     2220 cttcaaggtg cgcatgtaca ttgggggcct cgagcacagg ctcgaggtgg catgcaactg    2280
gacccgtggt gagcggtgtg atcttgaaga cagggatagg gccgagctga gcccgctcct   2340
acataccacc acgcagtggg ccatattgcc gtgctctttc acacccacac ccgctcttag    2400
cactggtctc atacacttac atcaaaatat agtagacacc cagtatcttt acggtctgag   2460
ctccagcatc gtctcgtggg ccgttaagtg ggagtacata gtgctggcct tcttattact   2520
tgctgatgcc cgtatttgta cttgcctatg gatcatgctc ctggtttgtc aggccgaagc   2580
ggccctggag aacgtcattg tcctaaacgc ggctgcggct gcggggactc atgggttttt    2640
ctggggcctg ctcgtcatct gcttcgcctg gcacttcaag ggcaggttgg tccctggggc   2700
cacctacctt tgcttgggca tttggccatt actcttactc cttttcctcc tgccccaaag   2760
ggctctagcc ctggactcaa gcgatggcgg gactgtgggt tgtcttgtgt taaccatcct   2820
tacaatcttc acactcaccc ccgggtacaa gaagatggta gtgttggtca tatggtggct    2880
tcagtatttc atagcccggg tagaggcctt tatccatgtg tgggtgcccc cgttgcaggt   2940 tagggggtggt cgtgatgcta ttatcatgct cacatgcctt ttccatcctg ccctgggtt    3000 tgaggtcacg aaaatcctcc tcgggatact aggtcctttg tacctgctgc agtactcgct   3060
catcaagctg ccttatttca tcaggcgcg cgccctgctg agggcgtgcc tgctagcgaa    3120
gcacttggcc tgtggcaggt acgtgcaggc ggccttgctc caccttggta ggctgaccgg   3180
aacgtacatt tatgaccacc ttgccccat gaaggattgg gcagcgtccg ggctgcgcga    3240
cttagcagtg gccacggagc ccatcatatt ctcccctatg gagacgaagg tcatcacgtg   3300
gggggctgac acggccgcat gtgggacat acttgccggc cttcctgtat cagctaggcg    3360
aggccatgaa atcttcctgg ggccagccga tgacatcaga gagggggct ggcgacttct     3420
```

```
cgctcccatc actgcttatg cccagcaaac acgaggcctc ctgggcgcca tagtggtgag    3480
tatgacgggg cgtgacagga cagaacaggc cggggaagtc caaatcctgt ccacagtctc    3540
tcagtccttc ctcggaacaa ccatctcggg ggttttgtgg actgtttacc acggagctgg    3600
caacaagact ctagccggct tacggggtcc ggtcacgcag atgtactcga gtgctgaggg    3660
ggacttggta ggctggccca gcccccctgg gaccaagtct ttggagccgt gcaagtgtgg    3720
agccgtcgac ctatatctgg tcacgcggaa cgctgatgtc atcccggctc ggagacgcgg    3780
ggacaagcgg ggagcattgc tctccccgag acccatttcg accttgaagg ggtcctcggg    3840
ggggccggtg ctctgcccta ggggccacgt cgttgggctc ttccgagcag ctgtgtgctc    3900
tcggggcgtg ccaaatcca tcgatttcat ccccgttgag acactcgacg ttgttacaag    3960
gtctcccact ttcagtgaca acagcacgcc accggctgtg ccccagacct atcaggtcgg    4020
gtacttgcat gctccaactg gcagtggaaa gagcaccaag gtccctgtcg cgtatgccgc    4080
ccaggggtac aaagtactag tgcttaaccc ctcggtagct gccaccctgg ggtttggggc    4140
gtacctatcc aaggcacatg gcatcaatcc caacattagg actggagtca ggaccgtgat    4200
gaccggggag gccatcacgt actccacata tggcaaattt ctcgccgatg ggggctgcgc    4260
tagcggcgcc tatgacatca tcatatgcga tgaatgccac gctgtggatg ctacctccat    4320
tctcggcatc ggaacggtcc ttgatcaagc agagacagcc ggggtcagac taactgtgct    4380
ggctacggcc acaccccccg ggtcagtgac aacccccat cccgatatag aagaggtagg    4440
cctcgggcgg gagggtgaga tccccttcta tgggagggcg attcccctat cctgcatcaa    4500
gggagggaga cacctgattt tctgccactc aaagaaaaag tgtgacgagc tcgcggcggc    4560
ccttcggggc atgggcttga atgccgtggc atactataga ggggttggacg tctccataat    4620
accagctcag ggagatgtgg tggtcgtcgc caccgacgcc ctcatgacgg ggtacactgg    4680
agactttgac tccgtgatcg actgcaatgt agccggtcacc caagctgtcg acttcagcct    4740
ggaccccacc ttcactataa ccacacagac tgtcccacaa gacgctgtct cacgcagtca    4800
gcgccgcggg cgcacaggta gaggaagaca gggcacttat aggtatgttt ccactggtga    4860
acgagcctca ggaatgtttg acagtgtagt gctttgtgag tgctacgacg cagggctgc    4920
gtggtacgat ctcacaccag cggagaccac cgtcaggctt agagcgtatt tcaacacgcc    4980
cggcctaccc gtgtgtcaag accatcttga attttgggag gcagttttca ccggcctcac    5040
acacatagac gcccacttcc tctcccaaac aaagcaagcg ggggagaact tcgcgtacct    5100
agtagcctac caagctacgg tgtgcgccag agccaaggcc cctcccccgt cctgggacgc    5160
catgtggaag tgcctggccc gactcaagcc tacgcttgcg ggcccacac ctctcctgta    5220
ccgtttgggc cctattacca atgaggtcac cctcacacac cctgggacga agtacatcgc    5280
cacatgcatg caagctgacc ttgaggtcat gaccagcacg tgggtcctag ctggaggagt    5340
cctggcagcc gtcgccgcat attgcctggc gactggatgc gtttccatca tcggccgctt    5400
gcacgtcaac cagcgagtcg tcgttgcgcc ggataaggag gtcctgtatg aggcttttga    5460
tgagatggag gaatgcgcct ctagggcggc tctcatcgaa gaggggcagc ggatagccga    5520
gatgttgaag tccaagatcc aaggcttgct gcagcaggcc tctaagcagg cccaggacat    5580
acaacccgct atgcaggctt catggcccaa agtggaacaa ttttgggcca gacacatgtg    5640
gaacttcatt agcggcatcc aatacctcgc aggattgtca acactgccag ggaaccccgc    5700
ggtggcttcc atgatggcat tcagtgccgc cctcaccagt ccgttgtcga ccagtaccac    5760
catccttctc aacatcatgg gaggctggtt agcgtcccag atcgcaccac ccgcggggc    5820
```

```
caccggcttt gtcgtcagtg gcctggtggg ggctgccgtg ggcagcatag gcctgggtaa     5880
ggtgctggtg gacatcctgg caggatatgg tgcgggcatt tcgggggccc tcgtcgcatt     5940
caagatcatg tctggcgaga agccctctat ggaagatgtc atcaatctac tgcctgggat     6000
cctgtctccg ggagccctgg tggtggggt catctgcgcg gccattctgc gccgccacgt      6060
gggaccgggg gagggcgcgg tccaatggat gaacaggctt attgcctttg cttccagagg     6120
aaaccacgtc gcccctactc actacgtgac ggagtcggat gcgtcgcagc gtgtgaccca     6180
actacttggc tctcttacta taaccagcct actcagaaga ctccacaatt ggataactga     6240
ggactgcccc atcccatgct ccggatcctg gctccgcgac gtgtgggact gggtttgcac     6300
catcttgaca gacttcaaaa attggctgac ctctaaattg ttccccaagc tgcccggcct     6360
cccttcatc tcttgtcaaa aggggtacaa gggtgtgtgg gccggcactg gcatcatgac      6420
cacgcgctgc ccttgcggcg ccaacatctc tggcaatgtc cgcctgggct ctatgaggat     6480
cacagggcct aaaacctgca tgaacacctg gcagggggacc tttcctatca attgctacac    6540
ggagggccag tgcgcgccga accccccac gaactacaag accgccatct ggagggtggc      6600
ggcctcggag tacgcggagg tgacgcagca tgggtcgtac tcctatgtaa caggactgac     6660
cactgacaat ctgaaaattc cttgccaact accttctcca gagttttcct cctgggtgga    6720
cggtgtgcag atccataggt ttgcacccac accaaagccg ttttccggg atgaggtctc      6780
gttctgcgtt gggcttaatt cctatgctgt cgggtcccag cttccctgtg aacctgagcc     6840
cgacgcagac gtattgaggt ccatgctaac agatccgccc cacatcacgg cggagactgc     6900
ggcgcggcgc ttggcacggg gatcacctcc atctgaggcg agctcctcag tgagccagct     6960
atcagcaccg tcgctgcggg ccacctgcac cacccacagc aacacctatg acgtggacat     7020
ggtcgatgcc aacctgctca tggagggcgg tgtggctcag acagagcctg agtccagggt    7080
gcccgttctg gactttctcg agccaatggc cgaggaagag agcgaccttg agccctcaat    7140
accatcggag tgcatgctcc ccaggagcgg gttttccacgg gccttaccgg cttgggcacg    7200
gcctgactac aacccgccgc tcgtggaatc gtggaggagg ccagattacc aaccgcccac    7260
cgttgctggt tgtgctctcc cccccccaa gaaggccccg acgcctcccc caaggagacg     7320
ccggacagtg ggtctgagcg agagcaccat atcagaagcc ctccagcaac tggccatcaa    7380
gaccctttggc cagccccct cgagcggtga tgcaggctcg tccacggggg cgggcgccgc    7440
cgaatccggc ggtccgacgt ccctggtga gccggcccc tcagagacag gttccgcctc       7500
ctctatgccc ccctcgagg gggagcctgg agatccggac ctggagtctg atcaggtaga     7560
gcttcaacct cccccccagg gggggggggt agctcccggt tcgggctcgg ggtcttggtc     7620
tacttgctcc gaggaggacg ataccaccgt gtgctgctcc atgtcatact cctggaccgg    7680
ggctctaata actccctgta gccccgaaga ggaaaagttg ccaatcaacc ctttgagtaa    7740
ctcgctgttg cgataccata acaaggtgta ctgtacaaca tcaaagagcg cctcacagag    7800
ggctaaaaag gtaactttg acaggacgca agtgctcgac gcccattatg actcagtctt      7860
aaaggacatc aagctagcgg cttccaaggt cagcgcaagg ctcctcacct tggaggaggc    7920
gtgccagttg actccacccc attctgcaag atcaagtat ggattcgggg ccaaggaggt      7980
ccgcagcttg tccgggaggg ccgttaacca catcaagtcc gtgtggaagg acctcctgga    8040
agacccacaa acaccaattc ccacaaccat catggccaaa aatgaggtgt tctgcgtgga   8100
ccccgccaag gggggtaaga aaccagctcg cctcatcgtt tacccgtacc tcggcgtccg    8160
ggtctgcgag aaaatggccc tctatgacat tacacaaaag cttcctcagg cggtaatggg    8220
```

| | |
|---|---|
| agcttcctat ggcttccagt actcccctgc ccaacgggtg gagtatctct tgaaagcatg | 8280 |
| ggcggaaaag aaggacccca tgggtttttc gtatgatacc cgatgcttcg actcaaccgt | 8340 |
| cactgagaga gacatcagga ccgaggagtc catataccag gcctgctccc tgcccgagga | 8400 |
| ggcccgcact gccatacact cgctgactga gagactttac gtaggagggc ccatgttcaa | 8460 |
| cagcaagggt caaacctgcg gttacagacg ttgccgcgcc agcggggtgc taaccactag | 8520 |
| catgggtaac accatcacat gctatgtgaa agccctagcg gcctgcaagg ctgcggggat | 8580 |
| agttgcgccc acaatgctgg tatgcggcga tgacctagta gtcatctcag aaagccaggg | 8640 |
| gactgaggag gacgagcgga acctgagagc cttcacggag gccatgacca ggtactctgc | 8700 |
| ccctcctggt gatcccccca gaccggaata tgacctggag ctaataacat cctgttcctc | 8760 |
| aaatgtgtct gtggcgttgg gcccgcgggg ccgccgcaga tactacctga ccagagaccc | 8820 |
| aaccactcca ctcgcccggg ctgcctggga aacagttaga cactccccta tcaattcatg | 8880 |
| gctgggaaac atcatccagt atgctccaac catatgggtt cgcatggtcc taatgacaca | 8940 |
| cttcttctcc attctcatgg tccaagacac cctggaccag aacctcaact ttgagatgta | 9000 |
| tggatcagta tactccgtga atcctttgga ccttccagcc ataattgaga ggttacacgg | 9060 |
| gcttgacgcc ttttctatgc acacatactc tcaccacgaa ctgacgcggg tggcttcagc | 9120 |
| cctcagaaaa cttggggcgc cacccctcag ggtgtgaag agtcgggctc gcgcagtcag | 9180 |
| ggcgtccctc atctcccgtg agggaaagc ggccgtttgc ggccgatatc tcttcaattg | 9240 |
| ggcggtgaag accaagctca aactcactcc attgccggag gcgcgcctac tggacttatc | 9300 |
| cagttggttc accgtcggcg ccggcggggg cgacattttt cacagcgtgt cgcgcgcccg | 9360 |
| acccccgctca ttactcttcg gcctactcct acttttcgta ggggtaggcc tcttcctact | 9420 |
| ccccgctcgg tagagcggca cactaggt acactccata gctaactgtt cctttttttt | 9480 |
| tttttttttt tttttttttt tttttttttt tttttcttt tttttttttt ccctcttct | 9540 |
| tcccttctca tcttattcta ctttctttct tggtggctcc atcttagccc tagtcacggc | 9600 |
| tagctgtgaa aggtccgtga gccgcatgac tgcagagagt gccgtaactg gtctctctgc | 9660 |
| agatcatgt | 9669 |

<210> SEQ ID NO 55
<211> LENGTH: 9669
<212> TYPE: DNA
<213> ORGANISM: Hepatitis C virus

<400> SEQUENCE: 55

| | |
|---|---|
| acctgcccct aatagggcg acactccgcc atgaatcact ccctgtgag gaactactgt | 60 |
| cttcacgcag aaagcgccta gccatggcgt tagtatgagt gtcgtacagc ctccaggccc | 120 |
| cccctcccg ggagagccat agtggtctgc ggaaccggtg agtacaccgg aattgccggg | 180 |
| aagactgggt cctttcttgg ataaacccac tctatgcccg gccatttggg cgtgcccccg | 240 |
| caagactgct agccgagtag cgttgggttg cgaaaggcct tgtggtactg cctgataggg | 300 |
| cgcttgcgag tgccccggga ggtctcgtag accgtgcacc atgagcacga atcctaaacc | 360 |
| tcaaagaaaa accaaagaa acaccaaccg ccgcccacag gacgtcaagt tcccgggcgg | 420 |
| tggtcagatc gttggtggag tttacttgtt gccgcgcagg ggcctaggt tgggtgtgcg | 480 |
| cgcaactcgg aagacttcag aacggtcgca acccgtgga cggcgtcagc ctatccccaa | 540 |
| ggcgcgccag cccacgggcc ggtcctgggg tcaacccggg tacccttggc ccctttatgc | 600 |
| caatgagggc ctcgggtggg caggtggtt gctctccccc cgaggctctc ggcctaattg | 660 |

```
gggcccaat gaccccggc ggaaatcgcg caacttgggt aaggtcatcg atacccctgac    720 gtgcggattc gccgacctca tggggtacat cccgctcgta ggcggcccccg ttgggggcgt    780 cgcaagggct ctcgcacacg gtgtgagggt ccttgaggac ggggtaaact atgcaacagg    840
gaatttaccc ggttgctctt tctctatctt tatccttgca cttctttcat gcctgactgt    900
cccgacctct gccgttccct accgaaatgc ctctggggtt tatcatgtca ccaatgattg    960
cccaaactct tctatcgtct atgaggctga agacctgatc ttacacgcac ctggttgcgt   1020
gccctgtgtt aggcagggta atgtcagtag gtgctgggtc cagatcaccc ccacactgtc   1080
agccccgagc ctcggagcgg tcacggctcc tcttcggagg gccgttgact acttagcggg   1140
gggggctgcc ctttgctccg cgttatacgt cggagacgcg tgcggggcag tgttttttggt   1200 aggtcaaatg ttcacctata gccctcgccg gcataatgtt gtgcaggact gcaactgttc   1260
catttacagt ggccacatca ccggccaccg gatggcatgg gacatgatga tgaattggtc   1320
acctacaaca gctttggtga tggcccagtt gttacggatt ccccaggtgg tcattgacat   1380
cattgccggg gcccactggg gggtcttgtt cgccgccgca tactacgcgt cggcggctaa   1440
ctgggccaag gttgtgctgg tcctgtttct gtttgcgggg gtcgatgcca gcacccgcac   1500
tgtgggtggt agtgcggccc aaggcgcgcg cgggctcgct tcactttttca ccctgggcc   1560 gcagcagaac ttgcagctca taaataccaa cgggagctgg cacatcaaca gaactgccct   1620
taactgtaat gacagcctcc agactgggtt tgtagccggc ctcctgtatt atcacaagtt   1680
caactccact gggtgtccgc agcggatggc tagctgtagg cccctcgccg cattcgacca   1740
gggctgggga actatcagct atgccgccgt gtcgggcccc agtgatgaca gcccctattg   1800
ctggcactac cccccacgcc cgtgcggaat agtgccagcg cgaggtgtct gcggtccggt   1860
ctattgtttt acacctagcc cggtggtcgt cggcaccaca gaccgcaagg ggaatcccac   1920
ttacagttgg ggcgaaaatg agactgacat cttttctcttg aacaacacga ggcccccctac   1980 tggcaactgg tttggctgca cctggatgaa ttccacaggg tttgtcaaga cttgcggggc   2040
tccaccctgc aacttagggc ctacaggcaa caatagcctt aagtgtccta ctgattgctt   2100
ccgcaagcac ccagacgcca cctacaccaa gtgtgggtca ggaccctggc tcactcccg   2160 gtgtctggtg cattacccctt accggttgtg gcattacccg tgcaccctaa attacaccat   2220
cttcaaggtg cgcatgtaca ttgggggcct cgagcacagg ctcgaggtgg catgcaactg   2280
gacccgtggt gagcggtgtg atcttgaaga cagggatagg gccgagctga gcccgctcct   2340
acataccacc acgcagtggg ccatattgcc gtgctctttc acacccacac ccgctcttag   2400
cactggtctc atacacttac atcaaaatat agtagacacc cagtatcttt acggtctgag   2460
ctccagcatc gtctcgtggg ccgttaagtg ggagtacata gtgctggcct tcttattact   2520
tgctgatgcc cgtatttgta cttgcctatg gatcatgctc ctggtttgtc aggccgaagc   2580
ggccctggag aacgtcattg tcctaaacgc ggctgcggct gcgggactc atgggttttt   2640 ctggggcctg ctcgtcatct gcttcgcctg gcacttcaag ggcaggttgg tccctggggc   2700
cacctacctt tgcttgggca tttggccatt actcttactc cttttcctcc tgccccaaag   2760
ggctctagcc ctggactcaa gcgatggcgg gactgtgggt tgtcttgtgt aaccatcct   2820 tacaatcttc acactcaccc ccgggtacaa gaagatggta gtgttggtca tatggtggct   2880
tcagtatttc atagcccggg tagaggcctt tatccatgtg tgggtgcccc cgttgcaggt   2940 tagggggtggt cgtgatgcta ttatcatgct cacatgcctt ttccatcctg ccctgggggtt   3000 tgaggtcacg aaaatcctcc tcgggatact aggtccttttg tacctgctgc agtactcgct   3060
```

```
catcaagctg ccttatttca tcagggcgcg cgccctgctg agggcgtgcc tgctagcgaa    3120
gcacttggcc tgtggcaggt acgtgcaggc ggccttgctc caccttggta ggctgaccgg    3180
aacgtacatt tatgaccacc ttgcccccat gaaggattgg gcagcgtccg ggctgcgcga    3240
cttagcagtg gccacggagc ccatcatatt ctcccctatg gagacgaagg tcatcacgtg    3300
gggggctgac acggccgcat gtggggacat acttgccggc cttcctgtat cagctaggcg    3360
aggccatgaa atcttcctgg ggccagccga tgacatcaga gagggggct ggcgacttct     3420 cgctcccatc actgcttatg cccagcaaac acgaggcctc ctgggcgcca tagtggtgag    3480
tatgacgggg cgtgacagga cagaacaggc cggggaagtc caaatcctgt ccacagtctc    3540
tcagtccttc ctcggaacaa ccatctcggg ggttttgtgg actgtttacc acggagctgg    3600
caacaagact ctagccggct tacggggtcc ggtcacgcag atgtactcga gtgctgaggg    3660
ggacttggta ggctggccca gccccctgg gaccaggtct ttggagccgt gcaagtgtgg     3720
agccgtcgac ctatatctgg tcacgcgaa cgctgatgtc atcccggctc ggagacgcgg     3780
ggacaagcgg ggagcattgc tctccccgag acccatttcg accttgaagg gtcctcggg     3840 ggggccggtg ctctgcccta ggggccacgt cgttgggctc ttccgagcag ctgtgtgctc    3900
tcggggcgtg gccaaatcca tcgatttcat ccccgttgag acactcgacg ttgttacaag    3960
gtctcccact ttcagtgaca acagcacgcc accggctgtg cccagacct atcaggtcgg    4020 gtacttgcat gctccaactg gcagtggaaa gagcaccaag gtccctgtcg cgtatgccgc    4080
ccaggggtac aaagtactag tgcttaaccc ctcggtagct gccaccctgg ggtttggggc    4140
gtacctatcc aaggcacatg gcatcaatcc caacattagg actggagtca ggaccgtgat    4200
gaccggggag gccatcacgt actccacata tggcaaattt ctcgccgatg ggggctgcgc    4260
tagcggcgcc tatgacatca tcatatgcga tgaatgccac gctgtggatg ctacctccat    4320
tctcggcatc ggaacggtcc ttgatcaagc agagacagcc ggggtcagac taactgtgct    4380
ggctacggcc acacccccg ggtcagtgac aaccccccat cccgatatag aagaggtagg    4440
cctcgggcgg gagggtgaga tccccttcta tgggagggcg attccccctat cctgcatcaa   4500 gggagggaga cacctgattt tctgccactc aaagaaaaag tgtgacgagc tcgcggcggc    4560
ccttcggggc atgggcttga atgccgtggc atactataga ggggttggacg tctccataat   4620 accagctcag ggagatgtgg tggtcgtcgc caccgacgcc ctcatgacgg ggtacactgg    4680
agactttgac tccgtgatcg actgcaatgt agcggtcacc caagctgtcg acttcagcct    4740
ggaccccacc ttcactataa ccacacagac tgtcccacaa gacgctgtct cacgcagtca    4800
gcgccgcggg cgcacaggta gaggaagaca gggcacttat aggtatgttt ccactggtga    4860
acgagcctca ggaatgtttg acagtgtagt gctttgtgag tgctacgacg caggggctgc    4920
gtggtacgat ctcacaccag cggagaccac cgtcaggctt agagcgtatt tcaacacgcc    4980
cggcctaccc gtgtgtcaag accatcttga attttggga gcagttttca ccggcctcac    5040
acacatagac gccacttcc tctcccaaac aaagcaagcg ggggagaact tcgcgtacct    5100
agtagcctac caagctacgg tgtgcgccag agccaaggcc cctcccccgt cctgggacgc    5160
catgtggaag tgcctggccc gactcaagcc tacgcttgcg ggccccacac ctctcctgta    5220
ccgtttgggc cctattacca atgaggtcac cctcacacac cctgggacga agtacatcgc    5280
cacatgcatg caagctgacc ttgaggtcat gaccagcacg tgggtcctag ctggaggagt    5340
cctggcagcc gtcgccgcat attgcctggc gactggatgc gtttccatca tcggccgctt    5400
gcacgtcaac cagcgagtcg tcgttgcgcc ggataaggag gtcctgtatg aggcttttga    5460
```

```
tgagatggag gaatgcgcct ctagggcggc tctcatcgaa gaggggcagc ggatagccga   5520
gatgttgaag tccaagatcc aaggcttgct gcagcaggcc tctaagcagg cccaggacat   5580
acaacccgct atgcaggctt catggcccaa agtggaacaa ttttgggcca gacacatgtg   5640
gaacttcatt agcggcatcc aatacctcgc aggattgtca acactgccag ggaaccccgc   5700
ggtggcttcc atgatggcat tcagtgccgc cctcaccagt ccgttgtcga ccagtaccac   5760
catccttctc aacatcatgg gaggctggtt agcgtcccag atcgcaccac ccgcggggc    5820 caccggcttt gtcgtcagtg gcctggtggg ggctgccgtg ggcagcatag gcctgggtaa   5880
ggtgctggtg gacatcctgg caggatatgg tgcgggcatt tcgggggccc tcgtcgcatt   5940
caagatcatg tctggcgaga agccctctat ggaagatgtc atcaatctac tgcctgggat   6000
cctgtctccg ggagccctgg tggtgggggt catctgcgcg ccattctgc gccgccacgt    6060 gggaccgggg gagggcgcgg tccaatggat gaacaggctt attgcctttg cttccagagg   6120
aaaccacgtc gcccctactc actacgtgac ggagtcggat gcgtcgcagc gtgtgaccca   6180
actacttggc tctcttacta taaccagcct actcagaaga ctccacaatt ggataactga   6240
ggactgcccc atcccatgct ccggatcctg gctccgcgac gtgtgggact gggtttgcac    6300
catcttgaca gacttcaaaa attggctgac ctctaaattg ttccccaagc tgcccggcct   6360 cccccttcatc tcttgtcaaa agggtacaa gggtgtgtgg gccggcactg gcatcatgac   6420
cacgcgctgc ccttgcggcg ccaacatctc tggcaatgtc cgcctgggct ctatgaggat   6480
cacagggcct aaaacctgca tgaacacctg gcagggacc tttcctatca attgctacac    6540
ggagggccag tgcgcgccga aaccccccac gaactacaag accgccatct ggagggtggc   6600
ggcctcggag tacgcggagg tgacgcagca tgggtcgtac tcctatgtaa caggactgac   6660
cactgacaat ctgaaaattc cttgccaact accttctcca gagttttcct cctgggtgga   6720
cggtgtgcag atccataggt ttgcacccac accaaagccg ttttccggg atgaggtctc    6780 gttctgcgtt gggcttaatt cctatgctgt cgggtcccag cttccctgtg aacctgagcc   6840
cgacgcagac gtattgaggt ccatgctaac agatccgccc cacatcacgg cggagactgc   6900
ggcgcggcgc ttggcacggg gatcacctcc atctgaggcg agctcctcag tgagccagct   6960
atcagcaccg tcgctgcggg ccacctgcac cacccacagc aacacctatg acgtggacat   7020
ggtcgatgcc aacctgctca tggagggcgg tgtggctcag acagagcctg agtccagggt   7080
gcccgttctg gactttctcg agccaatggc cgaggaagag agcgaccttg agccctcaat   7140
accatcggag tgcatgctcc ccaggagcgg gtttccacgg gccttaccgg cttgggcacg   7200
gcctgactac aacccgccgc tcgtggaatc gtggaggagg ccagattacc aaccgcccac   7260
cgttgctggt tgtgctctcc cccccccaa gaaggccccg acgcctcccc caaggagacg    7320
ccggacagtg ggtctgagcg agagcaccat atcagaagcc ctccagcaac tggccatcaa   7380
gacctttggc cagcccccct cgagcggtga tgcaggctcg tccacggggg cgggcgccgc   7440
cgaatccggc ggtccgacgt ccctggtga gccggccccc tcagacacag gttccgcctc    7500
ctctatgccc ccctcgagg gggagcctgg agatccggac ctggagtctg atcaggtaga   7560
gcttcaacct ccccccagg gggggggggt agctcccggt tcgggctcgg ggtcttggtc    7620
tacttgctcc gaggaggacg ataccaccgt gtgctgctcc atgtcatact cctgaccgg    7680 ggctctaata actccctgta gccccgaaga ggaaaagttg ccaatcaacc ctttgagtaa   7740
ctcgctgttc cgataccata acaaggtgta ctgtacaaca tcaaagagcg cctcacagag   7800
ggctaaaaag gtaacttttg acaggacgca agtgctcgac gcccattatg actcagtctt   7860
```

-continued

| | |
|---|---|
| aaaggacatc aagctagcgg cttccaaggt cagcgcaagg ctcctcacct tggaggaggc | 7920 |
| gtgccagttg actccacccc attctgcaag atccaagtat ggattcgggg ccaaggaggt | 7980 |
| ccgcagcttg tccgggaggg ccgttaacca catcaagtcc gtgtggaagg acctcctgga | 8040 |
| agacccacaa acaccaattc ccacaaccat catggccaaa aatgaggtgt tctgcgtgga | 8100 |
| ccccgccaag gggggtaaga aaccagctcg cctcatcgtt taccctgacc tcggcgtccg | 8160 |
| ggtctgcgag aaaatggccc tctatgacat tacacaaaag cttcctcagg cggtaatggg | 8220 |
| agcttcctat ggcttccagt actcccctgc ccaacgggtg gagtatctct tgaaagcatg | 8280 |
| ggcggaaaag aaggacccca tgggttttc gtatgatacc cgatgcttcg actcaaccgt | 8340 |
| cactgagaga gacatcagga ccgaggagtc catataccag gcctgctccc tgcccgagga | 8400 |
| ggcccgcact gccatacact cgctgactga gagactttac gtaggagggc ccatgttcaa | 8460 |
| cagcaagggt caaacctgcg gttacagacg ttgccgcgcc agcggggtgc taaccactag | 8520 |
| catgggtaac accatcacat gctatgtgaa agccctagcg gcctgcaagg ctgcggggat | 8580 |
| agttgcgccc acaatgctgg tatgcggcga tgacctagta gtcatctcag aaagccaggg | 8640 |
| gactgaggag gacgagcgga acctgagagc cttcacggag gccatgacca ggtactctgc | 8700 |
| ccctcctggt gatcccccca gaccggaata tgacctggag ctaataacat cctgttcctc | 8760 |
| aaatgtgtct gtggcgttgg gcccgcgggg ccgccgcaga tactacctga ccagagaccc | 8820 |
| aaccactcca ctcgcccggg ctgcctggga aacagttaga cactccccta tcaattcatg | 8880 |
| gctgggaaac atcatccagt atgctccaac catatgggtt cgcatggtcc taatgacaca | 8940 |
| cttcttctcc attctcatgg tccaagacac cctggaccag aacctcaact ttgagatgta | 9000 |
| tggatcagta tactccgtga atcctttgga ccttccagcc ataattgaga ggttacacgg | 9060 |
| gcttgacgcc ttttctatgc acacatactc tcaccacgaa ctgacgcggg tggcttcagc | 9120 |
| cctcagaaaa cttggggcgc caccctcag ggtgtggaag agtcgggctc gcgcagtcag | 9180 |
| ggcgtccctc atctcccgtg gagggaaagc ggccgtttgc ggccgatatc tcttcaattg | 9240 |
| ggcggtgaag accaagctca aactcactcc attgccggag gcgcgcctac tggacttatc | 9300 |
| cagttggttc accgtcggcg ccggcggggg cgacattttt cacagcgtgt cgcgcgcccg | 9360 |
| accccgctca ttactcttcg gcctactcct acttttcgta ggggtaggcc tcttcctact | 9420 |
| ccccgctcgg tagagcggca cactaggt acactccata gctaactgtt ccttttttt | 9480 |
| tttttttt ttttttttt ttttttttt tttttctttt ttttttttt ccctcttct | 9540 |
| tcccttctca tcttattcta ctttcttct tggtggctcc atcttagccc tagtcacggc | 9600 |
| tagctgtgaa aggtccgtga gccgcatgac tgcagagagt gccgtaactg gtctctctgc | 9660 |
| agatcatgt | 9669 |

<210> SEQ ID NO 56
<211> LENGTH: 9669
<212> TYPE: DNA
<213> ORGANISM: Hepatitis C virus

<400> SEQUENCE: 56

| | |
|---|---|
| acctgcccct aatagggcg acactccgcc atgaatcact cccctgtgag gaactactgt | 60 |
| cttcacgcag aaagcgccta gccatggcgt tagtatgagt gtcgtacagc ctccaggccc | 120 |
| ccccctcccg ggagagccat agtggtctgc ggaaccggtg agtacaccgg aattgccggg | 180 |
| aagactgggt cctttcttgg ataaacccac tctatgcccg gccatttggg cgtgcccccg | 240 |
| caagactgct agccgagtag cgttgggttg cgaaaggcct tgtggtactg cctgataggg | 300 |

```
cgcttgcgag tgccccggga ggtctcgtag accgtgcacc atgagcacga atcctaaacc    360
tcaaagaaaa accaaaagaa acaccaaccg ccgcccacag gacgtcaagt tcccgggcgg    420
tggtcagatc gttggtggag tttacttgtt gccgcgcagg ggccctaggt tgggtgtgcg    480
cgcaactcgg aagacttcag aacggtcgca accccgtgga cggcgtcagc ctatcccaa     540 ggcgcgccag cccacgggcc ggtcctgggg tcaacccggg tacccttggc ccctttatgc    600
caatgagggc ctcgggtggg cagggtggtt gctctccccc cgaggctctc ggcctaattg    660 gggcccccaat gaccccggc ggaaatcgcg caacttgggt aaggtcatcg atacccctgac   720 gtgcggattc gccgacctca tggggtacat cccgctcgta ggcggccccg ttggggggcgt   780 cgcaagggct ctcgcacacg gtgtgagggt ccttgaggac ggggtaaaact atgcaacagg   840 gaatttaccc ggttgctctt tctctatctt tatccttgca cttctttcat gcctgactgt    900
cccgacctct gccgttccct accgaaatgc ctcggggtt tatcatgtca ccaatgattg     960
cccaaactct tctatcgtct atgaggctga agacctgatc ttacacgcac ctggttgcgt   1020
gccctgtgtt aggcagggta atgtcagtag gtgctgggtc cagatcaccc ccacactgtc   1080
agccccgagc ctcggagcgg tcacggctcc tcttcggagg gccgttgact acttagcggg   1140
gggggctgcc ctttgctccg cgttatacgt cggagacgcg tgcggggcag tgttttggt    1200 aggtcaaatg ttcacctata gccctcgccg gcataatgtt gtgcaggact gcaactgttc   1260
catttacagt ggccacatca ccggccaccg gatggcatgg gacatgatga tgaattggtc   1320
acctacaaca gctttggtga tggcccagtt gttacggatt ccccaggtgg tcattgacat   1380
cattgccggg gcccactggg gggtcttgtt cgccgccgca tactacgcgt cggcggctaa   1440
ctgggccaag gttgtgctgg tcctgttttct gtttgcgggg gtcgatgcca gcacccgcac   1500
tgtgggtggt agtgcggccc aaggcgcgcg cgggctcgct tcacttttca cccctgggcc   1560
gcagcagaac ttgcagctca taaataccaa cgggagctgg cacatcaaca gaactgccct   1620
taactgtaat gacagcctcc agactgggtt tgtagccggc ctcctgtatt atcacaagtt   1680
caactccact gggtgtccgc agcggatggc tagctgtagg cccctcgccg cattcgacca   1740
gggctgggga actatcagct atgccgccgt gtcgggcccc agtgatgaca gccctattg    1800 ctggcactac cccccacgcc cgtgcggaat agtgccagcg cgaggtgtct gcggtccggt   1860
ctattgtttt acacctagcc cggtggtcgt cggcaccaca gaccgcaagg ggaatcccac   1920
ttacagttgg ggcgaaaatg agactgacat cttcctcttg aacaacacga ggccccctac   1980
tggcaactgg tttggctgca cctggatgaa ttccacaggg tttgtcaaga cttgcgggc    2040 tccacccctgc aacttagggc ctacaggcaa caatagcctt aagtgtccta ctgattgctt   2100
ccgcaagcac ccagacgcca cctacaccaa gtgtgggtca ggaccctggc tcactccccg   2160
gtgtctggtg cattacccctt accggttgtg gcattacccg tgcacccctaa attacaccat   2220 cttcaaggtg cgcatgtaca ttgggggcct cgagcacagg ctcgaggtgg catgcaactg   2280
gacccgtggt gagcggtgtg atcttgaaga cagggatagg gccgagctga gcccgctcct   2340
acataccacc acgcagtggg ccatattgcc gtgctctttc acacccacac ccgctcttag   2400
cactggtctc atacacttac atcaaaatat agtagacacc cagtatcttt acggtctgag   2460
ctccagcatc gtctcgtggg ccgttaagtg ggagtacata gtgctggcct tcttattact   2520
tgctgatgcc cgtatttgta cttgcctatg gatcatgctc ctggtttgtc aggccgaagc   2580
ggccctggag aacgtcattg tcctaaacgc tgctgcggct gcgggactct atgggtttt    2640 ctggggcctg ctcgtcatct gcttcgcctg gcacttcaag ggcaggttgg tccctgggc    2700
```

```
cacctacctt tgcttgggca tttggccgtt actcttactc cttttcctcc tgccccaaag    2760
ggctctagcc ctggactcaa gcgatggcgg gactgtgggt tgtcttgtgt taaccatcct    2820
tacaatcttc acactcaccc ccgggtacaa gaagatggta gtgttggtca tatggtggct    2880
tcagtatttc atagcccggg tagaggcctt tatccatgtg tgggtgcccc cgttgcaggt    2940
taggggtggt cgtgatgcta ttatcatgct cacatgcctt ttccatcctg ccctggggtt    3000
tgaggtcacg aaaatcctcc tcgggatact aggtcctttg tacctgctgc agtactcgct    3060
catcaagctg ccttatttca tcagggcgcg cgccctgctg agggcgtgcc tgctagcgaa    3120
gcacttggcc tgtggcaggt acgtgcaggc ggccttgctc caccttggta ggctgaccgg    3180
aacgtacatt tatgaccacc ttgcccccat gaaggattgg gcagcgtccg ggctgcgcga    3240
cttagcagtg gccacggagc ccatcatatt ctcccctatg gagacgaagg tcatcacgtg    3300
gggggctgac acggccgcat gtggggacat acttgccggc cttcctgtat cagctaggcg    3360
aggccatgaa atcttcctgg ggccagccga tgacatcaga gagggggggct ggcgacttct    3420 cgctcccatc actgcttatg cccagcaaac acgaggcctc ctgggcgcca tagtggtgag    3480
tatgacgggg cgtgacagga cagaacaggc cggggaagtc caaatcctgt ccacagtctc    3540
tcagtccttc ctcggaacaa ccatctcggg ggttttgtgg actgtttacc acggagctgg    3600
caacaagact ctagccggct tacggggtcc ggtcacgcag atgtactcga gtgctgaggg    3660
ggacttggta ggctggccca gcccccctgg gaccaggtct ttggagccgt gcaagtgtgg    3720
agccgtcgac ctatatctgg tcacgcgaa cgctgatgtc atcccggctc ggagacgcg    3780 ggacaagcgg ggagcattgc tctccccgag acccatttcg accttgaagg ggtcctcggg    3840
ggggccggtg ctctgcccta ggggccacgt cgttgggctc ttccgagcag ctgtgtgctc    3900
tcggggcgtg gccaaatcca tcgatttcat ccccgttgag acactcgacg ttgttacaag    3960
gtctcccact ttcagtgaca acagcacgcc accggctgtg cccagacct atcaggtcgg    4020 gtacttgcat gctccaactg gcagtggaaa gagcaccaag gtccctgtcg cgtatgccgc    4080
ccaggggtac aaagtactag tgcttaaccc ctcggtagct gccaccctgg ggtttgggc    4140 gtacctatcc aaggcacatg gcatcaatcc caacattagg actggagtca ggaccgtgat    4200
gaccggggag gccatcacgt actccacata tggcaaattt ctcgccgatg ggggctgcgc    4260
tagcggcgcc tatgacatca tcatatgcga tgaatgccac gctgtggatg ctacctccat    4320
tctcggcatc ggaacggtcc ttgatcaagc agagacagcc ggggtcagac taactgtgct    4380
ggctacggcc acaccccccg ggtcagtgac aaccccccat cccgatatag aagaggtagg    4440
cctcgggcgg gagggtgaga tcccttcta tgggagggcg attccccctat cctgcatcaa    4500 gggagggaga cacctgattt tctgccactc aaagaaaaag tgtgacgagc tcgcggcggc    4560
ccttcggggc atgggcttga atgccgtggc atactataga gggttggacg tctccataat    4620
accagctcag ggagatgtgg tggtcgtcgc caccgacgcc ctcatgacgg ggtacactgg    4680
agactttgac tccgtgatcg actgcaatgt agcggtcacc caagctgtcg acttcagcct    4740
ggaccccacc ttcactataa ccacacagac tgtcccacaa gacgctgtct cacgcagtca    4800
gcgccgcggg cgcacaggta gaggaagaca gggcacttat aggtatgttt ccactggtga    4860
acgagcctca ggaatgtttg acagtgtagt gcttgtgag tgctacgacg caggggctgc    4920
gtggtacgat ctcacaccag cggagaccac cgtcaggctt agagcgtatt tcaacacgcc    4980
cggcctaccc gtgtgtcaag accatcttga atttttgggag gcagttttca ccggcctcac    5040
acacatagac gcccacttcc tctcccaaac aaagcaagcg ggggagaact tcgcgtacct    5100
```

-continued

```
agtagcctac caagctacgg tgtgcgccag agccaaggcc cctcccccgt cctgggacgc    5160
catgtggaag tgcctggccc gactcaagcc tacgcttgcg ggccccacac ctctcctgta    5220
ccgtttgggc cctattacca atgaggtcac cctcacacac cctgggacga agtacatcgc    5280
cacatgcatg caagctgacc ttgaggtcat gaccagcacg tgggtcctag ctggaggagt    5340
cctggcagcc gtcgccgcat attgcctggc gactggatgc gtttccatca tcggccgctt    5400
gcacgtcaac cagcgagtcg tcgttgcgcc ggataaggag gtcctgtatg aggcttttga    5460
tgagatggag gaatgcgcct ctagggcggc tctcatcgaa gaggggcagc ggatagccga    5520
gatgttgaag tccaagatcc aaggcttgct gcagcaggcc tctaagcagg cccaggacat    5580
acaacccgct atgcaggctt catgcccaa agtggaacaa ttttgggcca gacacatgtg    5640
gaacttcatt agcggcatcc aatacctcgc aggattgtca acactgccag gaacccgc    5700 ggtggcttcc atgatggcat tcagtgccgc cctcaccagt ccgttgtcga ccagtaccac    5760
catccttctc aacatcatgg gaggctggtt agcgtcccag atcgcaccac ccgcggggc    5820 caccggcttt gtcgtcagtg gcctggtggg ggctgccgtg ggcagcatag gcctgggtaa    5880
ggtgctggtg gacatcctgg caggatatgg tgcgggcatt tcgggggccc tcgtcgcatt    5940
caagatcatg tctggcgaga agccctctat ggaagatgtc atcaatctac tgcctgggat    6000
cctgtctccg ggagccctgg tggtgggggt catctgcgcg ccattctgc gccgccacgt    6060 gggaccgggg gagggcgcgg tccaatggat gaacaggctt attgcctttg cttccagagg    6120
aaaccacgtc gcccctactc actacgtgac ggagtcggat gcgtcgcagc gtgtgaccca    6180
actacttggc tctcttacta taaccagcct actcagaaga ctccacaatt ggataactga    6240
ggactgcccc atcccatgct ccggatcctg gctccgcgac gtgtgggact gggtttgcac    6300
catcttgaca gacttcaaaa attggctgac ctctaaattg ttccccaagc tgcccggcct    6360
ccccttcatc tcttgtcaaa aggggtacaa gggtgtgtgg gccggcactg gcatcatgac    6420
cacgcgctgc ccttgcggcg ccaacatctc tggcaatgtc cgcctgggct ctatgaggat    6480
cacagggcct aaaacctgca tgaacacctg gcagggacc tttcctatca attgctacac    6540
ggagggccag tgcgcgccga accccccac gaactacaag accgccatct ggaggggtggc    6600 ggcctcggag tacgcggagg tgacgcagca tgggtcgtac tcctatgtaa caggactgac    6660
cactgacaat ctgaaaattc cttgccaact accttctcca gagttttct cctgggtgga    6720 cggtgtgcag atccataggt ttgcacccac accaaagccg ttttccggg atgaggtctc    6780 gttctgcgtt gggcttaatt cctatgctgt cgggtcccag cttccctgtg aacctgagcc    6840
cgacgcagac gtattgaggt ccatgctaac agatccgccc cacatcacgg cggagactgc    6900
ggcgcggcgc ttggcacggg gatcacctcc atctgaggcg agctcctcag tgagccagct    6960
atcagcaccg tcgctgcggg ccacctgcac cacccacagc aacacctatg acgtggacat    7020
ggtcgatgcc aacctgctca tggagggcgg tgtggctcag acagagcctg agtccaggt    7080 gccccgttctg gactttctcg agccaatggc cgaggaagag agcgaccttg agccctcaat    7140
accatcggag tgcatgctcc ccaggagcgg gtttccacgg gccttaccgg cttgggcacg    7200
gcctgactac aacccgccgc tcgtggaatc gtgaggagg ccagattacc aaccgcccac    7260
cgttgctggt tgtgctctcc ccccccccaa gaaggcccccg acgcctcccc caaggagacg    7320
ccggacagtg ggtctgagcg agagcaccat atcagaagcc ctccagcaac tggccatcaa    7380 gaccttggc cagccccct cgagcggtga tgcaggctcg tccacggggg cgggcgccgc    7440
cgaatccggc ggtccgacgt cccctggtga gccggccccc tcagagacag gttccgcctc    7500
```

```
ctctatgccc ccctcgagg gggagcctgg agatccggac ctggagtctg atcaggtaga    7560
gcttcaacct cccccccagg gggggggggt agctcccggt tcgggctcgg ggtcttggtc    7620
tacttgctcc gaggaggacg ataccaccgt gtgctgctcc atgtcatact cctggaccgg    7680
ggctctaata actccctgta gccccgaaga ggaaaagttg ccaatcaacc ctttgagtaa    7740
ctcgctgttg cgataccata caaggtgta ctgtacaaca tcaaagagcg cctcacagag    7800
ggctaaaaag gtaacttttg acaggacgca agtgctcgac gcccattatg actcagtctt    7860
aaaggacatc aagctagcgg cttccaaggt cagcgcaagg ctcctcacct tggaggaggc    7920
gtgccagttg actccacccc attctgcaag atccaagtat ggattcgggg ccaaggaggt    7980
ccgcagcttg tccgggaggg ccgttaacca catcaagtcc gtgtggaagg acctcctgga    8040
agacccacaa acaccaattc ccacaaccat catggccaaa aatgaggtgt tctgcgtgga    8100
ccccgccaag gggggtaaga aaccagctcg cctcatcgtt taccctgacc tcggcgtccg    8160
ggtctgcgag aaaatggccc tctatgacat tacacaaaag cttcctcagg cggtaatggg    8220
agcttcctat ggcttccagt actcccctgc ccaacgggtg gagtatctct tgaaagcatg    8280
ggcggaaaag aaggaccccca tgggtttttc gtatgatacc cgatgcttcg actcaaccgt    8340
cactgagaga gacatcagga ccgaggagtc catataccag gcctgctccc tgcccgagga    8400
ggcccgcact gccatacact cgctgactga gagactttac gtaggagggc ccatgttcaa    8460
cagcaagggt caaacctgcg gttacagacg ttgccgcgcc agcggggtgc taaccactag    8520
catgggtaac accatcacat gctatgtgaa agccctagcg gcctgcaagg ctgcgggat    8580 agttgcgccc acaatgctgg tatgcggcga tgacctagta gtcatctcag aaagccaggg    8640
gactgaggag gacgagcgga acctgagagc cttcacggag gccatgacca ggtactctgc    8700
ccctcctggt gatcccccca gaccggaata tgacctggag ctaataacat cctgttcctc    8760
aaatgtgtct gtggcgttgg gccgcgggg ccgccgcaga tactacctga ccagagaccc    8820
aaccactcca ctcgcccggg ctgcctggga aacagttaga cactccccta tcaattcatg    8880
gctgggaaac atcatccagt atgctccaac catatgggtt cgcatggtcc taatgacaca    8940
cttcttctcc attctcatgg tccaagacac cctggaccag aacctcaact tgagatgta    9000 tggatcagta tactccgtga atcctttgga ccttccagcc ataattgaga ggttacacgg    9060
gcttgacgcc ttttctatgc acacatactc tcaccacgaa ctgacgcggg tggcttcagc    9120
cctcagaaaa cttggggcgc cacccctcag ggtgtggaag agtcgggctc gcgcagtcag    9180
ggcgtccctc atctcccgtg gagggaaagc ggccgtttgc ggccgatatc tcttcaattg    9240
ggcggtgaag accaagctca aactcactcc attgccggag gcgcgcctac tggacttatc    9300
cagttggttc accgtcggcg ccggcgggg cgacattttt cacagcgtgt cgcgcgcccg    9360
accccgctca ttactcttcg gcctactcct acttttcgta ggggtaggcc tcttcctact    9420
ccccgctcgg tagagcggca cactaggt acactccata gctaactgtt ccttttttt    9480 ttttttttt ttttttttt ttttttttt ttttcttttt ttttttttt ccctctttct    9540 tccctctca tcttattcta ctttctttct tggtggctcc atcttagccc tagtcacggc    9600
tagctgtgaa aggtccgtga gccgcatgac tgcagagagt gccgtaactg gtctctctgc    9660
agatcatgt                                                           9669

<210> SEQ ID NO 57
<211> LENGTH: 3030
<212> TYPE: PRT
<213> ORGANISM: Hepatitis C virus
```

```
<400> SEQUENCE: 57

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
            115                 120                 125

Gly Phe Ala Asp Leu Met Gly Tyr Ile Pro Leu Val Gly Gly Pro Val
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Thr Ser Ala Val
            180                 185                 190

Pro Tyr Arg Asn Ala Ser Gly Val Tyr His Val Thr Asn Asp Cys Pro
            195                 200                 205

Asn Ser Ser Ile Val Tyr Glu Ala Glu Asp Leu Ile Leu His Ala Pro
210                 215                 220

Gly Cys Val Pro Cys Val Arg Gln Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Val Phe Leu Val Gly
            275                 280                 285

Gln Met Phe Thr Tyr Ser Pro Arg Arg His Asn Val Val Gln Asp Cys
290                 295                 300

Asn Cys Ser Ile Tyr Ser Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Val Val Ile Asp Ile Ala Gly Ala His
            340                 345                 350

Trp Gly Val Leu Phe Ala Ala Tyr Tyr Ala Ser Ala Ala Asn Trp
            355                 360                 365

Ala Lys Val Val Leu Val Leu Phe Leu Phe Ala Gly Val Asp Ala Ser
370                 375                 380

Thr Arg Thr Val Gly Gly Ser Ala Ala Gln Gly Ala Arg Gly Leu Ala
385                 390                 395                 400

Ser Leu Phe Thr Pro Gly Pro Gln Gln Asn Leu Gln Leu Ile Asn Thr
                405                 410                 415
```

```
Asn Gly Ser Trp His Ile Asn Arg Thr Ala Leu Asn Cys Asn Asp Ser
            420                 425                 430

Leu Gln Thr Gly Phe Val Ala Gly Leu Leu Tyr Tyr His Lys Phe Asn
            435                 440                 445

Ser Thr Gly Cys Pro Gln Arg Met Ala Ser Cys Arg Pro Leu Ala Ala
450                 455                 460

Phe Asp Gln Gly Trp Gly Thr Ile Ser Tyr Ala Ala Val Ser Gly Pro
465                 470                 475                 480

Ser Asp Asp Lys Pro Tyr Cys Trp His Tyr Pro Pro Arg Pro Cys Gly
            485                 490                 495

Ile Val Pro Ala Arg Gly Val Cys Gly Pro Val Tyr Cys Phe Thr Pro
            500                 505                 510

Ser Pro Val Val Val Gly Thr Thr Asp Arg Lys Gly Asn Pro Thr Tyr
            515                 520                 525

Ser Trp Gly Glu Asn Glu Thr Asp Ile Phe Leu Leu Asn Asn Thr Arg
            530                 535                 540

Pro Pro Thr Gly Asn Trp Phe Gly Cys Thr Trp Met Asn Ser Thr Gly
545                 550                 555                 560

Phe Val Lys Thr Cys Gly Ala Pro Pro Cys Asn Leu Gly Pro Thr Gly
            565                 570                 575

Asn Asn Ser Leu Lys Cys Pro Thr Asp Cys Phe Arg Lys His Pro Asp
            580                 585                 590

Ala Thr Tyr Thr Lys Cys Gly Ser Gly Pro Trp Leu Thr Pro Arg Cys
            595                 600                 605

Leu Val His Tyr Pro Tyr Arg Leu Trp His Tyr Pro Cys Thr Leu Asn
            610                 615                 620

Tyr Thr Ile Phe Lys Val Arg Met Tyr Ile Gly Gly Leu Glu His Arg
625                 630                 635                 640

Leu Glu Val Ala Cys Asn Trp Thr Arg Gly Glu Arg Cys Asp Leu Glu
            645                 650                 655

Asp Arg Asp Arg Ala Glu Leu Ser Pro Leu Leu His Thr Thr Thr Gln
            660                 665                 670

Trp Ala Ile Leu Pro Cys Ser Phe Thr Pro Thr Pro Ala Leu Ser Thr
            675                 680                 685

Gly Leu Ile His Leu His Gln Asn Ile Val Asp Thr Gln Tyr Leu Tyr
            690                 695                 700

Gly Leu Ser Ser Ser Ile Val Ser Trp Ala Val Lys Trp Glu Tyr Ile
705                 710                 715                 720

Val Leu Ala Phe Leu Leu Leu Ala Asp Ala Arg Ile Cys Thr Cys Leu
            725                 730                 735

Trp Ile Met Leu Leu Val Cys Gln Ala Glu Ala Ala Leu Glu Asn Val
            740                 745                 750

Ile Val Leu Asn Ala Ala Ala Ala Gly Thr His Gly Phe Phe Trp
            755                 760                 765

Gly Leu Leu Val Ile Cys Phe Ala Trp His Phe Lys Gly Arg Leu Val
            770                 775                 780

Pro Gly Ala Thr Tyr Leu Cys Leu Gly Ile Trp Pro Leu Leu Leu Leu
785                 790                 795                 800

Leu Phe Leu Leu Pro Gln Arg Ala Leu Ala Leu Asp Ser Ser Asp Gly
            805                 810                 815

Gly Thr Val Gly Cys Leu Val Leu Thr Ile Leu Thr Ile Phe Thr Leu
            820                 825                 830

Thr Pro Gly Tyr Lys Lys Met Val Val Leu Val Ile Trp Trp Leu Gln
```

-continued

```
                835                 840                 845
Tyr Phe Ile Ala Arg Val Glu Ala Phe Ile His Val Trp Val Pro Pro
850                 855                 860

Leu Gln Val Arg Gly Gly Arg Asp Ala Ile Ile Met Leu Thr Cys Leu
865                 870                 875                 880

Phe His Pro Ala Leu Gly Phe Glu Val Thr Lys Ile Leu Leu Gly Ile
                885                 890                 895

Leu Gly Pro Leu Tyr Leu Leu Gln Tyr Ser Leu Ile Lys Leu Pro Tyr
                900                 905                 910

Phe Ile Arg Ala Arg Ala Leu Leu Arg Ala Cys Leu Leu Ala Lys His
                915                 920                 925

Leu Ala Cys Gly Arg Tyr Val Gln Ala Ala Leu Leu His Leu Gly Arg
    930                 935                 940

Leu Thr Gly Thr Tyr Ile Tyr Asp His Leu Ala Pro Met Lys Asp Trp
945                 950                 955                 960

Ala Ala Ser Gly Leu Arg Asp Leu Ala Val Ala Thr Glu Pro Ile Ile
                965                 970                 975

Phe Ser Pro Met Glu Thr Lys Val Ile Thr Trp Gly Ala Asp Thr Ala
                980                 985                 990

Ala Cys Gly Asp Ile Leu Ala Gly  Leu Pro Val Ser Ala  Arg Arg Gly
                995                 1000                1005

His Glu  Ile Phe Leu Gly Pro  Ala Asp Asp Ile Arg  Glu Gly Gly
1010                1015                1020

Trp Arg  Leu Leu Ala Pro Ile  Thr Ala Tyr Ala Gln  Gln Thr Arg
1025                1030                1035

Gly Leu  Leu Gly Ala Ile Val  Val Ser Met Thr Gly  Arg Asp Arg
1040                1045                1050

Thr Glu  Gln Ala Gly Glu Val  Gln Ile Leu Ser Thr  Val Ser Gln
1055                1060                1065

Ser Phe  Leu Gly Thr Thr Ile  Ser Gly Val Leu Trp  Thr Val Tyr
1070                1075                1080

His Gly  Ala Gly Asn Lys Thr  Leu Ala Gly Leu Arg  Gly Pro Val
1085                1090                1095

Thr Gln  Met Tyr Ser Ser Ala  Glu Gly Asp Leu Val  Gly Trp Pro
1100                1105                1110

Ser Pro  Pro Gly Thr Lys Ser  Leu Glu Pro Cys Lys  Cys Gly Ala
1115                1120                1125

Val Asp  Leu Tyr Leu Val Thr  Arg Asn Ala Asp Val  Ile Pro Ala
1130                1135                1140

Arg Arg  Arg Gly Asp Lys Arg  Gly Ala Leu Leu Ser  Pro Arg Pro
1145                1150                1155

Ile Ser  Thr Leu Lys Gly Ser  Ser Gly Gly Pro Val  Leu Cys Pro
1160                1165                1170

Arg Gly  His Val Val Gly Leu  Phe Arg Ala Ala Val  Cys Ser Arg
1175                1180                1185

Gly Val  Ala Lys Ser Ile Asp  Phe Ile Pro Val Glu  Thr Leu Asp
1190                1195                1200

Val Val  Thr Arg Ser Pro Thr  Phe Ser Asp Asn Ser  Thr Pro Pro
1205                1210                1215

Ala Val  Pro Gln Thr Tyr Gln  Val Gly Tyr Leu His  Ala Pro Thr
1220                1225                1230

Gly Ser  Gly Lys Ser Thr Lys  Val Pro Val Ala Tyr  Ala Ala Gln
1235                1240                1245
```

```
Gly Tyr Lys Val Leu Val Leu Asn Pro Ser Val Ala Ala Thr Leu
1250                1255                1260

Gly Phe Gly Ala Tyr Leu Ser Lys Ala His Gly Ile Asn Pro Asn
1265                1270                1275

Ile Arg Thr Gly Val Arg Thr Val Met Thr Gly Glu Ala Ile Thr
1280                1285                1290

Tyr Ser Thr Tyr Gly Lys Phe Leu Ala Asp Gly Gly Cys Ala Ser
1295                1300                1305

Gly Ala Tyr Asp Ile Ile Ile Cys Asp Glu Cys His Ala Val Asp
1310                1315                1320

Ala Thr Ser Ile Leu Gly Ile Gly Thr Val Leu Asp Gln Ala Glu
1325                1330                1335

Thr Ala Gly Val Arg Leu Thr Val Leu Ala Thr Ala Thr Pro Pro
1340                1345                1350

Gly Ser Val Thr Thr Pro His Pro Asp Ile Glu Glu Val Gly Leu
1355                1360                1365

Gly Arg Glu Gly Glu Ile Pro Phe Tyr Gly Arg Ala Ile Pro Leu
1370                1375                1380

Ser Cys Ile Lys Gly Gly Arg His Leu Ile Phe Cys His Ser Lys
1385                1390                1395

Lys Lys Cys Asp Glu Leu Ala Ala Ala Leu Arg Gly Met Gly Leu
1400                1405                1410

Asn Ala Val Ala Tyr Tyr Arg Gly Leu Asp Val Ser Ile Ile Pro
1415                1420                1425

Ala Gln Gly Asp Val Val Val Val Ala Thr Asp Ala Leu Met Thr
1430                1435                1440

Gly Tyr Thr Gly Asp Phe Asp Ser Val Ile Asp Cys Asn Val Ala
1445                1450                1455

Val Thr Gln Ala Val Asp Phe Ser Leu Asp Pro Thr Phe Thr Ile
1460                1465                1470

Thr Thr Gln Thr Val Pro Gln Asp Ala Val Ser Arg Ser Gln Arg
1475                1480                1485

Arg Gly Arg Thr Gly Arg Gly Arg Gln Gly Thr Tyr Arg Tyr Val
1490                1495                1500

Ser Thr Gly Glu Arg Ala Ser Gly Met Phe Asp Ser Val Val Leu
1505                1510                1515

Cys Glu Cys Tyr Asp Ala Gly Ala Ala Trp Tyr Asp Leu Thr Pro
1520                1525                1530

Ala Glu Thr Thr Val Arg Leu Arg Ala Tyr Phe Asn Thr Pro Gly
1535                1540                1545

Leu Pro Val Cys Gln Asp His Leu Glu Phe Trp Glu Ala Val Phe
1550                1555                1560

Thr Gly Leu Thr His Ile Asp Ala His Phe Leu Ser Gln Thr Lys
1565                1570                1575

Gln Ala Gly Glu Asn Phe Ala Tyr Leu Val Ala Tyr Gln Ala Thr
1580                1585                1590

Val Cys Ala Arg Ala Lys Ala Pro Pro Pro Ser Trp Asp Ala Met
1595                1600                1605

Trp Lys Cys Leu Ala Arg Leu Lys Pro Thr Leu Ala Gly Pro Thr
1610                1615                1620

Pro Leu Leu Tyr Arg Leu Gly Pro Ile Thr Asn Glu Val Thr Leu
1625                1630                1635

Thr His Pro Gly Thr Lys Tyr Ile Ala Thr Cys Met Gln Ala Asp
1640                1645                1650
```

```
Leu Glu Val Met Thr Ser Thr Trp Val Leu Ala Gly Gly Val Leu
    1655                1660                1665

Ala Ala Val Ala Ala Tyr Cys Leu Ala Thr Gly Cys Val Ser Ile
    1670                1675                1680

Ile Gly Arg Leu His Val Asn Gln Arg Val Val Val Ala Pro Asp
    1685                1690                1695

Lys Glu Val Leu Tyr Glu Ala Phe Asp Glu Met Glu Glu Cys Ala
    1700                1705                1710

Ser Arg Ala Ala Leu Ile Glu Glu Gly Gln Arg Ile Ala Glu Met
    1715                1720                1725

Leu Lys Ser Lys Ile Gln Gly Leu Leu Gln Gln Ala Ser Lys Gln
    1730                1735                1740

Ala Gln Asp Ile Gln Pro Ala Met Gln Ala Ser Trp Pro Lys Val
    1745                1750                1755

Glu Gln Phe Trp Ala Arg His Met Trp Asn Phe Ile Ser Gly Ile
    1760                1765                1770

Gln Tyr Leu Ala Gly Leu Ser Thr Leu Pro Gly Asn Pro Ala Val
    1775                1780                1785

Ala Ser Met Met Ala Phe Ser Ala Ala Leu Thr Ser Pro Leu Ser
    1790                1795                1800

Thr Ser Thr Thr Ile Leu Leu Asn Ile Met Gly Gly Trp Leu Ala
    1805                1810                1815

Ser Gln Ile Ala Pro Pro Ala Gly Ala Thr Gly Phe Val Val Ser
    1820                1825                1830

Gly Leu Val Gly Ala Ala Val Gly Ser Ile Gly Leu Gly Lys Val
    1835                1840                1845

Leu Val Asp Ile Leu Ala Gly Tyr Gly Ala Gly Ile Ser Gly Ala
    1850                1855                1860

Leu Val Ala Phe Lys Ile Met Ser Gly Glu Lys Pro Ser Met Glu
    1865                1870                1875

Asp Val Ile Asn Leu Leu Pro Gly Ile Leu Ser Pro Gly Ala Leu
    1880                1885                1890

Val Val Gly Val Ile Cys Ala Ala Ile Leu Arg Arg His Val Gly
    1895                1900                1905

Pro Gly Glu Gly Ala Val Gln Trp Met Asn Arg Leu Ile Ala Phe
    1910                1915                1920

Ala Ser Arg Gly Asn His Val Ala Pro Thr His Tyr Val Thr Glu
    1925                1930                1935

Ser Asp Ala Ser Gln Arg Val Thr Gln Leu Leu Gly Ser Leu Thr
    1940                1945                1950

Ile Thr Ser Leu Leu Arg Arg Leu His Asn Trp Ile Thr Glu Asp
    1955                1960                1965

Cys Pro Ile Pro Cys Ser Gly Ser Trp Leu Arg Asp Val Trp Asp
    1970                1975                1980

Trp Val Cys Thr Ile Leu Thr Asp Phe Lys Asn Trp Leu Thr Ser
    1985                1990                1995

Lys Leu Phe Pro Lys Leu Pro Gly Leu Pro Phe Ile Ser Cys Gln
    2000                2005                2010

Lys Gly Tyr Lys Gly Val Trp Ala Gly Thr Gly Ile Met Thr Thr
    2015                2020                2025

Arg Cys Pro Cys Gly Ala Asn Ile Ser Gly Asn Val Arg Leu Gly
    2030                2035                2040

Ser Met Arg Ile Thr Gly Pro Lys Thr Cys Met Asn Thr Trp Gln
```

-continued

```
                2045                2050                2055

Gly Thr Phe Pro Ile Asn Cys Tyr Thr Glu Gly Gln Cys Ala Pro
        2060                2065                2070

Lys Pro Pro Thr Asn Tyr Lys Thr Ala Ile Trp Arg Val Ala Ala
        2075                2080                2085

Ser Glu Tyr Ala Glu Val Thr Gln His Gly Ser Tyr Ser Tyr Val
        2090                2095                2100

Thr Gly Leu Thr Thr Asp Asn Leu Lys Ile Pro Cys Gln Leu Pro
        2105                2110                2115

Ser Pro Glu Phe Phe Ser Trp Val Asp Gly Val Gln Ile His Arg
        2120                2125                2130

Phe Ala Pro Thr Pro Lys Pro Phe Phe Arg Asp Glu Val Ser Phe
        2135                2140                2145

Cys Val Gly Leu Asn Ser Tyr Ala Val Gly Ser Gln Leu Pro Cys
        2150                2155                2160

Glu Pro Glu Pro Asp Ala Asp Val Leu Arg Ser Met Leu Thr Asp
        2165                2170                2175

Pro Pro His Ile Thr Ala Glu Thr Ala Ala Arg Arg Leu Ala Arg
        2180                2185                2190

Gly Ser Pro Pro Ser Glu Ala Ser Ser Ser Val Ser Gln Leu Ser
        2195                2200                2205

Ala Pro Ser Leu Arg Ala Thr Cys Thr Thr His Ser Asn Thr Tyr
        2210                2215                2220

Asp Val Asp Met Val Asp Ala Asn Leu Leu Met Glu Gly Gly Val
        2225                2230                2235

Ala Gln Thr Glu Pro Glu Ser Arg Val Pro Val Leu Asp Phe Leu
        2240                2245                2250

Glu Pro Met Ala Glu Glu Ser Asp Leu Glu Pro Ser Ile Pro
        2255                2260                2265

Ser Glu Cys Met Leu Pro Arg Ser Gly Phe Pro Arg Ala Leu Pro
        2270                2275                2280

Ala Trp Ala Arg Pro Asp Tyr Asn Pro Pro Leu Val Glu Ser Trp
        2285                2290                2295

Arg Arg Pro Asp Tyr Gln Pro Pro Thr Val Ala Gly Cys Ala Leu
        2300                2305                2310

Pro Pro Pro Lys Lys Ala Pro Thr Pro Pro Pro Arg Arg Arg Arg
        2315                2320                2325

Thr Val Gly Leu Ser Glu Ser Thr Ile Ser Glu Ala Leu Gln Gln
        2330                2335                2340

Leu Ala Ile Lys Thr Phe Gly Gln Pro Pro Ser Ser Gly Asp Ala
        2345                2350                2355

Gly Ser Ser Thr Gly Ala Gly Ala Ala Glu Ser Gly Gly Pro Thr
        2360                2365                2370

Ser Pro Gly Glu Pro Ala Pro Ser Glu Thr Gly Ser Ala Ser Ser
        2375                2380                2385

Met Pro Pro Leu Glu Gly Glu Pro Gly Asp Pro Asp Leu Glu Ser
        2390                2395                2400

Asp Gln Val Glu Leu Gln Pro Pro Pro Gln Gly Gly Gly Val Ala
        2405                2410                2415

Pro Gly Ser Gly Ser Gly Ser Trp Ser Thr Cys Ser Glu Glu Asp
        2420                2425                2430

Asp Thr Thr Val Cys Cys Ser Met Ser Tyr Ser Trp Thr Gly Ala
        2435                2440                2445
```

-continued

| | | | | | | | | | | |
|---|---|---|---|---|---|---|---|---|---|---|
| Leu | Ile | Thr | Pro | Cys | Ser | Pro | Glu | Glu | Lys | Leu | Pro | Ile | Asn |
| 2450 | | | | 2455 | | | | | 2460 | | | |
| Pro | Leu | Ser | Asn | Ser | Leu | Leu | Arg | Tyr | His | Asn | Lys | Val | Tyr | Cys |
| 2465 | | | | | 2470 | | | | | 2475 | | | | |
| Thr | Thr | Ser | Lys | Ser | Ala | Ser | Gln | Arg | Ala | Lys | Lys | Val | Thr | Phe |
| 2480 | | | | | 2485 | | | | | 2490 | | | | |
| Asp | Arg | Thr | Gln | Val | Leu | Asp | Ala | His | Tyr | Asp | Ser | Val | Leu | Lys |
| 2495 | | | | | 2500 | | | | | 2505 | | | | |
| Asp | Ile | Lys | Leu | Ala | Ala | Ser | Lys | Val | Ser | Ala | Arg | Leu | Leu | Thr |
| 2510 | | | | | 2515 | | | | | 2520 | | | | |
| Leu | Glu | Glu | Ala | Cys | Gln | Leu | Thr | Pro | Pro | His | Ser | Ala | Arg | Ser |
| 2525 | | | | | 2530 | | | | | 2535 | | | | |
| Lys | Tyr | Gly | Phe | Gly | Ala | Lys | Glu | Val | Arg | Ser | Leu | Ser | Gly | Arg |
| 2540 | | | | | 2545 | | | | | 2550 | | | | |
| Ala | Val | Asn | His | Ile | Lys | Ser | Val | Trp | Lys | Asp | Leu | Leu | Glu | Asp |
| 2555 | | | | | 2560 | | | | | 2565 | | | | |
| Pro | Gln | Thr | Pro | Ile | Pro | Thr | Thr | Ile | Met | Ala | Lys | Asn | Glu | Val |
| 2570 | | | | | 2575 | | | | | 2580 | | | | |
| Phe | Cys | Val | Asp | Pro | Ala | Lys | Gly | Gly | Lys | Lys | Pro | Ala | Arg | Leu |
| 2585 | | | | | 2590 | | | | | 2595 | | | | |
| Ile | Val | Tyr | Pro | Asp | Leu | Gly | Val | Arg | Val | Cys | Glu | Lys | Met | Ala |
| 2600 | | | | | 2605 | | | | | 2610 | | | | |
| Leu | Tyr | Asp | Ile | Thr | Gln | Lys | Leu | Pro | Gln | Ala | Val | Met | Gly | Ala |
| 2615 | | | | | 2620 | | | | | 2625 | | | | |
| Ser | Tyr | Gly | Phe | Gln | Tyr | Ser | Pro | Ala | Gln | Arg | Val | Glu | Tyr | Leu |
| 2630 | | | | | 2635 | | | | | 2640 | | | | |
| Leu | Lys | Ala | Trp | Ala | Glu | Lys | Lys | Asp | Pro | Met | Gly | Phe | Ser | Tyr |
| 2645 | | | | | 2650 | | | | | 2655 | | | | |
| Asp | Thr | Arg | Cys | Phe | Asp | Ser | Thr | Val | Thr | Glu | Arg | Asp | Ile | Arg |
| 2660 | | | | | 2665 | | | | | 2670 | | | | |
| Thr | Glu | Glu | Ser | Ile | Tyr | Gln | Ala | Cys | Ser | Leu | Pro | Glu | Glu | Ala |
| 2675 | | | | | 2680 | | | | | 2685 | | | | |
| Arg | Thr | Ala | Ile | His | Ser | Leu | Thr | Glu | Arg | Leu | Tyr | Val | Gly | Gly |
| 2690 | | | | | 2695 | | | | | 2700 | | | | |
| Pro | Met | Phe | Asn | Ser | Lys | Gly | Gln | Thr | Cys | Gly | Tyr | Arg | Arg | Cys |
| 2705 | | | | | 2710 | | | | | 2715 | | | | |
| Arg | Ala | Ser | Gly | Val | Leu | Thr | Thr | Ser | Met | Gly | Asn | Thr | Ile | Thr |
| 2720 | | | | | 2725 | | | | | 2730 | | | | |
| Cys | Tyr | Val | Lys | Ala | Leu | Ala | Ala | Cys | Lys | Ala | Ala | Gly | Ile | Val |
| 2735 | | | | | 2740 | | | | | 2745 | | | | |
| Ala | Pro | Thr | Met | Leu | Val | Cys | Gly | Asp | Asp | Leu | Val | Val | Ile | Ser |
| 2750 | | | | | 2755 | | | | | 2760 | | | | |
| Glu | Ser | Gln | Gly | Thr | Glu | Glu | Asp | Glu | Arg | Asn | Leu | Arg | Ala | Phe |
| 2765 | | | | | 2770 | | | | | 2775 | | | | |
| Thr | Glu | Ala | Met | Thr | Arg | Tyr | Ser | Ala | Pro | Pro | Gly | Asp | Pro | Pro |
| 2780 | | | | | 2785 | | | | | 2790 | | | | |
| Arg | Pro | Glu | Tyr | Asp | Leu | Glu | Leu | Ile | Thr | Ser | Cys | Ser | Ser | Asn |
| 2795 | | | | | 2800 | | | | | 2805 | | | | |
| Val | Ser | Val | Ala | Leu | Gly | Pro | Arg | Gly | Arg | Arg | Arg | Tyr | Tyr | Leu |
| 2810 | | | | | 2815 | | | | | 2820 | | | | |
| Thr | Arg | Asp | Pro | Thr | Thr | Pro | Leu | Ala | Arg | Ala | Ala | Trp | Glu | Thr |
| 2825 | | | | | 2830 | | | | | 2835 | | | | |
| Val | Arg | His | Ser | Pro | Ile | Asn | Ser | Trp | Leu | Gly | Asn | Ile | Ile | Gln |
| 2840 | | | | | 2845 | | | | | 2850 | | | | |

Tyr Ala Pro Thr Ile Trp Val Arg Met Val Leu Met Thr His Phe
2855                2860                2865

Phe Ser Ile Leu Met Val Gln Asp Thr Leu Asp Gln Asn Leu Asn
2870                2875                2880

Phe Glu Met Tyr Gly Ser Val Tyr Ser Val Asn Pro Leu Asp Leu
2885                2890                2895

Pro Ala Ile Ile Glu Arg Leu His Gly Leu Asp Ala Phe Ser Met
2900                2905                2910

His Thr Tyr Ser His His Glu Leu Thr Arg Val Ala Ser Ala Leu
2915                2920                2925

Arg Lys Leu Gly Ala Pro Pro Leu Arg Val Trp Lys Ser Arg Ala
2930                2935                2940

Arg Ala Val Arg Ala Ser Leu Ile Ser Arg Gly Gly Lys Ala Ala
2945                2950                2955

Val Cys Gly Arg Tyr Leu Phe Asn Trp Ala Val Lys Thr Lys Leu
2960                2965                2970

Lys Leu Thr Pro Leu Pro Glu Ala Arg Leu Leu Asp Leu Ser Ser
2975                2980                2985

Trp Phe Thr Val Gly Ala Gly Gly Gly Asp Ile Phe His Ser Val
2990                2995                3000

Ser Arg Ala Arg Pro Arg Ser Leu Leu Phe Gly Leu Leu Leu Leu
3005                3010                3015

Phe Val Gly Val Gly Leu Phe Leu Leu Pro Ala Arg
3020                3025                3030

<210> SEQ ID NO 58
<211> LENGTH: 3030
<212> TYPE: PRT
<213> ORGANISM: Hepatitis C virus

<400> SEQUENCE: 58

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ser Ala Val
            180                 185                 190

```
Pro Tyr Arg Asn Ala Ser Gly Val Tyr His Val Thr Asn Asp Cys Pro
        195                 200                 205

Asn Ser Ser Ile Val Tyr Glu Ala Glu Asp Leu Ile Leu His Ala Pro
        210                 215                 220

Gly Cys Val Pro Cys Val Arg Gln Gly Asn Val Ser Arg Cys Trp Val
225                 230                 235                 240

Gln Ile Thr Pro Thr Leu Ser Ala Pro Ser Leu Gly Ala Val Thr Ala
            245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Val Phe Leu Val Gly
        275                 280                 285

Gln Met Phe Thr Tyr Ser Pro Arg Arg His Asn Val Val Gln Asp Cys
290                 295                 300

Asn Cys Ser Ile Tyr Ser Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Val Val Asp Ile Ile Ala Gly Ala His
            340                 345                 350

Trp Gly Val Leu Phe Ala Ala Ala Tyr Tyr Ala Ser Ala Ala Asn Trp
        355                 360                 365

Ala Lys Val Val Leu Val Leu Phe Leu Phe Ala Gly Val Asp Ala Ser
        370                 375                 380

Thr Arg Thr Val Gly Gly Ser Ala Ala Gln Gly Ala Arg Gly Leu Ala
385                 390                 395                 400

Ser Leu Phe Thr Pro Gly Pro Gln Gln Asn Leu Gln Leu Ile Asn Thr
            405                 410                 415

Asn Gly Ser Trp His Ile Asn Arg Thr Ala Leu Asn Cys Asn Asp Ser
            420                 425                 430

Leu Gln Thr Gly Phe Val Ala Gly Leu Leu Tyr Tyr His Lys Phe Asn
        435                 440                 445

Ser Thr Gly Cys Pro Gln Arg Met Ala Ser Cys Arg Pro Leu Ala Ala
        450                 455                 460

Phe Asp Gln Gly Trp Gly Thr Ile Ser Tyr Ala Ala Val Ser Gly Pro
465                 470                 475                 480

Ser Asp Asp Lys Pro Tyr Cys Trp His Tyr Pro Pro Arg Pro Cys Gly
            485                 490                 495

Ile Val Pro Ala Arg Gly Val Cys Gly Pro Val Tyr Cys Phe Thr Pro
            500                 505                 510

Ser Pro Val Val Val Gly Thr Thr Asp Arg Lys Gly Asn Pro Thr Tyr
        515                 520                 525

Ser Trp Gly Glu Asn Glu Thr Asp Ile Phe Leu Leu Asn Asn Thr Arg
530                 535                 540

Pro Pro Thr Gly Asn Trp Phe Gly Cys Thr Trp Met Asn Ser Thr Gly
545                 550                 555                 560

Phe Val Lys Thr Cys Gly Ala Pro Pro Cys Asn Leu Gly Pro Thr Gly
            565                 570                 575

Asn Asn Ser Leu Lys Cys Pro Thr Asp Cys Phe Arg Lys His Pro Asp
            580                 585                 590

Ala Thr Tyr Thr Lys Cys Gly Ser Gly Pro Trp Leu Thr Pro Arg Cys
        595                 600                 605

Leu Val His Tyr Pro Tyr Arg Leu Trp His Tyr Pro Cys Thr Leu Asn
```

-continued

```
            610                 615                 620
Tyr Thr Ile Phe Lys Val Arg Met Tyr Ile Gly Gly Leu Glu His Arg
625                 630                 635                 640

Leu Glu Val Ala Cys Asn Trp Thr Arg Gly Glu Arg Cys Asp Leu Glu
                    645                 650                 655

Asp Arg Asp Arg Ala Glu Leu Ser Pro Leu His Thr Thr Thr Gln
                660                 665                 670

Trp Ala Ile Leu Pro Cys Ser Phe Thr Pro Thr Pro Ala Leu Ser Thr
                675                 680                 685

Gly Leu Ile His Leu His Gln Asn Ile Val Asp Thr Gln Tyr Leu Tyr
690                 695                 700

Gly Leu Ser Ser Ser Ile Val Ser Trp Ala Val Lys Trp Glu Tyr Ile
705                 710                 715                 720

Val Leu Ala Phe Leu Leu Ala Asp Ala Arg Ile Cys Thr Cys Leu
                725                 730                 735

Trp Ile Met Leu Leu Val Cys Gln Ala Glu Ala Ala Leu Glu Asn Val
                740                 745                 750

Ile Val Leu Asn Ala Ala Ala Ala Gly Thr His Gly Phe Phe Trp
755                 760                 765

Gly Leu Leu Val Ile Cys Phe Ala Trp His Phe Lys Gly Arg Leu Val
770                 775                 780

Pro Gly Ala Thr Tyr Leu Cys Leu Gly Ile Trp Pro Leu Leu Leu Leu
785                 790                 795                 800

Leu Phe Leu Leu Pro Gln Arg Ala Leu Ala Leu Asp Ser Ser Asp Gly
                805                 810                 815

Gly Thr Val Gly Cys Leu Val Leu Thr Ile Leu Thr Ile Phe Thr Leu
                820                 825                 830

Thr Pro Gly Tyr Lys Lys Met Val Val Leu Val Ile Trp Trp Leu Gln
                835                 840                 845

Tyr Phe Ile Ala Arg Val Glu Ala Phe Ile His Val Trp Val Pro Pro
850                 855                 860

Leu Gln Val Arg Gly Gly Arg Asp Ala Ile Ile Met Leu Thr Cys Leu
865                 870                 875                 880

Phe His Pro Ala Leu Gly Phe Glu Val Thr Lys Ile Leu Leu Gly Ile
                885                 890                 895

Leu Gly Pro Leu Tyr Leu Leu Gln Tyr Ser Leu Ile Lys Leu Pro Tyr
                900                 905                 910

Phe Ile Arg Ala Arg Ala Leu Leu Arg Ala Cys Leu Leu Ala Lys His
                915                 920                 925

Leu Ala Cys Gly Arg Tyr Val Gln Ala Ala Leu Leu His Leu Gly Arg
930                 935                 940

Leu Thr Gly Thr Tyr Ile Tyr Asp His Leu Ala Pro Met Lys Asp Trp
945                 950                 955                 960

Ala Ala Ser Gly Leu Arg Asp Leu Ala Val Ala Thr Glu Pro Ile Ile
                965                 970                 975

Phe Ser Pro Met Glu Thr Lys Val Ile Thr Trp Gly Ala Asp Thr Ala
                980                 985                 990

Ala Cys Gly Asp Ile Leu Ala Gly  Leu Pro Val Ser Ala  Arg Arg Gly
            995                 1000                1005

His Glu  Ile Phe Leu Gly Pro  Ala Asp Asp Ile Arg  Glu Gly Gly
        1010                1015                1020

Trp Arg Leu Leu Ala Pro Ile  Thr Ala Tyr Ala Gln  Gln Thr Arg
            1025                1030                1035
```

```
Gly Leu Leu Gly Ala Ile Val Val Ser Met Thr Gly Arg Asp Arg
    1040                1045                1050

Thr Glu Gln Ala Gly Glu Val Gln Ile Leu Ser Thr Val Ser Gln
    1055                1060                1065

Ser Phe Leu Gly Thr Thr Ile Ser Gly Val Leu Trp Thr Val Tyr
    1070                1075                1080

His Gly Ala Gly Asn Lys Thr Leu Ala Gly Leu Arg Gly Pro Val
    1085                1090                1095

Thr Gln Met Tyr Ser Ser Ala Glu Gly Asp Leu Val Gly Trp Pro
    1100                1105                1110

Ser Pro Pro Gly Thr Arg Ser Leu Glu Pro Cys Lys Cys Gly Ala
    1115                1120                1125

Val Asp Leu Tyr Leu Val Thr Arg Asn Ala Asp Val Ile Pro Ala
    1130                1135                1140

Arg Arg Arg Gly Asp Lys Arg Gly Ala Leu Leu Ser Pro Arg Pro
    1145                1150                1155

Ile Ser Thr Leu Lys Gly Ser Ser Gly Gly Pro Val Leu Cys Pro
    1160                1165                1170

Arg Gly His Val Val Gly Leu Phe Arg Ala Ala Val Cys Ser Arg
    1175                1180                1185

Gly Val Ala Lys Ser Ile Asp Phe Ile Pro Val Glu Thr Leu Asp
    1190                1195                1200

Val Val Thr Arg Ser Pro Thr Phe Ser Asp Asn Ser Thr Pro Pro
    1205                1210                1215

Ala Val Pro Gln Thr Tyr Gln Val Gly Tyr Leu His Ala Pro Thr
    1220                1225                1230

Gly Ser Gly Lys Ser Thr Lys Val Pro Val Ala Tyr Ala Ala Gln
    1235                1240                1245

Gly Tyr Lys Val Leu Val Leu Asn Pro Ser Val Ala Ala Thr Leu
    1250                1255                1260

Gly Phe Gly Ala Tyr Leu Ser Lys Ala His Gly Ile Asn Pro Asn
    1265                1270                1275

Ile Arg Thr Gly Val Arg Thr Val Met Thr Gly Glu Ala Ile Thr
    1280                1285                1290

Tyr Ser Thr Tyr Gly Lys Phe Leu Ala Asp Gly Gly Cys Ala Ser
    1295                1300                1305

Gly Ala Tyr Asp Ile Ile Ile Cys Asp Glu Cys His Ala Val Asp
    1310                1315                1320

Ala Thr Ser Ile Leu Gly Ile Gly Thr Val Leu Asp Gln Ala Glu
    1325                1330                1335

Thr Ala Gly Val Arg Leu Thr Val Leu Ala Thr Ala Thr Pro Pro
    1340                1345                1350

Gly Ser Val Thr Thr Pro His Pro Asp Ile Glu Glu Val Gly Leu
    1355                1360                1365

Gly Arg Glu Gly Glu Ile Pro Phe Tyr Gly Arg Ala Ile Pro Leu
    1370                1375                1380

Ser Cys Ile Lys Gly Gly Arg His Leu Ile Phe Cys His Ser Lys
    1385                1390                1395

Lys Lys Cys Asp Glu Leu Ala Ala Ala Leu Arg Gly Met Gly Leu
    1400                1405                1410

Asn Ala Val Ala Tyr Tyr Arg Gly Leu Asp Val Ser Ile Ile Pro
    1415                1420                1425

Ala Gln Gly Asp Val Val Val Val Ala Thr Asp Ala Leu Met Thr
    1430                1435                1440
```

```
Gly Tyr Thr Gly Asp Phe Asp Ser Val Ile Asp Cys Asn Val Ala
    1445                1450                1455

Val Thr Gln Ala Val Asp Phe Ser Leu Asp Pro Thr Phe Thr Ile
    1460                1465                1470

Thr Thr Gln Thr Val Pro Gln Asp Ala Val Ser Arg Ser Gln Arg
    1475                1480                1485

Arg Gly Arg Thr Gly Arg Gly Arg Gln Gly Thr Tyr Arg Tyr Val
    1490                1495                1500

Ser Thr Gly Glu Arg Ala Ser Gly Met Phe Asp Ser Val Val Leu
    1505                1510                1515

Cys Glu Cys Tyr Asp Ala Gly Ala Ala Trp Tyr Asp Leu Thr Pro
    1520                1525                1530

Ala Glu Thr Thr Val Arg Leu Arg Ala Tyr Phe Asn Thr Pro Gly
    1535                1540                1545

Leu Pro Val Cys Gln Asp His Leu Glu Phe Trp Glu Ala Val Phe
    1550                1555                1560

Thr Gly Leu Thr His Ile Asp Ala His Phe Leu Ser Gln Thr Lys
    1565                1570                1575

Gln Ala Gly Glu Asn Phe Ala Tyr Leu Val Ala Tyr Gln Ala Thr
    1580                1585                1590

Val Cys Ala Arg Ala Lys Ala Pro Pro Pro Ser Trp Asp Ala Met
    1595                1600                1605

Trp Lys Cys Leu Ala Arg Leu Lys Pro Thr Leu Ala Gly Pro Thr
    1610                1615                1620

Pro Leu Leu Tyr Arg Leu Gly Pro Ile Thr Asn Glu Val Thr Leu
    1625                1630                1635

Thr His Pro Gly Thr Lys Tyr Ile Ala Thr Cys Met Gln Ala Asp
    1640                1645                1650

Leu Glu Val Met Thr Ser Thr Trp Val Leu Ala Gly Gly Val Leu
    1655                1660                1665

Ala Ala Val Ala Ala Tyr Cys Leu Ala Thr Gly Cys Val Ser Ile
    1670                1675                1680

Ile Gly Arg Leu His Val Asn Gln Arg Val Val Val Ala Pro Asp
    1685                1690                1695

Lys Glu Val Leu Tyr Glu Ala Phe Asp Glu Met Glu Glu Cys Ala
    1700                1705                1710

Ser Arg Ala Ala Leu Ile Glu Glu Gly Gln Arg Ile Ala Glu Met
    1715                1720                1725

Leu Lys Ser Lys Ile Gln Gly Leu Leu Gln Gln Ala Ser Lys Gln
    1730                1735                1740

Ala Gln Asp Ile Gln Pro Ala Met Gln Ala Ser Trp Pro Lys Val
    1745                1750                1755

Glu Gln Phe Trp Ala Arg His Met Trp Asn Phe Ile Ser Gly Ile
    1760                1765                1770

Gln Tyr Leu Ala Gly Leu Ser Thr Leu Pro Gly Asn Pro Ala Val
    1775                1780                1785

Ala Ser Met Met Ala Phe Ser Ala Ala Leu Thr Ser Pro Leu Ser
    1790                1795                1800

Thr Ser Thr Thr Ile Leu Leu Asn Ile Met Gly Gly Trp Leu Ala
    1805                1810                1815

Ser Gln Ile Ala Pro Pro Ala Gly Ala Thr Gly Phe Val Val Ser
    1820                1825                1830

Gly Leu Val Gly Ala Ala Val Gly Ser Ile Gly Leu Gly Lys Val
```

-continued

```
            1835                1840                1845

Leu Val Asp Ile Leu Ala Gly Tyr Gly Ala Gly Ile Ser Gly Ala
    1850                1855                1860

Leu Val Ala Phe Lys Ile Met Ser Gly Glu Lys Pro Ser Met Glu
    1865                1870                1875

Asp Val Ile Asn Leu Leu Pro Gly Ile Leu Ser Pro Gly Ala Leu
    1880                1885                1890

Val Val Gly Val Ile Cys Ala Ala Ile Leu Arg Arg His Val Gly
    1895                1900                1905

Pro Gly Glu Gly Ala Val Gln Trp Met Asn Arg Leu Ile Ala Phe
    1910                1915                1920

Ala Ser Arg Gly Asn His Val Ala Pro Thr His Tyr Val Thr Glu
    1925                1930                1935

Ser Asp Ala Ser Gln Arg Val Thr Gln Leu Leu Gly Ser Leu Thr
    1940                1945                1950

Ile Thr Ser Leu Leu Arg Arg Leu His Asn Trp Ile Thr Glu Asp
    1955                1960                1965

Cys Pro Ile Pro Cys Ser Gly Ser Trp Leu Arg Asp Val Trp Asp
    1970                1975                1980

Trp Val Cys Thr Ile Leu Thr Asp Phe Lys Asn Trp Leu Thr Ser
    1985                1990                1995

Lys Leu Phe Pro Lys Leu Pro Gly Leu Pro Phe Ile Ser Cys Gln
    2000                2005                2010

Lys Gly Tyr Lys Gly Val Trp Ala Gly Thr Gly Ile Met Thr Thr
    2015                2020                2025

Arg Cys Pro Cys Gly Ala Asn Ile Ser Gly Asn Val Arg Leu Gly
    2030                2035                2040

Ser Met Arg Ile Thr Gly Pro Lys Thr Cys Met Asn Thr Trp Gln
    2045                2050                2055

Gly Thr Phe Pro Ile Asn Cys Tyr Thr Glu Gly Gln Cys Ala Pro
    2060                2065                2070

Lys Pro Pro Thr Asn Tyr Lys Thr Ala Ile Trp Arg Val Ala Ala
    2075                2080                2085

Ser Glu Tyr Ala Glu Val Thr Gln His Gly Ser Tyr Ser Tyr Val
    2090                2095                2100

Thr Gly Leu Thr Thr Asp Asn Leu Lys Ile Pro Cys Gln Leu Pro
    2105                2110                2115

Ser Pro Glu Phe Phe Ser Trp Val Asp Gly Val Gln Ile His Arg
    2120                2125                2130

Phe Ala Pro Thr Pro Lys Pro Phe Phe Arg Asp Glu Val Ser Phe
    2135                2140                2145

Cys Val Gly Leu Asn Ser Tyr Ala Val Gly Ser Gln Leu Pro Cys
    2150                2155                2160

Glu Pro Glu Pro Asp Ala Asp Val Leu Arg Ser Met Leu Thr Asp
    2165                2170                2175

Pro Pro His Ile Thr Ala Glu Thr Ala Ala Arg Arg Leu Ala Arg
    2180                2185                2190

Gly Ser Pro Pro Ser Glu Ala Ser Ser Ser Val Ser Gln Leu Ser
    2195                2200                2205

Ala Pro Ser Leu Arg Ala Thr Cys Thr Thr His Ser Asn Thr Tyr
    2210                2215                2220

Asp Val Asp Met Val Asp Ala Asn Leu Leu Met Glu Gly Gly Val
    2225                2230                2235
```

-continued

```
Ala Gln Thr Glu Pro Glu Ser Arg Val Pro Val Leu Asp Phe Leu
2240                2245                2250

Glu Pro Met Ala Glu Glu Glu Ser Asp Leu Glu Pro Ser Ile Pro
2255                2260                2265

Ser Glu Cys Met Leu Pro Arg Ser Gly Phe Pro Arg Ala Leu Pro
2270                2275                2280

Ala Trp Ala Arg Pro Asp Tyr Asn Pro Pro Leu Val Glu Ser Trp
2285                2290                2295

Arg Arg Pro Asp Tyr Gln Pro Pro Thr Val Ala Gly Cys Ala Leu
2300                2305                2310

Pro Pro Pro Lys Lys Ala Pro Thr Pro Pro Pro Arg Arg Arg Arg
2315                2320                2325

Thr Val Gly Leu Ser Glu Ser Thr Ile Ser Glu Ala Leu Gln Gln
2330                2335                2340

Leu Ala Ile Lys Thr Phe Gly Gln Pro Pro Ser Ser Gly Asp Ala
2345                2350                2355

Gly Ser Ser Thr Gly Ala Gly Ala Ala Glu Ser Gly Gly Pro Thr
2360                2365                2370

Ser Pro Gly Glu Pro Ala Pro Ser Glu Thr Gly Ser Ala Ser Ser
2375                2380                2385

Met Pro Pro Leu Glu Gly Glu Pro Gly Asp Pro Asp Leu Glu Ser
2390                2395                2400

Asp Gln Val Glu Leu Gln Pro Pro Gln Gly Gly Gly Val Ala
2405                2410                2415

Pro Gly Ser Gly Ser Gly Ser Trp Ser Thr Cys Ser Glu Glu Asp
2420                2425                2430

Asp Thr Thr Val Cys Cys Ser Met Ser Tyr Ser Trp Thr Gly Ala
2435                2440                2445

Leu Ile Thr Pro Cys Ser Pro Glu Glu Glu Lys Leu Pro Ile Asn
2450                2455                2460

Pro Leu Ser Asn Ser Leu Leu Arg Tyr His Asn Lys Val Tyr Cys
2465                2470                2475

Thr Thr Ser Lys Ser Ala Ser Gln Arg Ala Lys Lys Val Thr Phe
2480                2485                2490

Asp Arg Thr Gln Val Leu Asp Ala His Tyr Asp Ser Val Leu Lys
2495                2500                2505

Asp Ile Lys Leu Ala Ala Ser Lys Val Ser Ala Arg Leu Leu Thr
2510                2515                2520

Leu Glu Glu Ala Cys Gln Leu Thr Pro Pro His Ser Ala Arg Ser
2525                2530                2535

Lys Tyr Gly Phe Gly Ala Lys Glu Val Arg Ser Leu Ser Gly Arg
2540                2545                2550

Ala Val Asn His Ile Lys Ser Val Trp Lys Asp Leu Leu Glu Asp
2555                2560                2565

Pro Gln Thr Pro Ile Pro Thr Thr Ile Met Ala Lys Asn Glu Val
2570                2575                2580

Phe Cys Val Asp Pro Ala Lys Gly Gly Lys Lys Pro Ala Arg Leu
2585                2590                2595

Ile Val Tyr Pro Asp Leu Gly Val Arg Val Cys Glu Lys Met Ala
2600                2605                2610

Leu Tyr Asp Ile Thr Gln Lys Leu Pro Gln Ala Val Met Gly Ala
2615                2620                2625

Ser Tyr Gly Phe Gln Tyr Ser Pro Ala Gln Arg Val Glu Tyr Leu
2630                2635                2640
```

```
Leu Lys Ala Trp Ala Glu Lys Lys Asp Pro Met Gly Phe Ser Tyr
2645                2650                2655

Asp Thr Arg Cys Phe Asp Ser Thr Val Thr Glu Arg Asp Ile Arg
    2660                2665                2670

Thr Glu Glu Ser Ile Tyr Gln Ala Cys Ser Leu Pro Glu Glu Ala
2675                2680                2685

Arg Thr Ala Ile His Ser Leu Thr Glu Arg Leu Tyr Val Gly Gly
    2690                2695                2700

Pro Met Phe Asn Ser Lys Gly Gln Thr Cys Gly Tyr Arg Arg Cys
2705                2710                2715

Arg Ala Ser Gly Val Leu Thr Thr Ser Met Gly Asn Thr Ile Thr
    2720                2725                2730

Cys Tyr Val Lys Ala Leu Ala Ala Cys Lys Ala Ala Gly Ile Val
2735                2740                2745

Ala Pro Thr Met Leu Val Cys Gly Asp Asp Leu Val Val Ile Ser
    2750                2755                2760

Glu Ser Gln Gly Thr Glu Glu Asp Glu Arg Asn Leu Arg Ala Phe
2765                2770                2775

Thr Glu Ala Met Thr Arg Tyr Ser Ala Pro Pro Gly Asp Pro Pro
    2780                2785                2790

Arg Pro Glu Tyr Asp Leu Glu Leu Ile Thr Ser Cys Ser Ser Asn
2795                2800                2805

Val Ser Val Ala Leu Gly Pro Arg Gly Arg Arg Arg Tyr Tyr Leu
    2810                2815                2820

Thr Arg Asp Pro Thr Thr Pro Leu Ala Arg Ala Ala Trp Glu Thr
2825                2830                2835

Val Arg His Ser Pro Ile Asn Ser Trp Leu Gly Asn Ile Ile Gln
    2840                2845                2850

Tyr Ala Pro Thr Ile Trp Val Arg Met Val Leu Met Thr His Phe
2855                2860                2865

Phe Ser Ile Leu Met Val Gln Asp Thr Leu Asp Gln Asn Leu Asn
    2870                2875                2880

Phe Glu Met Tyr Gly Ser Val Tyr Ser Val Asn Pro Leu Asp Leu
2885                2890                2895

Pro Ala Ile Ile Glu Arg Leu His Gly Leu Asp Ala Phe Ser Met
    2900                2905                2910

His Thr Tyr Ser His His Glu Leu Thr Arg Val Ala Ser Ala Leu
2915                2920                2925

Arg Lys Leu Gly Ala Pro Pro Leu Arg Val Trp Lys Ser Arg Ala
    2930                2935                2940

Arg Ala Val Arg Ala Ser Leu Ile Ser Arg Gly Gly Lys Ala Ala
2945                2950                2955

Val Cys Gly Arg Tyr Leu Phe Asn Trp Ala Val Lys Thr Lys Leu
    2960                2965                2970

Lys Leu Thr Pro Leu Pro Glu Ala Arg Leu Leu Asp Leu Ser Ser
2975                2980                2985

Trp Phe Thr Val Gly Ala Gly Gly Gly Asp Ile Phe His Ser Val
    2990                2995                3000

Ser Arg Ala Arg Pro Arg Ser Leu Leu Phe Gly Leu Leu Leu Leu
3005                3010                3015

Phe Val Gly Val Gly Leu Phe Leu Leu Pro Ala Arg
3020                3025                3030
```

```
<210> SEQ ID NO 59
<211> LENGTH: 3030
<212> TYPE: PRT
<213> ORGANISM: Hepatitis C virus

<400> SEQUENCE: 59

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Thr Ser Ala Val
            180                 185                 190

Pro Tyr Arg Asn Ala Ser Gly Val Tyr His Val Thr Asn Asp Cys Pro
        195                 200                 205

Asn Ser Ser Ile Val Tyr Glu Ala Glu Asp Leu Ile Leu His Ala Pro
210                 215                 220

Gly Cys Val Pro Cys Val Arg Gln Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Val Phe Leu Val Gly
        275                 280                 285

Gln Met Phe Thr Tyr Ser Pro Arg Arg His Asn Val Val Gln Asp Cys
290                 295                 300

Asn Cys Ser Ile Tyr Ser Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Val Val Ile Asp Ile Ile Ala Gly Ala His
            340                 345                 350

Trp Gly Val Leu Phe Ala Ala Tyr Tyr Ala Ser Ala Ala Asn Trp
        355                 360                 365

Ala Lys Val Val Leu Val Leu Phe Leu Phe Ala Gly Val Asp Ala Ser
370                 375                 380

Thr Arg Thr Val Gly Gly Ser Ala Ala Gln Gly Ala Arg Gly Leu Ala
```

-continued

```
            385                 390                 395                 400
Ser Leu Phe Thr Pro Gly Pro Gln Gln Asn Leu Gln Leu Ile Asn Thr
                    405                 410                 415

Asn Gly Ser Trp His Ile Asn Arg Thr Ala Leu Asn Cys Asn Asp Ser
                420                 425                 430

Leu Gln Thr Gly Phe Val Ala Gly Leu Leu Tyr Tyr His Lys Phe Asn
            435                 440                 445

Ser Thr Gly Cys Pro Gln Arg Met Ala Ser Cys Arg Pro Leu Ala Ala
        450                 455                 460

Phe Asp Gln Gly Trp Gly Thr Ile Ser Tyr Ala Ala Val Ser Gly Pro
465                 470                 475                 480

Ser Asp Asp Lys Pro Tyr Cys Trp His Tyr Pro Arg Pro Cys Gly
                485                 490                 495

Ile Val Pro Ala Arg Gly Val Cys Gly Pro Val Tyr Cys Phe Thr Pro
                500                 505                 510

Ser Pro Val Val Val Gly Thr Thr Asp Arg Lys Gly Asn Pro Thr Tyr
            515                 520                 525

Ser Trp Gly Glu Asn Glu Thr Asp Ile Phe Leu Leu Asn Asn Thr Arg
        530                 535                 540

Pro Pro Thr Gly Asn Trp Phe Gly Cys Thr Trp Met Asn Ser Thr Gly
545                 550                 555                 560

Phe Val Lys Thr Cys Gly Ala Pro Pro Cys Asn Leu Gly Pro Thr Gly
                565                 570                 575

Asn Asn Ser Leu Lys Cys Pro Thr Asp Cys Phe Arg Lys His Pro Asp
            580                 585                 590

Ala Thr Tyr Thr Lys Cys Gly Ser Gly Pro Trp Leu Thr Pro Arg Cys
        595                 600                 605

Leu Val His Tyr Pro Tyr Arg Leu Trp His Tyr Pro Cys Thr Leu Asn
    610                 615                 620

Tyr Thr Ile Phe Lys Val Arg Met Tyr Ile Gly Gly Leu Glu His Arg
625                 630                 635                 640

Leu Glu Val Ala Cys Asn Trp Thr Arg Gly Glu Arg Cys Asp Leu Glu
                645                 650                 655

Asp Arg Asp Arg Ala Glu Leu Ser Pro Leu Leu His Thr Thr Thr Gln
            660                 665                 670

Trp Ala Ile Leu Pro Cys Ser Phe Thr Pro Thr Pro Ala Leu Ser Thr
        675                 680                 685

Gly Leu Ile His Leu His Gln Asn Ile Val Asp Thr Gln Tyr Leu Tyr
    690                 695                 700

Gly Leu Ser Ser Ser Ile Val Ser Trp Ala Val Lys Trp Glu Tyr Ile
705                 710                 715                 720

Val Leu Ala Phe Leu Leu Leu Ala Asp Ala Arg Ile Cys Thr Cys Leu
                725                 730                 735

Trp Ile Met Leu Leu Val Cys Gln Ala Glu Ala Leu Glu Asn Val
            740                 745                 750

Ile Val Leu Asn Ala Ala Ala Ala Gly Thr His Gly Phe Phe Trp
        755                 760                 765

Gly Leu Leu Val Ile Cys Phe Ala Trp His Phe Lys Gly Arg Leu Val
    770                 775                 780

Pro Gly Ala Thr Tyr Leu Cys Leu Gly Ile Trp Pro Leu Leu Leu Leu
785                 790                 795                 800

Leu Phe Leu Leu Pro Gln Arg Ala Leu Ala Leu Asp Ser Ser Asp Gly
                805                 810                 815
```

-continued

Gly Thr Val Gly Cys Leu Val Leu Thr Ile Leu Thr Ile Phe Thr Leu
            820                 825                 830

Thr Pro Gly Tyr Lys Lys Met Val Leu Val Ile Trp Trp Leu Gln
        835                 840                 845

Tyr Phe Ile Ala Arg Val Glu Ala Phe Ile His Val Trp Val Pro Pro
850                 855                 860

Leu Gln Val Arg Gly Gly Arg Asp Ala Ile Ile Met Leu Thr Cys Leu
865                 870                 875                 880

Phe His Pro Ala Leu Gly Phe Glu Val Thr Lys Ile Leu Leu Gly Ile
                885                 890                 895

Leu Gly Pro Leu Tyr Leu Leu Gln Tyr Ser Leu Ile Lys Leu Pro Tyr
            900                 905                 910

Phe Ile Arg Ala Arg Ala Leu Leu Arg Ala Cys Leu Leu Ala Lys His
            915                 920                 925

Leu Ala Cys Gly Arg Tyr Val Gln Ala Ala Leu Leu His Leu Gly Arg
        930                 935                 940

Leu Thr Gly Thr Tyr Ile Tyr Asp His Leu Ala Pro Met Lys Asp Trp
945                 950                 955                 960

Ala Ala Ser Gly Leu Arg Asp Leu Ala Val Ala Thr Glu Pro Ile Ile
                965                 970                 975

Phe Ser Pro Met Glu Thr Lys Val Ile Thr Trp Gly Ala Asp Thr Ala
            980                 985                 990

Ala Cys Gly Asp Ile Leu Ala Gly Leu Pro Val Ser Ala Arg Arg Gly
        995                 1000                1005

His Glu Ile Phe Leu Gly Pro Ala Asp Asp Ile Arg Glu Gly Gly
    1010                1015                1020

Trp Arg Leu Leu Ala Pro Ile Thr Ala Tyr Ala Gln Gln Thr Arg
    1025                1030                1035

Gly Leu Leu Gly Ala Ile Val Val Ser Met Thr Gly Arg Asp Arg
    1040                1045                1050

Thr Glu Gln Ala Gly Glu Val Gln Ile Leu Ser Thr Val Ser Gln
    1055                1060                1065

Ser Phe Leu Gly Thr Thr Ile Ser Gly Val Leu Trp Thr Val Tyr
    1070                1075                1080

His Gly Ala Gly Asn Lys Thr Leu Ala Gly Leu Arg Gly Pro Val
    1085                1090                1095

Thr Gln Met Tyr Ser Ser Ala Glu Gly Asp Leu Val Gly Trp Pro
    1100                1105                1110

Ser Pro Pro Gly Thr Arg Ser Leu Glu Pro Cys Lys Cys Gly Ala
    1115                1120                1125

Val Asp Leu Tyr Leu Val Thr Arg Asn Ala Asp Val Ile Pro Ala
    1130                1135                1140

Arg Arg Arg Gly Asp Lys Arg Gly Ala Leu Leu Ser Pro Arg Pro
    1145                1150                1155

Ile Ser Thr Leu Lys Gly Ser Ser Gly Gly Pro Val Leu Cys Pro
    1160                1165                1170

Arg Gly His Val Val Gly Leu Phe Arg Ala Ala Val Cys Ser Arg
    1175                1180                1185

Gly Val Ala Lys Ser Ile Asp Phe Ile Pro Val Glu Thr Leu Asp
    1190                1195                1200

Val Val Thr Arg Ser Pro Thr Phe Ser Asp Asn Ser Thr Pro Pro
    1205                1210                1215

Ala Val Pro Gln Thr Tyr Gln Val Gly Tyr Leu His Ala Pro Thr
    1220                1225                1230

```
Gly Ser Gly Lys Ser Thr Lys Val Pro Val Ala Tyr Ala Ala Gln
1235            1240                1245

Gly Tyr Lys Val Leu Val Leu Asn Pro Ser Val Ala Ala Thr Leu
1250            1255                1260

Gly Phe Gly Ala Tyr Leu Ser Lys Ala His Gly Ile Asn Pro Asn
1265            1270                1275

Ile Arg Thr Gly Val Arg Thr Val Met Thr Gly Glu Ala Ile Thr
1280            1285                1290

Tyr Ser Thr Tyr Gly Lys Phe Leu Ala Asp Gly Gly Cys Ala Ser
1295            1300                1305

Gly Ala Tyr Asp Ile Ile Ile Cys Asp Glu Cys His Ala Val Asp
1310            1315                1320

Ala Thr Ser Ile Leu Gly Ile Gly Thr Val Leu Asp Gln Ala Glu
1325            1330                1335

Thr Ala Gly Val Arg Leu Thr Val Leu Ala Thr Ala Thr Pro Pro
1340            1345                1350

Gly Ser Val Thr Thr Pro His Pro Asp Ile Glu Glu Val Gly Leu
1355            1360                1365

Gly Arg Glu Gly Glu Ile Pro Phe Tyr Gly Arg Ala Ile Pro Leu
1370            1375                1380

Ser Cys Ile Lys Gly Gly Arg His Leu Ile Phe Cys His Ser Lys
1385            1390                1395

Lys Lys Cys Asp Glu Leu Ala Ala Ala Leu Arg Gly Met Gly Leu
1400            1405                1410

Asn Ala Val Ala Tyr Tyr Arg Gly Leu Asp Val Ser Ile Ile Pro
1415            1420                1425

Ala Gln Gly Asp Val Val Val Val Ala Thr Asp Ala Leu Met Thr
1430            1435                1440

Gly Tyr Thr Gly Asp Phe Asp Ser Val Ile Asp Cys Asn Val Ala
1445            1450                1455

Val Thr Gln Ala Val Asp Phe Ser Leu Asp Pro Thr Phe Thr Ile
1460            1465                1470

Thr Thr Gln Thr Val Pro Gln Asp Ala Val Ser Arg Ser Gln Arg
1475            1480                1485

Arg Gly Arg Thr Gly Arg Gly Arg Gln Gly Thr Tyr Arg Tyr Val
1490            1495                1500

Ser Thr Gly Glu Arg Ala Ser Gly Met Phe Asp Ser Val Val Leu
1505            1510                1515

Cys Glu Cys Tyr Asp Ala Gly Ala Ala Trp Tyr Asp Leu Thr Pro
1520            1525                1530

Ala Glu Thr Thr Val Arg Leu Arg Ala Tyr Phe Asn Thr Pro Gly
1535            1540                1545

Leu Pro Val Cys Gln Asp His Leu Glu Phe Trp Glu Ala Val Phe
1550            1555                1560

Thr Gly Leu Thr His Ile Asp Ala His Phe Leu Ser Gln Thr Lys
1565            1570                1575

Gln Ala Gly Glu Asn Phe Ala Tyr Leu Val Ala Tyr Gln Ala Thr
1580            1585                1590

Val Cys Ala Arg Ala Lys Ala Pro Pro Pro Ser Trp Asp Ala Met
1595            1600                1605

Trp Lys Cys Leu Ala Arg Leu Lys Pro Thr Leu Ala Gly Pro Thr
1610            1615                1620

Pro Leu Leu Tyr Arg Leu Gly Pro Ile Thr Asn Glu Val Thr Leu
```

```
                1625                 1630                 1635

Thr His Pro Gly Thr Lys Tyr Ile Ala Thr Cys Met Gln Ala Asp
1640                1645                1650

Leu Glu Val Met Thr Ser Thr Trp Val Leu Ala Gly Gly Val Leu
1655                1660                1665

Ala Ala Val Ala Ala Tyr Cys Leu Ala Thr Gly Cys Val Ser Ile
1670                1675                1680

Ile Gly Arg Leu His Val Asn Gln Arg Val Val Ala Pro Asp
1685                1690                1695

Lys Glu Val Leu Tyr Glu Ala Phe Asp Glu Met Glu Glu Cys Ala
1700                1705                1710

Ser Arg Ala Ala Leu Ile Glu Glu Gly Gln Arg Ile Ala Glu Met
1715                1720                1725

Leu Lys Ser Lys Ile Gln Gly Leu Leu Gln Gln Ala Ser Lys Gln
1730                1735                1740

Ala Gln Asp Ile Gln Pro Ala Met Gln Ala Ser Trp Pro Lys Val
1745                1750                1755

Glu Gln Phe Trp Ala Arg His Met Trp Asn Phe Ile Ser Gly Ile
1760                1765                1770

Gln Tyr Leu Ala Gly Leu Ser Thr Leu Pro Gly Asn Pro Ala Val
1775                1780                1785

Ala Ser Met Met Ala Phe Ser Ala Ala Leu Thr Ser Pro Leu Ser
1790                1795                1800

Thr Ser Thr Thr Ile Leu Leu Asn Ile Met Gly Gly Trp Leu Ala
1805                1810                1815

Ser Gln Ile Ala Pro Pro Ala Gly Ala Thr Gly Phe Val Val Ser
1820                1825                1830

Gly Leu Val Gly Ala Ala Val Gly Ser Ile Gly Leu Gly Lys Val
1835                1840                1845

Leu Val Asp Ile Leu Ala Gly Tyr Gly Ala Gly Ile Ser Gly Ala
1850                1855                1860

Leu Val Ala Phe Lys Ile Met Ser Gly Glu Lys Pro Ser Met Glu
1865                1870                1875

Asp Val Ile Asn Leu Leu Pro Gly Ile Leu Ser Pro Gly Ala Leu
1880                1885                1890

Val Val Gly Val Ile Cys Ala Ala Ile Leu Arg Arg His Val Gly
1895                1900                1905

Pro Gly Glu Gly Ala Val Gln Trp Met Asn Arg Leu Ile Ala Phe
1910                1915                1920

Ala Ser Arg Gly Asn His Val Ala Pro Thr His Tyr Val Thr Glu
1925                1930                1935

Ser Asp Ala Ser Gln Arg Val Thr Gln Leu Leu Gly Ser Leu Thr
1940                1945                1950

Ile Thr Ser Leu Leu Arg Arg Leu His Asn Trp Ile Thr Glu Asp
1955                1960                1965

Cys Pro Ile Pro Cys Ser Gly Ser Trp Leu Arg Asp Val Trp Asp
1970                1975                1980

Trp Val Cys Thr Ile Leu Thr Asp Phe Lys Asn Trp Leu Thr Ser
1985                1990                1995

Lys Leu Phe Pro Lys Leu Pro Gly Leu Pro Phe Ile Ser Cys Gln
2000                2005                2010

Lys Gly Tyr Lys Gly Val Trp Ala Gly Thr Gly Ile Met Thr Thr
2015                2020                2025
```

```
Arg Cys Pro Cys Gly Ala Asn Ile Ser Gly Asn Val Arg Leu Gly
2030                2035                2040

Ser Met Arg Ile Thr Gly Pro Lys Thr Cys Met Asn Thr Trp Gln
2045                2050                2055

Gly Thr Phe Pro Ile Asn Cys Tyr Thr Glu Gly Gln Cys Ala Pro
2060                2065                2070

Lys Pro Pro Thr Asn Tyr Lys Thr Ala Ile Trp Arg Val Ala Ala
2075                2080                2085

Ser Glu Tyr Ala Glu Val Thr Gln His Gly Ser Tyr Ser Tyr Val
2090                2095                2100

Thr Gly Leu Thr Thr Asp Asn Leu Lys Ile Pro Cys Gln Leu Pro
2105                2110                2115

Ser Pro Glu Phe Phe Ser Trp Val Asp Gly Val Gln Ile His Arg
2120                2125                2130

Phe Ala Pro Thr Pro Lys Pro Phe Phe Arg Asp Glu Val Ser Phe
2135                2140                2145

Cys Val Gly Leu Asn Ser Tyr Ala Val Gly Ser Gln Leu Pro Cys
2150                2155                2160

Glu Pro Glu Pro Asp Ala Asp Val Leu Arg Ser Met Leu Thr Asp
2165                2170                2175

Pro Pro His Ile Thr Ala Glu Thr Ala Ala Arg Arg Leu Ala Arg
2180                2185                2190

Gly Ser Pro Pro Ser Glu Ala Ser Ser Ser Val Ser Gln Leu Ser
2195                2200                2205

Ala Pro Ser Leu Arg Ala Thr Cys Thr Thr His Ser Asn Thr Tyr
2210                2215                2220

Asp Val Asp Met Val Asp Ala Asn Leu Leu Met Glu Gly Gly Val
2225                2230                2235

Ala Gln Thr Glu Pro Glu Ser Arg Val Pro Val Leu Asp Phe Leu
2240                2245                2250

Glu Pro Met Ala Glu Glu Glu Ser Asp Leu Glu Pro Ser Ile Pro
2255                2260                2265

Ser Glu Cys Met Leu Pro Arg Ser Gly Phe Pro Arg Ala Leu Pro
2270                2275                2280

Ala Trp Ala Arg Pro Asp Tyr Asn Pro Pro Leu Val Glu Ser Trp
2285                2290                2295

Arg Arg Pro Asp Tyr Gln Pro Pro Thr Val Ala Gly Cys Ala Leu
2300                2305                2310

Pro Pro Pro Lys Lys Ala Pro Thr Pro Pro Pro Arg Arg Arg Arg
2315                2320                2325

Thr Val Gly Leu Ser Glu Ser Thr Ile Ser Glu Ala Leu Gln Gln
2330                2335                2340

Leu Ala Ile Lys Thr Phe Gly Gln Pro Pro Ser Ser Gly Asp Ala
2345                2350                2355

Gly Ser Ser Thr Gly Ala Gly Ala Ala Glu Ser Gly Gly Pro Thr
2360                2365                2370

Ser Pro Gly Glu Pro Ala Pro Ser Glu Thr Gly Ser Ala Ser Ser
2375                2380                2385

Met Pro Pro Leu Glu Gly Glu Pro Gly Asp Pro Asp Leu Glu Ser
2390                2395                2400

Asp Gln Val Glu Leu Gln Pro Pro Pro Gln Gly Gly Gly Val Ala
2405                2410                2415

Pro Gly Ser Gly Ser Gly Ser Trp Ser Thr Cys Ser Glu Glu Asp
2420                2425                2430
```

-continued

```
Asp Thr Thr Val Cys Cys Ser Met Ser Tyr Ser Trp Thr Gly Ala
    2435            2440                2445
Leu Ile Thr Pro Cys Ser Pro Glu Glu Glu Lys Leu Pro Ile Asn
    2450            2455                2460
Pro Leu Ser Asn Ser Leu Leu Arg Tyr His Asn Lys Val Tyr Cys
    2465            2470                2475
Thr Thr Ser Lys Ser Ala Ser Gln Arg Ala Lys Lys Val Thr Phe
    2480            2485                2490
Asp Arg Thr Gln Val Leu Asp Ala His Tyr Asp Ser Val Leu Lys
    2495            2500                2505
Asp Ile Lys Leu Ala Ala Ser Lys Val Ser Ala Arg Leu Leu Thr
    2510            2515                2520
Leu Glu Glu Ala Cys Gln Leu Thr Pro Pro His Ser Ala Arg Ser
    2525            2530                2535
Lys Tyr Gly Phe Gly Ala Lys Glu Val Arg Ser Leu Ser Gly Arg
    2540            2545                2550
Ala Val Asn His Ile Lys Ser Val Trp Lys Asp Leu Leu Glu Asp
    2555            2560                2565
Pro Gln Thr Pro Ile Pro Thr Thr Ile Met Ala Lys Asn Glu Val
    2570            2575                2580
Phe Cys Val Asp Pro Ala Lys Gly Gly Lys Lys Pro Ala Arg Leu
    2585            2590                2595
Ile Val Tyr Pro Asp Leu Gly Val Arg Val Cys Glu Lys Met Ala
    2600            2605                2610
Leu Tyr Asp Ile Thr Gln Lys Leu Pro Gln Ala Val Met Gly Ala
    2615            2620                2625
Ser Tyr Gly Phe Gln Tyr Ser Pro Ala Gln Arg Val Glu Tyr Leu
    2630            2635                2640
Leu Lys Ala Trp Ala Glu Lys Lys Asp Pro Met Gly Phe Ser Tyr
    2645            2650                2655
Asp Thr Arg Cys Phe Asp Ser Thr Val Thr Glu Arg Asp Ile Arg
    2660            2665                2670
Thr Glu Glu Ser Ile Tyr Gln Ala Cys Ser Leu Pro Glu Glu Ala
    2675            2680                2685
Arg Thr Ala Ile His Ser Leu Thr Glu Arg Leu Tyr Val Gly Gly
    2690            2695                2700
Pro Met Phe Asn Ser Lys Gly Gln Thr Cys Gly Tyr Arg Arg Cys
    2705            2710                2715
Arg Ala Ser Gly Val Leu Thr Thr Ser Met Gly Asn Thr Ile Thr
    2720            2725                2730
Cys Tyr Val Lys Ala Leu Ala Ala Cys Lys Ala Ala Gly Ile Val
    2735            2740                2745
Ala Pro Thr Met Leu Val Cys Gly Asp Asp Leu Val Val Ile Ser
    2750            2755                2760
Glu Ser Gln Gly Thr Glu Glu Asp Glu Arg Asn Leu Arg Ala Phe
    2765            2770                2775
Thr Glu Ala Met Thr Arg Tyr Ser Ala Pro Pro Gly Asp Pro Pro
    2780            2785                2790
Arg Pro Glu Tyr Asp Leu Glu Leu Ile Thr Ser Cys Ser Ser Asn
    2795            2800                2805
Val Ser Val Ala Leu Gly Pro Arg Gly Arg Arg Tyr Tyr Leu
    2810            2815                2820
Thr Arg Asp Pro Thr Thr Pro Leu Ala Arg Ala Ala Trp Glu Thr
```

```
                    2825                2830                2835

Val Arg His Ser Pro Ile Asn Ser Trp Leu Gly Asn Ile Ile Gln
    2840                2845                2850

Tyr Ala Pro Thr Ile Trp Val Arg Met Val Leu Met Thr His Phe
    2855                2860                2865

Phe Ser Ile Leu Met Val Gln Asp Thr Leu Asp Gln Asn Leu Asn
    2870                2875                2880

Phe Glu Met Tyr Gly Ser Val Tyr Ser Val Asn Pro Leu Asp Leu
    2885                2890                2895

Pro Ala Ile Ile Glu Arg Leu His Gly Leu Asp Ala Phe Ser Met
    2900                2905                2910

His Thr Tyr Ser His His Glu Leu Thr Arg Val Ala Ser Ala Leu
    2915                2920                2925

Arg Lys Leu Gly Ala Pro Pro Leu Arg Val Trp Lys Ser Arg Ala
    2930                2935                2940

Arg Ala Val Arg Ala Ser Leu Ile Ser Arg Gly Gly Lys Ala Ala
    2945                2950                2955

Val Cys Gly Arg Tyr Leu Phe Asn Trp Ala Val Lys Thr Lys Leu
    2960                2965                2970

Lys Leu Thr Pro Leu Pro Glu Ala Arg Leu Leu Asp Leu Ser Ser
    2975                2980                2985

Trp Phe Thr Val Gly Ala Gly Gly Gly Asp Ile Phe His Ser Val
    2990                2995                3000

Ser Arg Ala Arg Pro Arg Ser Leu Leu Phe Gly Leu Leu Leu Leu
    3005                3010                3015

Phe Val Gly Val Gly Leu Phe Leu Leu Pro Ala Arg
    3020                3025                3030

<210> SEQ ID NO 60
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 60
cacttgcacg gctccaaaga cctggtccca g                              31

<210> SEQ ID NO 61
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 61
ccagcccccc tgggaccagg tctttggag                                 29

<210> SEQ ID NO 62
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 62
atgagtcccc gcagccgcag cagcgtttag gac                            33

<210> SEQ ID NO 63
<211> LENGTH: 32
```

```
<212> TYPE: DNA
<213> ORGANISM: Artificial Sequence
<220> FEATURE:
<223> OTHER INFORMATION: synthetic oligonucleotide

<400> SEQUENCE: 63
gaacgtcatt gtcctaaacg ctgctgcggc tg                              32

<210> SEQ ID NO 64
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 64
caggaggaaa aggagtaaga gtaacggcca aatg                            34

<210> SEQ ID NO 65
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 65
ttgcttgggc atttggccgt tactcttact cc                              32
```